(12) United States Patent
Koenemann et al.

(10) Patent No.: US 11,236,101 B2
(45) Date of Patent: Feb. 1, 2022

(54) CYANOARYL SUBSTITUTED BENZ(OTHI)OXANTHENE COMPOUNDS

(71) Applicant: BASF SE, Ludwigshafen am Rhein (DE)

(72) Inventors: Martin Koenemann, Ludwigshafen (DE); Gerhard Wagenblast, Wachenheim (DE); Sorin Ivanovici, Ludwigshafen (DE); Hannah Stephanie Mangold, Ludwigshafen (DE); Hisatoshi Kura, Amagasaki (JP); Mamiko Matsunaga, Amagasaki (JP)

(73) Assignee: BASF SE, Ludwigshafen am Rhein (DE)

(*) Notice: Subject to any disclaimer, the term of this patent is extended or adjusted under 35 U.S.C. 154(b) by 0 days.

(21) Appl. No.: 16/954,931

(22) PCT Filed: Dec. 18, 2018

(86) PCT No.: PCT/EP2018/085373
§ 371 (c)(1),
(2) Date: Jun. 17, 2020

(87) PCT Pub. No.: WO2019/121602
PCT Pub. Date: Jun. 27, 2019

(65) Prior Publication Data
US 2020/0331927 A1 Oct. 22, 2020

(30) Foreign Application Priority Data
Dec. 19, 2017 (EP) .................... 17208597

(51) Int. Cl.
*C07D 491/06* (2006.01)
*G02F 1/25* (2006.01)
(Continued)

(52) U.S. Cl.
CPC ............ *C07D 491/06* (2013.01); *G02F 1/25* (2013.01); *H01L 31/055* (2013.01); *G02F 1/136245* (2021.01)

(58) Field of Classification Search
CPC .................................................. C07D 491/06
See application file for complete search history.

(56) References Cited

U.S. PATENT DOCUMENTS 2,551,731 A 5/1951 Drewitt et al.
3,163,659 A 12/1964 Sieber
(Continued)

FOREIGN PATENT DOCUMENTS

EP 0 657 436 A2 6/1995
EP 3 072 887 A1 9/2016
(Continued)

OTHER PUBLICATIONS

International Search Report dated Mar. 15, 2019 in PCT/EP2018/085373 filed on Dec. 18, 2018.

*Primary Examiner* — John S Kenyon
(74) *Attorney, Agent, or Firm* — Faegre Drinker Biddle & Reath LLP

(57) ABSTRACT

The present invention relates to a cyanoaryl substituted compound of formula (I), (I) wherein m is 0-4; $R^2$, $R^3$, $R^4$ and $R^5$ are selected from hydrogen, chlorine, bromine and $C_6$-$C_{24}$-aryl, which carries one to three cyano; each $R^1$ independently from each other is selected from bromine, chlorine, cyano, —NRaRb, $C_1$-$C_{24}$-alkyl, $C_1$-$C_{24}$-haloalkyl, C1-C24-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, etc., with the proviso that at least one of the radicals $R^1$, $R^2$, $R^3$, $R^4$ and $R^5$ is $C_6$-$C_{24}$-aryl, which carries one to three cyano; X is O, S, SO or $SO_2$; A is a diradical of the formulae (A.1), (A.2), (A.3), or (A.4) wherein *, $R^6$, $(R^7)n$, $(R^8)o$ and $(R^9)p$ are as defined in the claims and in the description. The invention also relates to the use of said compound(s) in color converters, to said color converters and their use, to lighting devices, to a backlight unit for liquid crystal displays; a liquid crystal display device and a self-emissive display device comprising at least one compound (I).

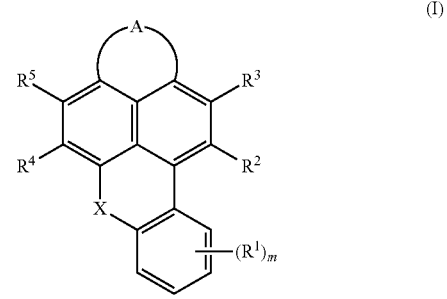

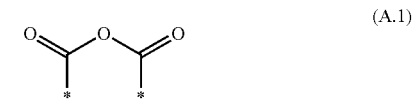

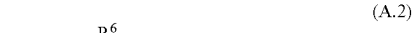

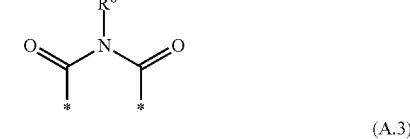

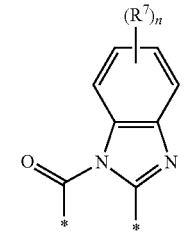

(Continued)

-continued

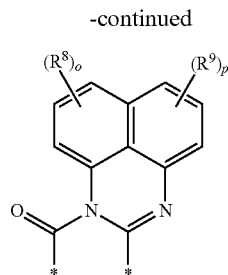

(A.4)

22 Claims, No Drawings

(51) Int. Cl.
  *H01L 31/055* (2014.01)
  *G02F 1/1362* (2006.01)

(56) References Cited

U.S. PATENT DOCUMENTS

| | | |
|---|---|---|
| 4,379,934 A | 4/1983 | Graser et al. |
| 4,446,324 A | 5/1984 | Graser |
| 4,845,223 A | 7/1989 | Seybold et al. |
| 5,998,925 A | 12/1999 | Shimizu et al. |
| 6,245,259 B1 | 6/2001 | Hoehn et al. |
| 6,429,583 B1 | 8/2002 | Levinson et al. |
| 6,576,930 B2 | 6/2003 | Reeh et al. |
| 6,669,866 B1 | 12/2003 | Kummer et al. |
| 6,765,237 B1 | 7/2004 | Doxsee et al. |
| 6,809,347 B2 | 10/2004 | Tasch et al. |
| 6,812,500 B2 | 11/2004 | Reeh et al. |
| 6,943,380 B2 | 9/2005 | Ota et al. |
| 7,267,787 B2 | 9/2007 | Dong et al. |
| 7,311,858 B2 | 12/2007 | Wang et al. |
| 2005/0281775 A1* | 12/2005 | Carrington ............ A61K 31/78 424/70.16 |
| 2011/0068328 A1 | 3/2011 | Koenemann et al. |
| 2011/0282020 A1 | 11/2011 | Sipos |
| 2011/0306804 A1 | 12/2011 | Cortright |
| 2014/0336349 A1 | 11/2014 | Sipos et al. |
| 2015/0183955 A1 | 7/2015 | Deno et al. |
| 2016/0017219 A1 | 1/2016 | Lub et al. |
| 2018/0065980 A1 | 3/2018 | Koenemann et al. |
| 2019/0010165 A1 | 1/2019 | Koenemann et al. |

FOREIGN PATENT DOCUMENTS

| | | |
|---|---|---|
| WO | WO 02/11214 A1 | 2/2002 |
| WO | WO 2005/052087 A1 | 6/2005 |
| WO | WO 2007/006717 A1 | 1/2007 |
| WO | WO 2008/101841 A1 | 8/2008 |
| WO | WO 2009/037283 A1 | 3/2009 |
| WO | WO 2010/081749 A1 | 7/2010 |
| WO | WO 2010/108835 A1 | 9/2010 |
| WO | WO 2010/132740 A2 | 11/2010 |
| WO | WO 2010/132740 A3 | 11/2010 |
| WO | WO 2011/043660 A2 | 4/2011 |
| WO | WO 2011/043660 A3 | 4/2011 |
| WO | WO 2011/043661 A1 | 4/2011 |
| WO | WO 2012/152812 A1 | 11/2012 |
| WO | WO 2012/168395 A1 | 12/2012 |
| WO | WO 2014/122549 A1 | 8/2014 |
| WO | WO 2014/131628 A1 | 9/2014 |
| WO | WO 2014/131628 A9 | 9/2014 |
| WO | WO 2015/019270 A1 | 2/2015 |
| WO | WO 2015/062916 A1 | 5/2015 |
| WO | WO 2015/137804 A1 | 9/2015 |
| WO | WO 2016/151068 A1 | 9/2016 |
| WO | WO 2017/121833 A1 | 7/2017 |
| WO | WO 2018/065502 A1 | 4/2018 |
| WO | WO 2018/134263 A1 | 7/2018 |
| WO | WO 2019/038354 A1 | 2/2019 |

* cited by examiner

CYANOARYL SUBSTITUTED BENZ(OTHI)OXANTHENE COMPOUNDS

The present invention relates to novel cyanoaryl substituted benz(othi)oxanthene compounds and derivatives thereof and to intermediate benzoxanthene compounds. The present invention also relates to the use of these cyanoaryl substituted compounds in color converters, to color converters comprising a polymer matrix material and at least one cyanoaryl substituted benz(othi)oxanthene compound or derivative thereof, to the use of these color converters, to LED lighting devices comprising the same, to a backlight unit for a liquid crystal display comprising the color converter, to a self-emissive and non-emissive display comprising the color converter and to devices producing electric power upon illumination.

BACKGROUND OF THE INVENTION

Nowadays, light emitting diodes (LEDs) are replacing conventional light sources such as incandescent lamps and fluorescent lamps to an ever increasing extent. Lighting devices on the basis of LEDs are used as a source of white light for a wide range of applications, such as for general lighting illumination, architectural, automotive or aviation lighting, as backlight in full-color displays including in flat panel display applications. LED lighting has many advantages, since it has a long lifespan and is very energy efficient.

The emission of white light is always based on the superposition (mixing) of various colors. One approach to generating white light is by use of LED modules with red, green, and blue (RGB) LEDs. Because of the different brightnesses and operating conditions for the various light-emitting diodes, the multi-LED is technically complex and therefore expensive. Furthermore, their color gamuts are fairly limited and component miniaturization of the multi-LED is severely limited.

Another approach to generating white light is the use of phosphor-converted white LEDs, which emit white light based on blue or near-ultraviolet emitting LED chips covered by inorganic phosphor(s) such as a yellow phosphor or yellow and red phosphors. The phosphor(s) which may be dispersed in a binder layer is (are) directly applied to the LED light source (LED chip). A configuration in which the phosphor is applied directly and without intervening space to an LED chip is also referred to as "phosphor on chip" configuration. These LEDs often include a blue LED coated with a cerium-doped yttrium aluminum garnet (Ce:YAG) as yellow phosphor. Ce:YAG absorbs some of the blue light and emits longer-wave light with an emission band about 550 nm, such that the mixing of the blue light transmitted and of the light emitted by Ce:YAG gives rise to white light. The balance of light between the emission from the blue LED and the emissions from the phosphor is important to obtain white light with proper color rendering (CRI) and/or correlated color temperature (CCT). Blue LEDs coated with yellow phosphor are usually characterized by a bluish-white light color corresponding to a high correlated color temperature, usually correlated color temperatures of greater than 6000 K, and a poor color fidelity with a color rendering index of about 70 to 85, limiting the application possibilities. To obtain lighting devices with strong color rendering, a red emitting phosphor should be additionally included in the phosphor-containing layer. In LEDs having phosphor on chip configuration, the phosphors used to date have generally been inorganic ones due to their high thermal and radiation stability and organic phosphors have to date not been suitable for use in phosphor on chip LEDs.

In order to produce white light by color conversion from blue light, there is a further approach in which a color converter (also referred to simply as "converter"), which generally comprises one or more phosphors and a polymer matrix material, is at a certain distance from a blue LED chip. For example, the phosphor may be separated from the blue LED by an air gap. This configuration is also referred to as "remote phosphor". Due to the spatial distance between the primary light source, i.e. the blue LED, and the color converter, the stress resulting from heat and radiation is reduced to such an extent that the requirements on the stability can be achieved by many organic phosphors. Again, the phosphor absorbs a portion of the radiation emitted by the blue LED and re-emits radiation of a different color (wavelength). The phosphor(s) ordinarily re-emit(s) yellow light or a combination of green and red light, yellow and red light or green and yellow light. Mixing of the wavelengths (colors) together results in white light which appears to the human eye as being white in color.

Nowadays, white LEDs with a CCT of less than 10000 K and with an average color rendering index of about 90, often include either a blue LED with a color converter remote from the blue LED or a blue LED coated with an inorganic yellow phosphor and a color converter remote from the blue LED. The color converter generally comprises a mixture of two or three organic phosphors to broaden the spectrum.

In general, the correlated color temperature CCT and the CIE chromaticity coordinates are tunable by varying the relative mixing portion of light emitted by the blue LED to light emitted by the phosphor(s). Thus, inorganic and organic phosphors have a great influence on correlated color temperature, color gamut, color quality as defined by the color rendering index and the CIE chormaticity coordinates, brightness and cost effectiveness of generated white light.

The use of organic phosphors offers various advantages. Firstly, organic phosphors are much higher-yielding due to their significantly higher mass-specific absorption, which means that considerably less material is required for efficient radiation conversion than in the case of inorganic phosphors. Secondly, they allow to tailor the hue of the light and thus allow to create a warm-white LED light. Furthermore, they do not require any materials comprising rare earths, which have to be mined and provided in a costly and inconvenient manner and are available only to a limited degree.

White light can also be generated with organic light emitting diodes (OLEDs) using organic electroluminescent materials. White organic light emitting diodes (WOLEDs) are predominately used for self-emissive display applications.

For some lighting applications such as general lighting applications, key parameters of a white LED are its correlated color temperature (CCT), CIE chromaticity coordinates, average color rendering index (CRI Ra), color rendering index R9 for saturated red and its luminous efficacy. For high-end applications it is often important to provide white light with a high color reproduction (high CRI Ra and high R9 value) at a correlated color temperature which mimics the characteristics of natural light such as daylight having a color temperature about 5000 K or incandescent light having a color temperature about 2700 K to 3500 K.

Sunlight has output at all visible wavelengths with relatively gradual and smooth transitions in contrast to known commercial white LEDs. Commercial white LEDs such as a white LED based on a blue LED coated with yellow phosphor such as Ce:YAG, however, produce a spectrum which is rich in a blue component (blue light emission from the LED) and in a broad yellow component. Red and green components of the white light which stems from the emitted light of the yellow phosphor coating are relatively weak which in turn results an incomplete coverage of the full range of visible wavelengths. This gap in spectral energy and the relative lack in wavelengths other than those emitted by the blue LED limit the color rendition of white light. A color range, which is impaired to a great extend by such white LED light, is the green spectral range. Thus, phosphors with a distinct peak at wavelengths longer than those of the blue-emitting LED but shorter than those of the yellow phospor emission are needed to enhance the green spectrum thereby producing light with a better color rendition.

For some display applications, especially full color display applications, a wide color gamut is of great importance, since it allows more natural, vivid, lifelike colors. Liquid crystal displays (LCDs) are one of the most widely used flat panel displays. In LCD backlighting, nowadays white LEDs are used. When the white light transmits the red, green and blue (RGB) color filters, light that has wavelengths in pass bands of the appropriate color filter is transmitted and light that does not have wavelengths in pass bands of the appropriate color filter is absorbed. Since color filters are typically optimized for light transmission and not color gamut, a color filter of a specific color tends to pass a mixture of colors other than the specific color, resulting in a desaturation of the specific color. Current white LEDs often have broadband light emission and thus the red, green and blue colors emitted are not fully saturated. For enhancing the color gamut of the backlight, the white light should have well-separated emission peaks, so that the distance between RGB primaries become larger and narrow bandpass RGB color filters can be used. In CIE 1931 color space, the green color occupies a large area, and the color coordinates of primary color green has a substantial impact on the color gamut. However, the green part of the visible spectrum is often under-represented by current white LEDs. Thus, a narrow-bandwith emitter is needed whose emission peak matches well with the transmission peak of the green color filter.

Nowadays, organic light emitting diode displays based on white organic light emitting diodes (WOLEDs) with RGB color filters are replacing LCDs, since they are self-emitting devices and do not require a backlight unit. In addition, they allow a thinner display panel, a wider viewing angle, higher contrast ratio, and shorter response time in comparison to LED backlights. A conventional WOLED comprises a glass or clear plastic substrate and a light emitting region with a stack of organic luminescent materials between a cathode layer and an anode layer. The organic light emitting region either emits the three primary colors red, green and blue or the two complementary colors yellow and blue. However, the white light must be filtered through RGB filters which results in absorption loss of light over the unmatched color range as in the case of LCD displays.

Thus, green phosphors, especially narrow-band green phosphors with well separated emission peak, are required to extend the color gamut of displays with RGB filters. Thus, there is an ongoing need for phosphors with narrow band emission to downconvert a part of the blue light to the desired green range of the spectrum to better match with the green color filter in the LCD.

Nowadays, there is also a great need for phosphors for color converters, which can combine illumination with data transmission. A new technology, which utilizes white LEDs for both illumination and data transmission, is known as visible-light communication (VLC). VLC is a rapid growing technological field that aims to implement fast and safe wireless communication to replace or complement existing wireless technologies. Organic phosphor that can be used inter alia as color converters in remote phosphor LEDs offer many potential advantages for VLC due to their visible band gaps, short radiative lifetime, and high fluorescence quantum yield. LiFi (Light Fidelity) is the term established for the transmission of data through illumination using LED lighting that varies in its intensity for high speed wireless communication. Together with the widespread use of LED lighting in offices, streetlights and homes, LiFi is an added benefit to the existing lighting infrastructure. To meet with the requirement of high rates of data transmission in the range of a few nanoseconds and preferably even lower, further organic phosphors are needed.

Numerous organic fluorescent compounds, for example including naphthoylbenzimidazole compounds or benzoxanthene compounds, have been proposed in the prior art which can be excited by a blue LED and re-emit in the green or green-yellow wavelength range (wavelength range between 490-560 nm)

Unpublished PCT/EP2018/072714 describes the use of organic phosphors for use in converters for LiFi applications.

WO 2015/019270 describes naphthoylbenzimidazole compounds which mandatorily carry at least one cyano group and their use as organic fluorescent colorant, in particular their use in color converters for converting light emitted by LEDs.

WO 2014/131628 describes lighting devices comprising (i) a blue LED as light source and (ii) a color converter comprising a polymer matrix and benzoxanthene or benzothioxanthene compounds which do not carry a cyanoaryl group or a cyano group.

WO 2015/062916 describes green/yellow emitting organic fluorescent dyes based on benzimidazoxanthenoisoquinolinone for LED lighting.

WO 2016/151068 describes benzoxanthene compounds and benzothioxanthene compounds and derivatives thereof which mandatorily carry at least one cyano group attached to the benz(othi)oxanthene skeleton and their use for LED lighting.

Accordingly, it is an object of the present invention to provide an organic phosphor which can be excited with blue light at a wavelength range between 400 to 480 nm and emits in the green part of the spectrum, especially in the range from 490 to 560 nm, preferably 490 to 540 nm to overcome the aforementioned drawbacks.

Alternatively or additionally, it is an object of the present invention to provide green organic phosphors with a narrow emission band and a narrow full width at half maximum (FWHM).

Alternatively or additionally, it is an object of the present invention to generate white light with a general color rendering index of greater than 90.

Alternatively or additionally, it is an object of the present invention to provide a color converter for use in full color display devices with broad color gamut.

Alternatively or additionally, it is an object of the present invention to provide large color gamut displays.

Alternatively or additionally, it is an object of the present invention to provide a composition of organic phosphors which allows to provide white light having high color rendering index values (greater than 90), together with a high R9 value (greater than 60) at a correlated color temperature ranging from approximately 2 000 K to 6 500 K.

Alternatively or additionally, it is an object of the present invention to provide a composition of organic phosphors for generating white light at a CCT ranging from 2 000 to 6 500 K with high luminous efficacy (e.g. greater than 230 lm/w), preferably with a high color rendering index and/or a high R9 value.

Alternatively or additionally, it is an object of the present invention to provide further organic phosphors for use in frequency converters for LiFi applications comprising a transmitter for transmitting data and for emitting electromagnetic radiation in the visible spectral range having short excited-state lifetimes in the range of a few nanoseconds, and a good color reproduction and color temperature.

Preferably, the organic phosphors should also feature one or more of the following characteristics:
high fluorescence quantum yield (QY) of at least 90%;
short fluorescent lifetimes in the order of a few nanoseconds;
long-term photostability under blue and/or white light irradiation conditions;
long-term stability towards heat, oxygen and moisture under blue and/or white light irradiation conditions;
easy preparation in high purity.

These and further objects are achieved by the compounds of formula (I) defined herein below.

Moreover, there are also other objects that can be alternatively achieved by the present invention including but not limited to an efficient process for preparing the novel organic phosphors, for preparing a color converter comprising the same, a lighting device and a device producing electric power upon illumination.

These and further objectives are achieved by the compounds of formula (I) defined below.

SUMMARY OF THE INVENTION

Therefore, in a first aspect the present invention relates to cyanoaryl substituted compounds of formula (I)

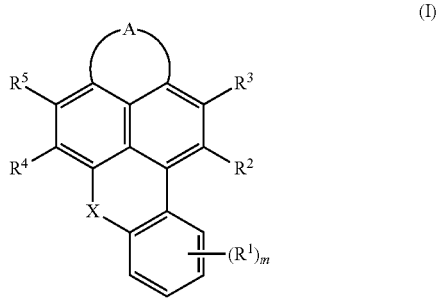

(I)

wherein
m is 0, 1, 2, 3 or 4;
each $R^1$ independently from each other is selected from the group consisting of bromine, chlorine, cyano, —$NR^aR^b$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl, aryloxy and aryl-alkylene in the six last-mentioned radicals are unsubstituted or substituted with 1, 2, 3, 4 or 5 identical or different radicals $R^{1a}$ and where $C_1$-$C_{24}$-alkyl, $C_1$-$C_{24}$-haloalkyl, $C_1$-$C_{24}$-alkoxy, and the alkylene moiety of $C_6$-$C_{24}$-aryl-$C_1$-$C_{10}$-alkylene may be interrupted by one or more groups selected from the group consisting of O, S and $NR^c$;
$R^2$, $R^3$, $R^4$ and $R^5$ are selected from the group consisting of hydrogen, chlorine, bromine, and $C_6$-$C_{24}$-aryl, which carries one, two or three cyano groups; with the proviso that at least one of the radicals $R^1$, $R^2$, $R^3$, $R^4$ and $R^5$ is $C_6$-$C_{24}$-aryl, which carries one, two or three cyano groups;
X is O, S, SO or $SO_2$;
A is a diradical selected from the group consisting of diradicals of the general formulae (A.1), (A.2), (A.3), and (A.4)

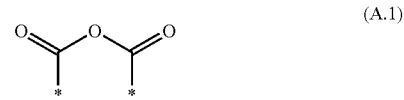

(A.1)

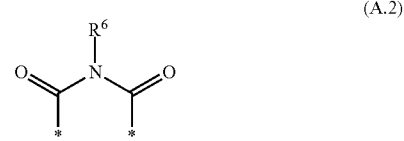

(A.2)

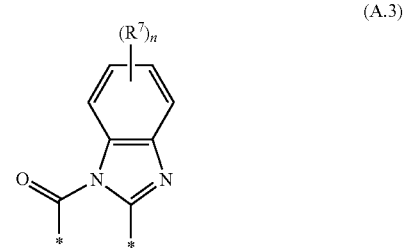

(A.3)

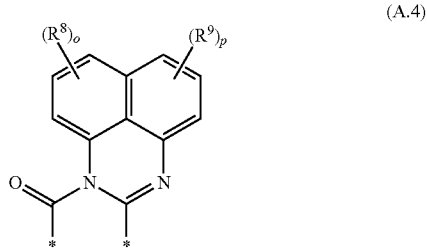

(A.4)

wherein
* in each case denotes the point of attachments to the remainder of the molecule;
n is 0, 1, 2, 3 or 4;
o is 0, 1, 2 or 3;
p is 0, 1, 2 or 3;
$R^6$ is hydrogen, $C_1$-$C_{24}$-alkyl, $C_1$-$C_{24}$-haloalkyl, $C_3$-$C_{24}$-cycloalkyl, $C_6$-$C_{24}$-aryl or $C_6$-$C_{24}$-aryl-$C_1$-$C_{10}$-alkylene, where the rings of cycloalkyl, aryl, and arylalkylene in the three last-mentioned radicals are unsubstituted or substituted with 1, 2, 3, 4 or 5 identical or different radicals $R^{6a}$, and where $C_1$-$C_{24}$-alkyl, $C_1$-$C_{24}$-haloalkyl and the alkylene moiety of $C_6$-$C_{24}$-aryl-$C_1$-$C_{10}$-alkylene may be interrupted by one or more heteroatoms or heteroatomic groups selected from the group consisting of 0, S and NR;
each $R^7$ independently from each other is selected from the group consisting of bromine, chlorine, cyano, —$NR^aR^b$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{7a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from the group consisting of O, S and NR;

each $R^8$ independently from each other is selected from the group consisting of bromine, chlorine, cyano, $NR^aR^b$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{8a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from the group consisting of O, S and NR;

each $R^9$ independently from each other is selected from the group consisting of bromine, chlorine, cyano, $NR^aR^b$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{9a}$ and where $C_1$-$C_{24}$-alkyl, $C_1$-$C_{24}$-haloalkyl, $C_1$-$C_{24}$-alkoxy, $C_1$-$C_{24}$-haloalkoxy and the alkylene moiety of $C_6$-$C_{24}$-aryl-$C_1$-$C_{10}$-alkylene may be interrupted by one or more groups selected from the group consisting of O, S and NR;

$R^{1a}$, $R^{6a}$, $R^{7a}$, $R^{8a}$, $R^{9a}$ are independently of one another selected from the group consisting of $C_1$-$C_{24}$-alkyl, $C_1$-$C_{24}$-fluoroalkyl, $C_1$-$C_{24}$-alkoxy, fluorine, chlorine, bromine and cyano;

$R^a$, $R^b$, $R^c$ are independently of one another selected from the group consisting of hydrogen, $C_1$-$C_{20}$-alkyl, $C_3$-$C_{24}$-cycloalkyl, heterocycloalkyl, hetaryl and $C_6$-$C_{24}$-aryl.

Compounds of formula (I) convert blue light (wavelength range from 400 to 480 nm) to lower energy green light. They appear yellow in color. In particular, they show a strong and distinct emission peak in the wavelength range from 490 to 560 nm, in particular 490 to 540 nm.

The compounds of formula (I) of the present invention are particularly suitable for use in color converters.

Accordingly, in a further aspect of the present invention, provided herein is the use of a compound of the formula (I) as defined herein or a mixture thereof in color converters for converting light emitted from a blue LED with a center wavelength of emission between 400 nm and 480 nm into light of a second, longer wavelength, for converting light emitted from a -white LED, said white LED having a correlated color temperature between 3 000 K and 20 000 K to provide white light having a lower correlated color temperature or in a color converter for transmitting data and for emitting electromagnetic radiation in the visible spectral range or in a display unit.

In a further aspect of the present invention, provided herein, is a color converter comprising at least one cyanoaryl substituted compound of formula (I) as defined herein as a fluorescent dye and a polymer matrix, wherein the polymer matrix is selected from the group consisting of a polystyrene, polycarbonate, polyacrylate, polymethyl methacrylate, polymethacrylate, polyvinylpyrrolidone, polyvinyl acetate, polyvinyl chloride, polybutene, silicone, epoxy resin, vinyl ester resin, polyvinyl alcohol, poly(ethylene vinylalcohol)-copolymer, polyacrylonitrile, polyvinylidene chloride, polystyrene acrylonitrile, polybutylene terephthalate, polyethylene terephthalate, 2,5-furandicarboxylate polyester, polyvinyl butyrate, polyvinyl chloride, polyamides, polyoxymethylenes, polyimides, polyetherimides and mixtures thereof, preferably the polymer matrix comprises or consists of polystyrene, polycarbonate, polyethylene terephthalate or polyethylene furanoate, or the polymer matrix comprises a reaction product of a polymerizable (curable) composition.

In a further aspect of the present invention, provided herein, is the use of the color converter as defined hereinabove for conversion of light generated by a blue LED with a center wavelength of emission between 400 nm and 480 nm to provide white light, for conversion of light generated by a white LED having a correlated color temperature between 3 000 K and 20 000 K to provide white light having a lower correlated color temperature, in a transmitter for transmitting data and for emitting electromagnetic radiation in the visible spectral range or in displays.

In a further aspect of the present invention, provided herein, is a lighting device comprising (i) at least one LED selected from the group consisting of a blue LED with a center wavelength of emission from 400 nm to 480 nm and a white LED having a correlated color temperature between 3 000 K and 20 000 K; and (ii) at least one color converter as defined hereinabove, wherein the at least one color converter is in a remote arrangement from the at least one LED.

In a further aspect of the present invention, provided herein, is a backlight unit for liquid crystal displays, comprising (i) at least one of light source, preferably a white LED having a correlated color temperature between 6 000 and 12 000 K or a blue light emitting diode with a center wavelength of emission from 400 nm to 480 nm; and (ii) at least on color converter as defined herein, wherein the at least one color converter is in a remote phosphor arrangement from the at least one light source.

In a further aspect of the invention, provided herein, is a liquid crystal display device comprising (i) a liquid crystal panel comprising a thin film transistor (TFT) array, a liquid crystal layer, and a color filter array comprising red, green and blue color filters; (ii) at least one of light source; and (iii) at least on color converter as defined herein, where the at least one color converter is arranged between the at least one light source and the liquid crystal panel or is integrated in the color filter array.

In a further aspect of the invention, provided herein, is a self-emissive display device comprising (i) at least one light source; (ii) at least one at least on color converter as defined herein; and (iii) optional a color filter array comprising red, green and blue color filters.

In a further aspect of the present invention, provided herein, is a device producing electric power upon illumination comprising a photovoltaic cell and the color converter as defined hereinabove, where at least a part of the light not absorbed by the photovoltaic cell is absorbed by the color converter.

In a further aspect of the present invention, provided herein, is a benzoxanthene intermediate compound of formula (II.a)

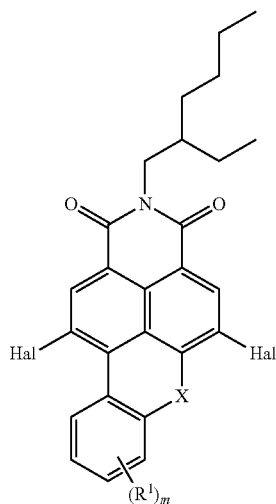

(II.a)

wherein

X is O;

Hal is each chlorine or is each bromine;

$R^1$ is bromine, chlorine, cyano, —$NR^aR^b$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl, aryloxy and aryl-alkylene in the six last-mentioned radicals are unsubstituted or substituted with 1, 2, 3, 4 or 5 identical or different radicals $R^{1a}$ and where $C_1$-$C_{24}$-alkyl, $C_1$-$C_{24}$-haloalkyl, $C_1$-$C_{24}$-alkoxy, and the alkylene moiety of $C_6$-$C_{24}$-aryl-$C_1$-$C_{10}$-alkylene may be interrupted by one or more groups selected from the group consisting of O, S and NR, wherein $R^{1a}$, $R^a$, $R^b$ and $R^c$ are as defined above; and m is 0, 1, 2, 3 or 4.

DESCRIPTION OF THE INVENTION

Fluorescent colorants include all materials which are capable of absorbing light of a particular wavelength and converting it to light of another wavelength.

In the context of the present invention, the term "phosphor" (also referred to as "fluorescent colorant" or simply "colorant") refers to a solid material which converts light of a first wavelength to light of a second different (longer) wavelength. The phosphor may be inorganic or organic. According to the color of light (wavelength of light), the phosphor can be classified as green, yellow, orange, red one, etc.

In the context of the present invention, the terms "organic phosphor", "organic fluorescent colorant" and "organic colorant", are used interchangeably. Organic fluorescent colorants may be organic fluorescent pigments or organic fluorescent dyes. Preferably, they are organic fluorescent dyes.

In the context of the present invention, the term "green phosphor" may in embodiments also relate to a plurality of green phosphors.

In the context of the present invention, the term "red phosphor" may in embodiments also relate to a plurality of red phosphors.

In the context of the present invention, the term "yellow phosphor" may in embodiments also relate to a plurality of yellow phosphors.

The term "conversion material" refers to a material that is excited by a photon of a first wavelength and emits photons of a second (longer), different wavelength.

A quantum dot is a nanocrystal made of semiconductor materials that is small enough to exhibit quantum mechanical properties. Quantum dots are showing remarkably narrow emission spectra, i.e. with extraordinary small FWHM (full width of half maximum). The color output of the dots can be tuned by controlling the size of the crystals. With a smaller size in quantum dots, the quantum dots emit light of a shorter wavelength.

In the context of the present invention, the term "polymer matrix" refers to a polymer in which the phosphor material is dispersed or molecularly dissolved.

In the context of the present invention, the terms "color converter" and "frequency converter", which are also referred to simply as "converter", are understood to mean all physical devices capable of absorbing light of particular wavelengths and converting it to light of a second wavelength. Color converters are, for example, part of lighting devices, especially those lighting devices which utilize UV light or LEDs or OLEDs as a light source, of self-emissive displays, or of fluorescence conversion solar cells.

In the context of the present invention, the term "center wavelength" of a given spectral distribution $F(\lambda)$ is defined as the following average: $\lambda_c = \int \lambda \cdot F(\lambda) \, d\lambda / \int F(\lambda) \, d\lambda$.

In the context of the present invention, the term "full width at half maximum (FWHM)" means the width of a line shape at half of its maximum amplitude.

In the context of the present invention, the term "emissive lifetime $\tau_0$" is defined $\tau_0 = \tau v / QY$, where $\tau v$ is the excited-state lifetime and QY is the fluorescence quantum yield.

In the context of the present invention, the term "excited-state lifetime $\tau v$" which is also referred to as "fluorescence lifetime $\tau v$" corresponds to the mean time, in which the colorant remains in its excited state before it passes through the emission of a photon in its ground state.

In the context of the present invention, the term "fluorescence quantum yield (QY)" is defined as ratio of the number of photons emitted to the number of photons absorbed.

There are two kinds of light emitting diodes. One is based on inorganic materials (LED), while the other one is based on organic materials (OLED). Accordingly, the term "LED" as used herein, refers to inorganic light-emitting diodes, whereas the term "OLED" or "organic LED", as used herein, refers to organic light-emitting diodes. Both kinds of light emitting diodes essentially work on similar principles wherein positive and negative charge carriers are injected into a semiconducting material and light emission occurs when the charge carriers recombine in the light emission zone of the device stack.

In the context of the present invention, a "blue LED" is understood to mean an LED which emits light in the blue range of the electromagnetic spectrum with a center wavelength of emission in the range of 400 to 480 nm, preferably 420 to 480, more preferably 440 to 470 nm, most preferably at 440 to 460 nm. Suitable semiconductor materials are silicon carbide, zinc selenide and nitrides such as aluminum nitride (AlN), gallium nitride (GaN), indium nitride (InN) and indium gallium nitride (InGaN). LEDs typically have a narrow wavelength distribution that is tightly centered about their peak wavelength. Standard InGaN-based blue LEDs are fabricated on a sapphire substrate and peak emission wavelength is usually centered at 445 to 455 nm.

In the context of the present invention, a "white LED" (white light generating LED) is understood to mean an LED that emits light which is perceived as white by a human eye. Examples are multi-LEDs (also called RGB LED system) consisting of a red, a green and a blue LED whose light emissions are mixed to form white light. Further examples are blue LEDs and UV-LEDs whose light passes through phosphor material. Preferred are, blue LEDs coated with an inorganic phosphor material, especially a yellow phosphor such as YAG or red, green, or any other color or combination of phosphors, in particular a yellow phosphor. Likewise preferred are blue LEDs coated with an inorganic phosphor material, especially a yellow phosphor such as YAG or red, green or any other color or combination of phosphors, and with an additional remote phosphor layer.

An UV-LED is a light emitting diode emitting ultraviolet electromagnetic radiation, i. e. electromagnetic radiation having wavelengths below 400 nm, for example in the range from 350 to 400 nm.

In the context of the present invention, a "white organic light emitting diode" (also referred to as white OLED or WOLED) is understood to mean an organic white light emitting diode that emits light which is perceived as white by a human eye.

In the context of the present invention, light of the green wavelength range has a center wavelength of emission between 490 nm to 560 nm, in particular 490 to 540 nm.

In the context of the present invention, the term "white light" relates to light having a correlated color temperature (CCT) between 2 000 to 20 000 K, especially 2 500 to 20 000 K. A commercially available white LED often has a correlated color temperature of 3 000 K or above, for example in the range of 3 000 to 20 000 K or 4°000 to 20°000 K.

In the context of the present invention, an electromagnetic radiation comprising the visible spectral range is also designated as light.

LEDs are not blackbody or incandescent sources and thus have a correlated color temperature (CCT). CCT is the temperature of a blackbody radiator that is perceived by the human eye to emit the same white light as the LEDs. CCT describes the color appearance of white light emitted from electric light sources and is measured in Kelvin. It is determined according to the CIE international standard. White light having higher CCT contains relatively higher intensity in the short wavelength region (blue) and relatively lower intensity in the longer wavelength region (red) compared to white light with lower CCT. Accordingly, higher CCTs generally indicate white light having a more significant blue component or a cool tone while lower CCTs generally indicate light having a more significant red tint or a warm tone. White light having a CCT in the range from 6 000-20 000 K has a relatively high blue component. The CCT of a white LED is determined by the phosphor composition used.

Color rendering (CRI) is a measure how a light source makes the color of an object appear to the human eye and how well subtle variations in color shade are revealed. In general, CRI is considered to be a more important lighting quality than color temperature. According to CIE 17.4, International Lighting Vocabulary, color rendering (CRI) is defined as "the effect of an illuminant on the color appearance of objects by conscious or unconscious comparison with the color appearance under a reference illuminant". The average or general color rendering index Ra is calculated from the differences in the chromaticities of the eight pastel CIE standard (reference) color samples R1 to R8 (CIE 13.3-1995). Negative values are also possible. A reference source, such as black body radiation, is defined as having a CRI index (Ra) of 100 (which is the maximum), i.e. a value of 100 indicates that the source renders colors in a manner identical to the reference. The lower the CRI rating, the less accurately colors will be reproduced. For many general interior illumination applications, a CRI value (Ra) of greater than 80 is acceptable. For general lighting, the color rendering index should be above 85. In applications where accurate color rendering is required, a high CRI Ra of at least 90 is usually highly desirable, so that objects illuminated by the lighting source may appear to have more natural coloring to the human eye.

The average color rendering index Ra does not include coefficients corresponding to six highly saturated colors (R9-R14). Of these, the R9 value corresponds to a strong red color, which may affect a red-green contrast that may be beneficial in rendering colors. Often, the ability to reproduce red colors well is essential for accurately rendering colors, as the color red is often found mixed into processed colors. Thus, if a light source cannot render red correctly, things that are reddish will turn dull. Accordingly, light sources with high CRI Ra and with positive R9 value tend to produce the most vivid colors.

According to the CIE 1931 standard colorimetric system, colors are perceived by human eye following specific color curves. The standard luminosity curve VA accounts for the wavelength dependence of the sensitivity of human eye. The luminosity curve has a maximum possible value of 683 lm/W, for the case of monochromatic light at a wavelength of 555 nm (green). Luminous flux is the measure of the perceived power of light.

In the context of the present invention, the term "color gamut" defines the range of colors that a display can produce. A common method to express the color gamut of displays is the xy chromaticity diagram of the XYZ color system established by the International Commission on Illumination (CIE). The color gamut is defined by the triangle on the xy chromaticity diagram. Additionally or alternatively, the u'v' diagram established by the International Commission on Illumination is used to evaluate the color gamut.

In the context of the present invention, the term "RGB color space" is defined by the chromaticities of the three primary colors red, green and blue, where red, green and blue light are added together to produce a color.

In the context of the present invention, the term "luminous efficacy" quantifies the efficacy of an output spectrum at generating lumens of light produced per watt. The unit of luminous efficacy is lumen/watt.

As used in this specification and the claims, the singular form "a", "an" and "the" includes plural references unless the content clearly dictates otherwise.

The word "essentially" in the context of the present invention encompasses the words "completely", "wholly" and "all". The word encompasses a proportion of 90% or more, such as 95% or more, especially 99% or 100%.

The definitions of the variables specified in the above formulae use collective terms which are generally representative of the respective substituents. The definition $C_n$-$C_m$ gives the number of carbon atoms possible in each case in the respective substituent or substituent moiety.

The expression "halogen" denotes in each case fluorine, bromine, chlorine or iodine, particularly chlorine, bromide or iodine.

In the context of the invention, the expression "in each case unsubstituted or substituted alkyl, cycloalkyl and aryl" represents unsubstituted or substituted alkyl, unsubstituted or substituted cycloalkyl and unsubstituted or substituted aryl.

Likewise, in the context of the invention, the expression "in each case unsubstituted or substituted $C_1$-$C_3$-alkyl, polyalkyleneoxy, $C_1$-$C_3$-alkoxy, $C_1$-$C_{30}$-alkylthio, $C_3$-$C_{20}$-cycloalkyl, $C_3$-$C_{20}$-cycloalkyloxy, $C_6$-$C_{24}$-aryl and $C_6$-$C_{24}$-aryloxy" represents unsubstituted or substituted $C_1$-$C_{30}$-alkyl, unsubstituted or substituted polyalkyleneoxy, unsubstituted or substituted $C_1$-$C_{30}$-alkoxy, unsubstituted or substituted $C_1$-$C_{30}$-alkylthio, unsubstituted or substituted $C_3$-$C_{20}$-cycloalkyl, unsubstituted or substituted $C_3$-$C_{20}$-cycloalkyloxy, unsubstituted or substituted $C_6$-$C_{24}$-aryl and unsubstituted or substituted $C_6$-$C_{24}$-aryloxy.

For the purpose of the present invention, the term "aliphatic radical" refers to an acyclic saturated or unsaturated, straight-chain or branched hydrocarbon radical. Usually the aliphatic radical has 1 to 100 carbon atoms. Examples for an aliphatic radical are alkyl, alkenyl and alkynyl.

For the purpose of the present invention, the term "cycloaliphatic radical" refers to a cyclic, non-aromatic saturated or unsaturated hydrocarbon radical having usually 3 to 20 ring carbon atoms. Examples are cycloalkanes, cycloalkenes, and cycloalkynes. The cycloaliphatic radical may also comprise heteroatoms or heteroatom groups selected from the group consisting of N, O, S and $SO_2$.

The term "alkyl" as used herein and in the alkyl moieties of alkoxy, alkylthio, alkylsulfinyl, alkylsulfonyl, alkylamino, dialkylamino, alkylcarbonyl, alkoxycarbonyl and the like refers to saturated straight-chain or branched hydrocarbon radicals having usually 1 to 100 ("$C_1$-$C_{100}$-alkyl"), 1 to 30 ("$C_1$-$C_{30}$-alkyl"), 1 to 18 ("$C_1$-$C_{18}$-alkyl"), 1 to 12 ("$C_1$-$C_{12}$-alkyl"), 1 to 8 ("$C_1$-$C_8$-alkyl") or 1 to 6 ("$C_1$-$C_6$-alkyl") carbon atoms. Alkyl is preferably $C_1$-$C_{30}$-alkyl, more preferably $C_1$-$C_{20}$-alkyl. Examples of alkyl groups are especially methyl, ethyl, n-propyl, isopropyl, n-butyl, isobutyl, sec-butyl, tert-butyl, n-pentyl, 1-methylbutyl, 1-ethylpropyl, neo-pentyl, n-hexyl, 1-methylpentyl, 2-methylpentyl, 1-ethylbutyl, 2-ethylbutyl, n-heptyl, 1-methylhexyl, 2-methylhexyl, 1-ethylpentyl, 1-propylbutyl, 2-ethylpentyl, n-octyl, 1-methylheptyl, 2-methylheptyl, 1-ethylhexyl, 2-ethylhexyl, 1-propylpentyl, 2-propylpentyl, n-nonyl, etc.

Substituted alkyl groups, depending on the length of the alkyl chain, have one or more (e.g. 1, 2, 3, 4, 5 or more than 5) substituents. These are preferably each independently of each other selected from the group consisting of unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —$COOR^{Ar1}$, $NE^1E^2$, —$NR^{Ar1}COR^{Ar2}$, $CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_1$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

In particular, substituted alkyl groups have one or more, for example 1, 2 or 3 substituent(s) selected from the group consisting of unsubstituted or substituted cycloalkyl, unsubstituted or substituted aryl, fluorine, chlorine, bromine, hydroxyl, alkoxy, polyalkyleneoxy, mercapto, alkylthio, cyano, nitro, $NE^1E^2$, —$NR^{Ar1}COR^{Ar2}$, $CONR^{Ar1}R^{Ar2}$, —$SO_2NR^{Ar1}R^{Ar2}$, and $SO_3R^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

Special embodiments of substituted alkyl groups are alkyl groups, wherein one hydrogen atom has been replaced by an aryl radical ("aralkyl", also referred to hereinafter as arylalkyl or arylalkylene), in particular a phenyl radical. The aryl radical in turn may be unsubstituted or substituted, suitable substituents are the substituents mentioned below for aryl. Particular examples of aryl-$C_1$-$C_4$-alkyl include benzyl, 1-phenethyl, 2-phenetyl, 1-phenylpropyl, 2-phenylpropyl, 3-phenyl-1-propyl, 2-phenyl-2-propyl, naphthylmethyl, naphthylethyl, etc.

Further special embodiments of substituted alkyl groups are alkyl groups where some or all of the hydrogen atoms in these groups may be replaced by halogen atoms as mentioned above, for example $C_1$-$C_4$-haloalkyl.

The term "alkenyl" as used herein refers to straight-chain or branched hydrocarbon groups having usually 2 to 100 ("$C_2$-$C_{100}$-alkenyl"), 2 to 18 ("$C_2$-$C_{18}$-alkenyl"), 2 to 10 ("$C_2$-$C_{10}$-alkenyl"), 2 to 8 ("$C_2$-$C_8$-alkenyl"), or 2 to 6 ("$C_2$-$C_6$-alkenyl") carbon atoms and one or more, e.g. 2 or 3, double bonds in any position. Substituted alkenyl groups, depending on the length of the alkenyl chain, have one or more (e.g. 1, 2, 3, 4, 5 or more than 5) substituents. These are preferably each independently of each other selected from the group consisting of unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —$COOR^{Ar1}$, $NE^1E^2$, —$NR^{Ar1}COR^{Ar2}$, —$CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted alkenyl groups have one or more, for example 1, 2 or 3 substituent(s) selected from the group consisting of unsubstituted or substituted cycloalkyl, unsubstituted or substituted aryl, fluorine, chlorine, bromine, hydroxyl, alkoxy, polyalkyleneoxy, mercapto, alkylthio, cyano, nitro, $NE^1E^2$, —$NR^{Ar1}COR^{Ar2}$, $CONR^{Ar1}R^{Ar2}$, —$SO_2NR^{Ar1}R^{Ar2}$, and $SO_3R^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

The term "alkynyl" as used herein (also referred to as alkyl whose carbon chain may comprise one or more triple bonds) refers to straight-chain or branched hydrocarbon groups having usually 2 to 100 ("$C_2$-$C_{100}$-alkynyl"), 2 to 18 ("$C_2$-$C_{18}$-alknyl"), 2 to 10 ("$C_2$-$C_{10}$-alkynyl"), 2 to 8 ("$C_2$-$C_8$-alkynyl"), or 2 to 6 ("$C_2$-$C_6$-alkynyl") carbon atoms and one or more, e.g. 2 or 3, triple bonds in any position. Substituted alkynyl groups, depending on the length of the alkynyl chain, have one or more (e.g. 1, 2, 3, 4, 5 or more than 5) substituents. These are preferably each independently of each other selected from the group consisting of unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cycloalkyloxy, unsubstituted or substituted aryloxy, unsubstituted or substituted arylthio, cyano, nitro, alkylcarbonyloxy, formyl, acyl, COOH, carboxylate, —$COOR^{Ar1}$, $NE^1E^2$, —$NR^{Ar1}COR^{Ar2}$, $CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted alkynyl groups have one or more, for example 1, 2 or 3 substituent(s) selected from the group consisting of unsubstituted or substituted cycloalkyl, unsubstituted or substituted aryl, fluorine, chlorine, bromine, hydroxyl, alkoxy, polyalkyleneoxy, mercapto, alkylthio, cyano, nitro, $NE^1E^2$, —$NR^{Ar1}COR^{Ar2}$—$CONR^{Ar1}R^{Ar2}$, —$SO_2NR^{Ar1}R^{Ar2}$, and —$SO_3R^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

The term "alkoxy" as used herein refers to an alkyl group bound through an oxygen atom, that is, an "alkoxy" group may be represented as —O-alkyl where alkyl is as defined above. $C_1$-$C_2$-Alkoxy is methoxy or ethoxy. $C_1$-$C_4$-Alkoxy is, for example, methoxy, ethoxy, n-propoxy, 1-methylethoxy (isopropoxy), butoxy, 1-methylpropoxy (sec-butoxy), 2-methylpropoxy (isobutoxy) or 1,1-dimethylethoxy (tert-butoxy).

Accordingly, the term "unsubstituted or substituted alkoxy" as used herein refers to —O-alkyl where alkyl is unsubstituted or substituted as defined above.

The term "polyoxyalkylene" as used herein refers to an alkyl group bound through an oxygen atom to the remainder of the molecule, where alkyl is interrupted by one or more non-adjacent oxygen atoms and alkyl is as defined above.

Accordingly, the term "unsubstituted or substituted polyalkyleneoxy" as used herein refers to —O-alkyl where alkyl is interrupted by one or more non-adjacent oxygen atoms and alkyl is unsubstituted or substituted as defined above.

The term "alkylthio" as used herein refers to an alkyl group bound through a sulfur atom, that is, an "alkylthio" group may be represented as —S-alkyl where alkyl is as defined above. $C_1$-$C_2$-Alkylthio is methylthio or ethylthio. $C_1$-$C_4$-Alkylthio is, for example, methylthio, ethylthio, n-propylthio, 1-methylethylthio (isopropylthio), butylthio, 1-methylpropylthio (sec-butylthio), 2-methylpropylthio (isobutylthio) or 1,1-dimethylethylthio (tert-butylthio).

Accordingly, the term "unsubstituted or substituted alkylthio" as used herein refers to —S-alkyl where alkyl is unsubstituted or substituted as defined above.

The term "cycloalkyl" as used herein refers to mono- or bi- or polycyclic saturated hydrocarbon radicals having usually 3 to 24 ($C_3$-$C_{24}$-cycloalkyl), 3 to 20 ("$C_3$-$C_{20}$-cycloalkyl") atoms, preferably 3 to 8 ("$C_3$-$C_8$-cycloalkyl") or 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 to 12 carbon atoms comprise bicyclo[2.2.1]heptyl, bicyclo[3.1.1]heptyl, bicyclo[2.2.2]octyl, bicyclo[3.3.0]octyl, bicyclo[3.2.1]octyl, bicyclo[3.3.1]nonyl, bicyclo[4.2.1]nonyl, bicyclo[4.3.1]decyl, bicyclo[3.3.2]decyl, bicyclo[4.4.0]decyl, bicyclo[4.2.2]decyl, bicyclo[4.3.2]undecyl, bicyclo[3.3.3]undecyl, bicyclo[4.3.3]dodecyl, and perhydronaphthyl. Examples of polycyclic rings are perhydroanthracyl, perhydrofluorenyl, perhydrochrysenyl, perhydropicenyl, and adamantyl.

Substituted cycloalkyl groups may, depending on the ring size, have one or more (e.g. 1, 2, 3, 4, 5 or more than 5) substituents. These are preferably each independently of each other selected from the group consisting of unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cycloalkyloxy, unsubstituted or substituted aryloxy, unsubstituted or substituted arylthio, cyano, nitro, unsubstituted or substituted alkylcarbonyloxy, formyl, acyl, COOH, carboxylate, —COR$^{Ar1}$, —NE$^1$E$^2$, —NR$^{Ar1}$COR$^{Ar2}$, —CONR$^{Ar1}$R$^{Ar2}$, —SO$_2$NR$^{Ar1}$R$^{Ar2}$ and —SO$_3$R$^{Ar2}$, where E$^1$ and E$^2$ are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cyclo-alkyl or unsubstituted or substituted C$_6$-C$_{10}$-aryl, and R$^{Ar1}$ and R$^{Ar2}$, independently of each other, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl. In particular, substituted cycloalkyl groups have one or more, for example 1, 2 or 3 substituent(s) selected from the group consisting of unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, nitro, NE$^1$E$^2$, —NR$^{Ar1}$COR$^{Ar2}$, —CONR$^{Ar1}$R$^{Ar2}$, —SO$_2$NR$^{Ar1}$R$^{Ar2}$, and —SO$_3$R$^{Ar2}$, where E$^1$, E$^2$, independently of each other, are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, each independently of each, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl.

The term "cycloalkyloxy" as used herein refers to a cycloalkyl group bound through an oxygen atom, that is, a "cycloalkyloxy" group may be represented as —O—cycloalkyl where cycloalkyl is as defined above.

Accordingly, the term "unsubstituted or substituted cycloalkyloxy" as used herein refers to —O-cycloalkyl where cycloalkyl is unsubstituted or substituted as defined above.

The term "cycloalkylthio" as used herein refers to a cycloalkyl group bound through a sulfur atom, that is, a "cycloalkylthio" group may be represented as —S—cycloalkyl where cycloalkyl is as defined above.

Accordingly, the term "unsubstituted or substituted cycloalkylthio" as used herein refers to —S-cycloalkyl where cycloalkyl is unsubstituted or substituted as defined above.

The term "heterocycloalkyl" refers to nonaromatic, partially unsaturated or fully saturated, heterocyclic rings having generally 5 to 8 ring members, preferably 5 or 6 ring members, comprising besides carbon atoms as ring members, one, two, three or four heteroatoms or heteroatom-containing groups selected from the group consisting of O, N, NR$^{cc}$, S, SO and S(O)$_2$ as ring members, wherein R$^{cc}$ is hydrogen, C$_1$-C$_{20}$-alkyl, C$_3$-C$_{24}$-cycloalkyl, heterocycloalkyl, C$_6$-C$_{24}$-aryl or heteroaryl. Examples of heterocycloalkyl groups are especially pyrrolidinyl, piperidinyl, imidazolidinyl, pyrazolidinyl, oxazolidinyl, morpholinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 2-oxazolinyl, 3-oxazolinyl, 4-oxazolinyl and dioxanyl.

Substituted heterocycloalkyl groups may, depending on the ring size, have one or more (e.g. 1, 2, 3, 4, 5 or more than 5) substituents. These are preferably each independently of each other selected from the group consisting of unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —COR$^{Ar1}$, —NE$^1$E$^2$, —NR$^{Ar1}$COR$^{Ar2}$, —CONR$^{Ar1}$R$^{Ar2}$, —SO$_2$NR$^{Ar1}$R$^{Ar2}$ and —SO$_3$R$^{Ar2}$, where E$^1$ and E$^2$ are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, independently of each other, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl. In particular, substituted heterocycloalkyl groups have one or more, for example 1, 2 or 3 substituent(s) selected from the group consisting of unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, nitro, NE$^1$E$^2$, —NR$^{Ar1}$COR$^{Ar2}$, —CONR$^{Ar1}$R$^{Ar2}$, —SO$_2$NR$^{Ar1}$R$^{Ar2}$, and —SO$_3$R$^{Ar2}$, where E$^1$, E$^2$, independently of each other, are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, each independently of each, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl.

For the purpose of the present invention, the term "aryl" refers to a monocyclic aromatic hydrocarbon radical (i.e. phenyl) or fused bi-, tri- or polycyclic aromatic hydrocarbon radical having at least one fused phenyl ring. The number of carbon ring atoms in an aryl group can vary and is ordinarily 6 to 24. If aryl is not a monocyclic aromatic hydrocarbon radical, i.e. phenyl, the term includes for the fused ring(s) the saturated form (perhydro form), the partly unsaturated form (for example the dihydro form or tetrahydro form) or the aromatic form. The term "aryl" includes, for example bicyclic aromatic radicals in which both rings are aromatic and bicyclic aromatic radicals in which only one ring is aromatic. Examples of bi- or tricyclic aromatic carbocycles include naphthyl, 1,2-dihydronaphthyl, 1,4-dihydronaphthyl, 1,2,3,4-tetrahydronaphthyl, indanyl, indenyl, anthracenyl, fluorenyl etc. Preferably, the term "aryl" denotes phenyl and naphthyl.

Substituted aryls may, depending on the number and size of their ring systems, have one or more (e.g. 1, 2, 3, 4, 5 or more than 5) substituents. These are preferably each independently of each other selected from the group consisting of unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —COOR$^{Ar1}$, —NE$^1$E$^2$, —NR$^{Ar1}$COR$^{Ar2}$, —CONR$^{Ar1}$R$^{Ar2}$, —SO$_2$NR$^{Ar1}$R$^{Ar2}$ and SO$_3$R$^{Ar2}$, where E$^1$ and E$^2$ are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, independently of each other, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl. In particular, substituted aryl groups have one or more, for example 1, 2 or 3 substituent(s) selected from the group consisting of unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, nitro, NE$^1$E$^2$, —NR$^{Ar1}$COR$^{Ar2}$, —CONR$^{Ar1}$R$^{Ar2}$, —SO$_2$NR$^{Ar1}$R$^{Ar2}$, and —SO$_3$R$^{Ar2}$, where E$^1$, E$^2$, independently of each other, are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, each independently of each, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl.

Substituted aryl is preferably aryl substituted by at least one alkyl group ("alkaryl", also referred to hereinafter as alkylaryl). Alkaryl groups may, depending on the size of the aromatic ring system, have one or more (e.g. 1, 2, 3, 4, 5, 6, 7, 8, 9 or more than 9) alkyl substituents. The alkyl substituents may be unsubstituted or substituted. In this regard, reference is made to the above statements regarding unsubstituted and substituted alkyl. A special embodiment relates to alkaryl groups, wherein alkyl is unsubstituted. Alkaryl is preferably phenyl which bears 1, 2, 3, 4 or 5, preferably 1, 2 or 3, more preferably 1 or 2 alkyl substituents. Aryl which bears one or more alkyl radicals, is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-n-propylphenyl, 2-, 3- and 4-iso-propylphenyl, 2,4-, 2,5-, 3,5- and 2,6-di-n-propylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutyl-phenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl.

C$_6$-C$_{24}$-aryloxy: C$_6$-C$_{24}$-ary as defined above, which is bonded to the skeleton via an oxygen atom (—O—). Preference is given to phenoxy and naphthyloxy.

Accordingly, the term "unsubstituted or substituted aryloxy" as used herein refers to —O-aryl where aryl is unsubstituted or substituted as defined above.

C$_6$-C$_{24}$-arylthio: C$_6$-C$_{24}$-ary as defined above, which is bonded to the skeleton via a sulfur atom (—S—). Preference is given to phenylthio and naphthylthio.

Accordingly, the term "unsubstituted or substituted arylthio" as used herein refers to —S-aryl where aryl is unsubstituted or substituted as defined above.

In the context of the present invention, the expression "hetaryl" (also referred to as heteroaryl) comprises heteroaromatic, mono- or polycyclic groups. In addition to the ring carbon atoms, these have 1, 2, 3, 4 or more than 4 heteroatoms as ring members. The heteroatoms are preferably selected from the group consisting of oxygen, nitrogen, selenium and sulfur. The hetaryl groups have preferably 5 to 18, e.g. 5, 6, 8, 9, 10, 11, 12, 13 or 14, ring atoms.

Monocyclic hetaryl groups are preferably 5- or 6-membered hetaryl groups, such as 2-furyl (furan-2-yl), 3-furyl (furan-3-yl), 2-thienyl (thiophen-2-yl), 3-thienyl (thiophen-3-yl), 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 4H-[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Polycyclic hetaryl groups have 2, 3, 4 or more than 4 fused rings. The fused-on rings may be aromatic, saturated or partly unsaturated. Examples of polycyclic hetaryl groups are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, dibenzopyrrolyl (carbazolyl), dibenzofuranyl, dibenzothiophenyl, naphtho[2,3-b]thiophenyl, naphtha[2,3-b]furyl, dihydroindolyl, dihydroindolizinyl, dihydroisoindolyl, dihydroquinolinyl and dihydroisoquinolinyl.

Substituted hetaryl groups may, depending on the number and size of their ring systems, have one or more (e.g. 1, 2, 3, 4, 5 or more than 5) substituents. These are preferably each independently of each other selected from the group consisting of unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —COOR$^{Ar1}$, —NE$^1$E$^2$, —NR$^{Ar1}$COR$^{Ar2}$, —CONR$^{Ar1}$R$^{Ar2}$, —SO$_2$NR$^{Ar1}$R$^{Ar2}$ and —SO$_3$R$^{Ar2}$, where E$^1$ and E$^2$ are hydrogen, unsubstituted or substituted C$_1$-C$_{18}$-alkyl, unsubstituted or substituted C$_2$-C$_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted hetarylgroups have one or more, for example 1, 2 or 3 substituent(s) selected from the group consisting of unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, nitro, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, $R^{Ar1}$ and $R^{Ar2}$ are as defined above.

Fused ring systems can comprise alicyclic, aliphatic heterocyclic, aromatic and heteroaromatic rings and combinations thereof, hydroaromatic joined by fusion. Fused ring systems comprise two, three or more (e.g. 4, 5, 6, 7 or 8) rings. Depending on the way in which the rings in fused ring systems are joined, a distinction is made between ortho-fusion, i.e. each ring shares at least one edge or two atoms with each adjacent ring, and peri-fusion in which a carbon atom belongs to more than two rings. Preferred fused ring systems are ortho-fused ring systems.

When # or * appear in a formula showing a substructure of a compound of the present invention, it denotes the attachment bond in the remainder molecule.

The remarks made below as to preferred embodiments of the variables (substituents) of the compounds of formula (I) are valid on their own as well as preferably in combination with each other.

The remarks made below concerning preferred embodiments of the variables further are valid on their own as well as preferably in combination with each other concerning the compounds of formula (I), where applicable, as well as concerning the uses according to the invention.

Compounds of Formula (I)

Preferred compounds according to the invention are compounds of formula (I), wherein the variable X is oxygen.

Preferred compounds according to the invention are compounds of formula (I), wherein $R^2$, $R^3$, $R^4$ and $R^5$ are selected from the group consisting of the group consisting of hydrogen and $C_6$-$C_{10}$-aryl, which carries one, two or three cyano groups.

More preferably, $R^2$ and $R^4$ are selected from the group consisting of $C_6$-$C_{10}$-aryl, which carries one, two or three cyano groups. Particularly preferred $R^2$ and $R^4$ are each phenyl, which carries one, two or three cyano groups, especially one or two cyano group(s). Particularly preferred $R^3$ and $R^5$ are each hydrogen.

According to one embodiment of the invention the variable A in the compounds of formula (I) is a diradical of the formula (A.1).

According to a preferred embodiment of the invention, the variable A in the compounds of formula (I) is a diradical of the formula (A.2). In the context of (A.2), $R^6$ is preferably selected from the group consisting of the group consisting of hydrogen, linear $C_1$-$C_{24}$-alkyl, branched $C_3$-$C_{24}$-alkyl, $C_6$-$C_{10}$-aryl and $C_6$-$C_{10}$-aryl-$C_1$-$C_{10}$-alkylene, where the aryl ring in the two last mentioned moieties is unsubstituted or substituted with 1, 2, 3, 4 or 5 identical or different radicals $R^{6a}$. Especially, $R^6$ is selected from hydrogen, linear $C_1$-$C_{24}$-alkyl, branched $C_3$-$C_{24}$-alkyl, phenyl and phenyl-$C_1$-$C_{10}$-alkylene, where the phenyl ring in the two last mentioned moieties is unsubstituted or substituted with 1, 2, 3, 4 or 5 identical or different radicals $R^{6a}$. More preferably, $R^6$ is selected from the group consisting of linear $C_1$-$C_{24}$-alkyl, a radical of the formula (B.1), a radical of the formula (B.2) and a radical (B.3)

(B.1)

(B.2)

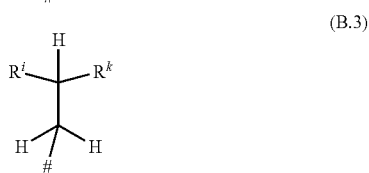

(B.3)

in which
# represents the bonding site to the nitrogen atom;
$R^d$ and $R^e$, in the formula (B.1), independently from each other are selected from the group consisting of $C_1$-$C_{22}$-alkyl, where the sum of the carbon atoms of the $R^d$ and $R^e$ radicals is an integer from 2 to 23;
$R^f$, $R^g$ and $R^h$, in the formula (B.2) are independently selected from the group consisting of $C_1$- to $C_{21}$-alkyl, where the sum of the carbon atoms of the $R^f$, $R^g$ and $R^h$ radicals is an integer from 3 to 23;
$R^i$ and $R^k$, in the formula (B.3) are independently selected from the group consisting of $C_1$- to $C_{21}$-alkyl, where the sum of the carbon atoms of the $R^i$ and $R^k$ radicals is an integer from 2 to 22.

In particular, $R^6$ is linear $C_6$-$C_{24}$-alkyl. Herein, specific examples of $R^6$ are n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-uneicosyl, n-docosyl.

Herein, specific examples of the radical (B.1) are 1-methylethyl, 1-methylpropyl, 1-methylbutyl, 1-methylpentyl, 1-methylhexyl, 1 methylheptyl, 1-methyloctyl, 1-ethylpropyl, 1-ethylbutyl, 1-ethylpentyl, 1-ethylhexyl, 1 ethylheptyl, 1-ethyloctyl, 1-propylbutyl, 1-propylpentyl, 1-propylhexyl, 1 propylheptyl, 1-propyloctyl, 1-butylpentyl, 1-butylhexyl, 1-butylheptyl, 1-butyloctyl, 1 pentylhexyl, 1 pentylheptyl, 1-pentyloctyl, 1-hexylheptyl, 1-hexyloctyl, 1-heptyloctyl.

Herein, a specific example of the radical (B.2) is tert-butyl.

Herein, specific examples of the radical (B.3) are isobutyl, 2-methylbutyl, 2-ethylbutyl, 2-ethylpentyl and 2-ethylhexyl.

Likewise more preferably, $R^6$ is selected from the group consisting of a radical of formula (C.1), a radical of formula (C.2) and a radical of formula (C.3).

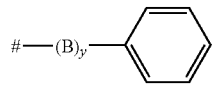

(C.1)

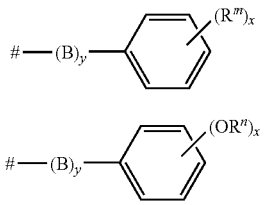

(C. 2)

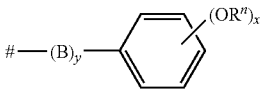

(C. 3)

where
# represents the bonding side to the nitrogen atom;
B where present, is a $C_1$-$C_{10}$-alkylene group which may be interrupted by one or more nonadjacent groups selected from the group consisting of —O— and —S—; y is 0 or 1;
$R^m$ is independently of one another selected from the group consisting of $C_1$-$C_{24}$-alkyl, $C_1$-$C_{24}$-fluoroalkyl, fluorine, chlorine and bromine;
$R^n$ is independently of one another selected from the group consisting of $C_1$-$C_{24}$-alkyl;
x in formulae (C.2) and (C.3) is 1, 2, 3, 4 or 5.

In the context of $R^6$, y in formulae (C.1), (C.2) or (C.3) is preferably zero, i.e. B is absent. In the context of $R^6$, $R^m$ in formula (C.2) is preferably $C_1$-$C_{24}$-alkyl. In the context of $R^6$, x in formula (C.2) is preferably 1 or 2. In the context of $R^6$, $R^n$ in formula (C.3) is preferably $C_1$-$C_{24}$-alkyl. In the context of $R^6$, x in formula (C.3) is preferably 1 or 2.

According to another embodiment of the invention, the variable A in the compounds of formula (I) is a diradical of formula (A.3). In the context of (A.3), n in formula (A.3) is preferably zero, one or two. $R^7$, if present, is preferably selected from the group consisting of cyano, bromine and phenyl which is unsubstituted or carries 1 or 2 radicals selected from the group consisting of $C_1$-$C_4$-alkyl.

According to another embodiment of the invention, the variable A in the compounds of formula (I) is a diradical of formula (A.4). In the context of (A.4), o and p in formula (A.4) are preferably zero, i.e. $R^8$ and $R^9$ are both absent. Likewise preferably, in the context of (A.4), the sum of o and p is 1, 2, 3 or 4. In this context, $R^8$ and $R^9$ are, independently of each other, preferably selected from the group consisting of cyano, bromine, chlorine, $C_1$-$C_4$-alkyl, $C_1$-$C_4$-alkoxy, $C_1$-$C_4$-haloalkyl, phenyl and phenyloxy, wherein phenyl in the two last mentioned radicals is unsubstituted or carries 1, 2 or 3 substituents selected from the group consisting of $C_1$-$C_{10}$-alkyl.

Preferred compounds according to the invention are compounds of formula (I), wherein m in formula (I) is zero, one or two and when m is one or two, each $R^1$ is independently selected from the group consisting of the group consisting of linear $C_1$-$C_{24}$-alkyl, a radical of formula (D.1), a radical of formula (D.2), a radical of formula (D.3), a radical of formula (D.4) and a radical of formula (D.5),

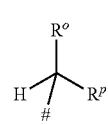

(D.1)

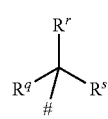

(D.2)

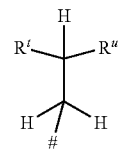

(D.3)

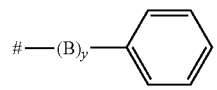

(D. 4)

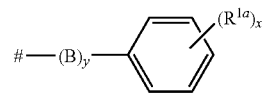

(D.5)

in which
# represents the bonding site to the remainder of the compound of formula (I)
$R^o$ and $R^p$, in the formula (D.1), independently from each other are selected from the group consisting of $C_1$-$C_{22}$-alkyl, where the sum of the carbon atoms of the $R^o$ and $R^p$ radicals is an integer from 2 to 23;
$R^q$, $R^r$ and $R^s$, in the formula (D.2) are independently selected from the group consisting of $C_1$- to $C_{21}$-alkyl, where the sum of the carbon atoms of the $R^q$, $R^r$ and $R^s$ radicals is an integer from 3 to 23;
$R^t$ and $R^u$, in the formula (D.3) are independently selected from the group consisting of $C_1$- to $C_{21}$-alkyl, where the sum of the carbon atoms of the $R^t$ and $R^u$ radicals is an integer from 2 to 22;
B where present, is a $C_1$-$C_{10}$-alkylene group which may be interrupted by one or more nonadjacent groups selected from the group consisting of —O— and —S—;
y in formulae (D.4) and (D.5) is 0 or 1;
x in formula (D.5) is 1, 2 or 3; and
$R^{1a}$ is selected from the group consisting of the group consisting of cyano, $C_1$-$C_{24}$-alkyl and $C_1$-$C_{24}$-alkoxy.

In the context of $R^1$, m in formula (I) is preferably zero, i.e. $R^1$ is absent. Likewise more preferably, in the context of $R^1$, m in formula (I) is one, two or three. $R^1$, if present, is preferably selected from the group consisting of linear $C_6$-$C_{24}$-alkyl. Herein, specific examples of $R^1$ are n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-uneicosyl, n-docosyl.

In the context of $R^1$, $R^o$ and RP in formula (D.1) preferably are each independently $C_1$-$C_{12}$-alkyl. In the context of $R^1$, $R^q$ and $R^s$ in formula (D.2) preferably are each independently $C_1$-$C_6$-alkyl and $R^r$ in formula (D.2) preferably is branched $C_4$-$C_{21}$-alkyl. A specific example of the radical (D.2) is tert-octyl. In the context of $R^1$, x in formula (D.5) preferably is 1 or 2, $R^{1a}$ preferably is cyano or $C_1$-$C_{12}$-alkyl. More preferably, $R^1$ is absent or is a radical of formula D.2 or a radical of formula (D.5), where $R^{1a}$ is cyano, y is 0 and x is 1 or 2. Herein, a preferred example of the radical (D.5) is 4-cyanophenyl.

Examples of preferred compounds of formula (I) are those depicted below:

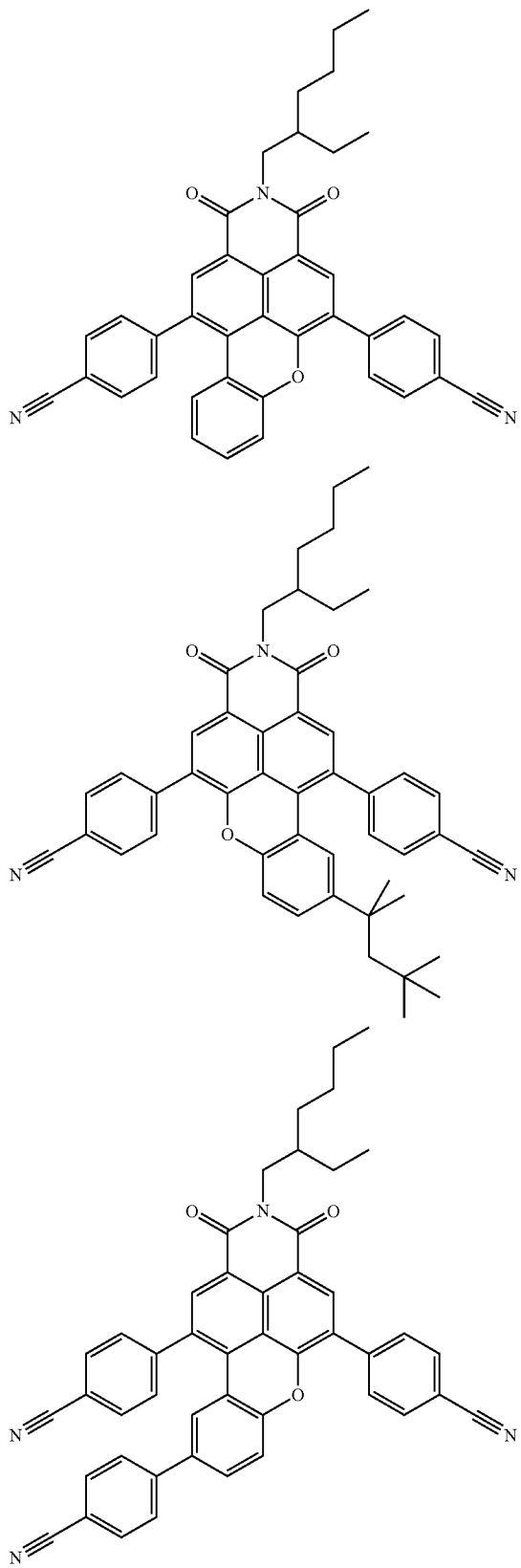

Compounds of formula (I) can be prepared starting from a halogenated benz(othi)oxanthene compound and a cyano-arylboronic acid or ester by analogy to known coupling reactions in the presence of suitable transition metal catalysts, or according to the preparation methods as described hereinbelow or in the experimental part of this application.

Generally, compounds of formula (I) can be prepared by treating a compound of formula (II) with a cyanaryl boronic acid or ester in the sense of a Suzuki coupling as shown in scheme 1.

Scheme 1

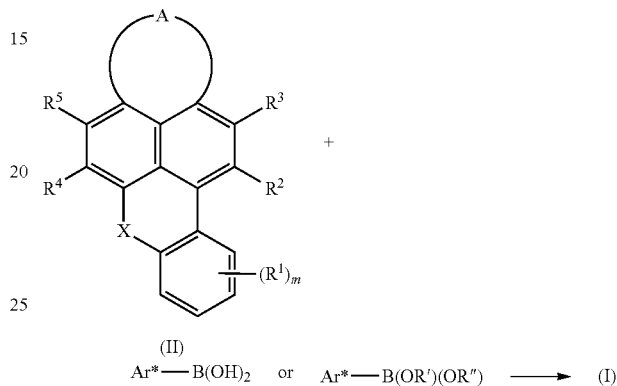

where
($R^1$)$_m$ and A are as defined above;
at least one of the radicals $R^2$, $R^3$, $R^4$ and $R^5$ is halogen selected from the group consisting of chlorine and bromine and the remaining radicals are each hydrogen, with the proviso that radicals different from hydrogen have the same meaning;
X is O or S;
Ar* is $C_6$-$C_{24}$-aryl which carries one, two or three cyano groups;
R', R" independently of each other are selected from the group consisting of $C_1$-$C_{10}$-alkyl or R' and R" together are $C_2$-$C_4$-alkylene which optionally bears 1, 2, 3, 4, 5, 6, 7, or 8 substituents selected from the group consisting of $C_1$-$C_4$-alkyl.

The reaction is usually carried out in the presence of a base and a catalyst, in particular a palladium catalyst. Suitable catalysts are in tetrakis(triphenylphosphine)-palladium(0); bis[bis-(1,2-diphenylphosphino)ethane]palladium (0); bis(dibenzylidene-acetone)palladium(0); tris(dibenzylideneacetone)dipalladium(0); bis(triphenyl-phosphine) palladium(II) chloride; bis(acetonitrile)palladium(II) chloride; [1,1'-bis(diphenylphosphino)ferrocene]-palladium (II) chloride/methylene chloride (1:1) complex; bis(bis-(1, 2-diphenylphosphino)butane]-palladium(II) chloride; palladium(II) acetate; palladium(II) chloride; and palladium(II) acetate/tri-o-tolylphosphine complex or mixtures of phosphines and Pd salts or phosphines and Pd-complexes e.g. dibenzylideneacetone-palladium and tri-tert-butylphosphine (or its tetrafluoroborate); tris(dibenzylideneacetone)dipalladium(0) and tri-tert-butylphosphine; or a polymer-bound Pd-triphenylphosphine catalyst system, e.g. tetrakistriphenylphosphinepalladium on polystyrene.

Suitable bases are, in general, inorganic compounds, such as alkali metal and alkaline earth metal oxides, such as lithium oxide, sodium oxide, calcium oxide and magnesium oxide, alkali metal and alkaline earth metal carbonates, such as lithium carbonate, sodium carbonate, potassium carbonate, caesium carbonate and calcium carbonate, and also alkali metal bicarbonates, such as sodium bicarbonate, organic bases for example alkali metal and alkaline earth metal alkoxides, such as sodium methoxide, sodium ethoxide, potassium ethoxide and potassium tert.-butoxide, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to bases such as sodium carbonate, potassium carbonate, caesium carbonate, triethylamine and sodium bicarbonate.

The reaction is usually carried out in an inert organic organic solvent. Suitable solvents are aliphatic hydrocarbons, such as pentane, hexane, cyclohexane and petroleum ether, aromatic hydrocarbons, such as toluene, o-, m- and p-xylene, ethers, such as diisopropyl ether, tert.-butyl methyl ether, dioxane, anisole and tetrahydrofuran and dimethoxyethane, ketones, such as acetone, methyl ethyl ketone, diethyl ketone and tert.-butyl methyl ketone, and also dimethyl sulfoxide, dimethylformamide and dimethylacetamide. It is also possible to use mixtures of the solvents mentioned, or mixtures with water or water with small amount of organic solvents.

The reaction is usually carried out at temperatures of from 20° C. to 180° C., preferably from 40° C. to 120° C.

After completion of the reaction, the compounds of formula (I) can be isolated by employing conventional methods such as adding the reaction mixture to water, extracting with an organic solvent, concentrating the extract an the like. The isolated compounds (I) can be purified by a technique such as chromatography, recrystallization and the like, if necessary.

The cyanoaryoboronic acids or esters are either commercially available or can be prepared by known methods.

Compounds of formula (II) can be obtained in analogy to the methods described in WO 2016/151068, especially on page 35, first line to page 36, line 8.

Compounds of formula (I), wherein X is SO or $SO_2$, can be obtained by oxidizing compounds of the formula (I), wherein X is S. Suitable oxidizing agents are meta-chloroperbenzoic acid, hypochlorite or hydrogen peroxide.

The compounds of formula (I) usually are green fluorescent dyes. The compounds of the formula (I) exhibit a bathochromic shift of the absorption and/or emission bands compared with the corresponding core cyanated benz(othi)oxanthene compounds. The compounds of formula (I) down-convert blue light to green light. In particular, the compounds of formula (I) allow to create white light with high luminous efficacy and high CRI Ra and high R9 value in a LED-base lighting device. Especially, the compounds of formula (I) have a FWHM of less than 75 nm, preferably at most 70 nm, for example 30 to 70 nm or 30 to 65 nm, when used in a concentration of more than 0.02 wt-%., for example in a concentration range of 0.02 to 0.1% by weight, based on the amount of polymer used. For example, the compounds of formula (I) have a FWHM equal to or below 65 nm when used in a concentration in the range from 0.1 to 2% by weight, based on the amount of polymer used, which enables the compounds of formula (I) to enlarge the color gamut of displays.

The compounds of formula (I) are also characterized by very high stability, especially high lightfastness, thermostability and stability against moisture and oxygen under blue and/or white light irradiation conditions.

The compounds of formula (I) can be easily prepared and obtained in pure form.

Compounds of formula (II), wherein X is O, A is a diradical of formula A.2 with $R^6$ being 2-ethylhexyl, $R^3$ and $R^5$ are hydrogen, $R^2$ and $R^4$ are each chlorine or each bromine and $(R^1)_m$ are as defined above are also novel and thus also part of the present invention. They are very suitable as intermediate compounds for the preparation of compounds of formula (I), where X is O. These compounds are also referred to as compounds of formula (II.a).

Thus, a further object of the present invention relates to a benzoxanthene compound of formula (II.a)

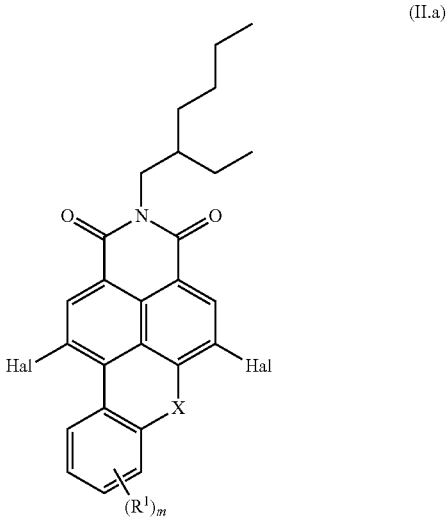

(II.a)

wherein
X is O;
Hal is each bromine or each chlorine;
$R^1$ is bromine, chlorine, cyano, —$NR^aR^b$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl, aryloxy and aryl-alkylene in the six last-mentioned radicals are unsubstituted or substituted with 1, 2, 3, 4 or 5 identical or different radicals $R^{1a}$ and where $C_1$-$C_{24}$-alkyl, $C_1$-$C_{24}$-haloalkyl, $C_1$-$C_{24}$-alkoxy, and the alkylene moiety of $C_6$-$C_{24}$-aryl-$C_1$-$C_{10}$-alkylene may be interrupted by one or more groups selected from the group consisting of O, S and NR, wherein $R^{1a}$, $R^a$, $R^b$ and $R^c$ are as defined above; and
m is 0, 1, 2, 3 or 4.

The compounds of formula (II.a) can be prepared as outlined in scheme 2 below.

Scheme 2

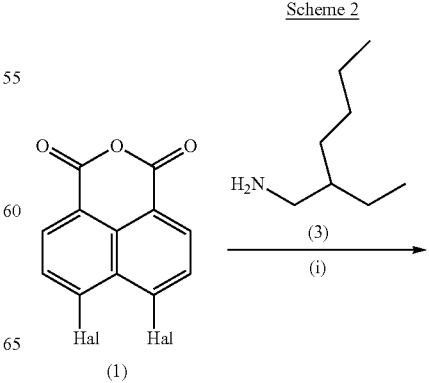

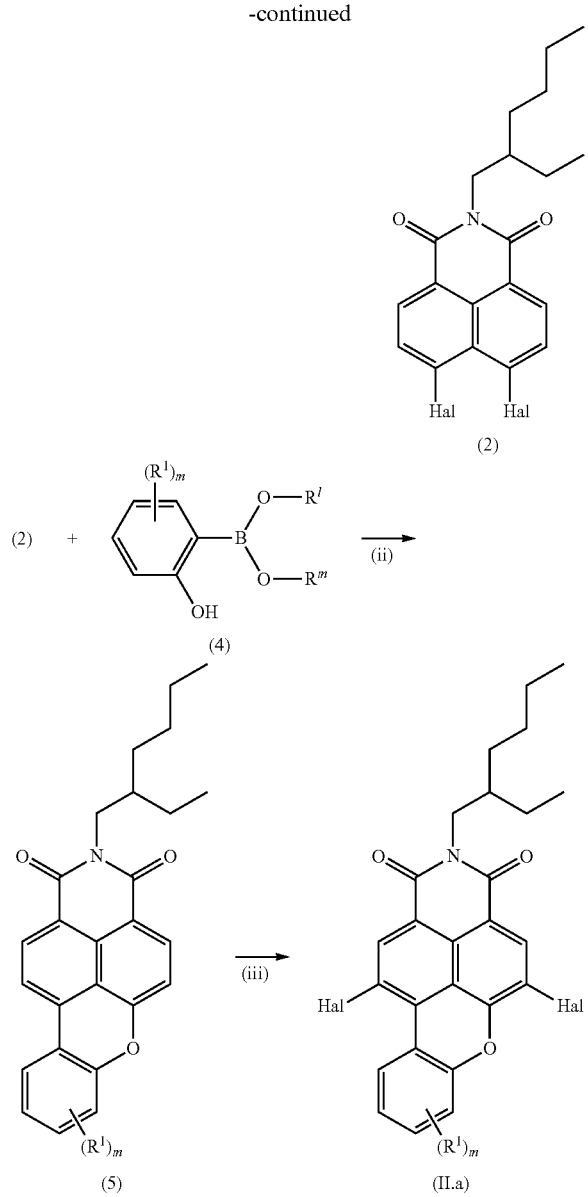

In scheme 2, Hal is each chlorine or each bromine, $(R^1)_m$ is as defined above, $R^l$ and $R^m$ are each independently hydrogen or $C_1$-$C_4$-alkyl, or $R^l$ and $R^m$ together form an 1,2-ethylene or 1,2-propylene moiety the carbon atoms of which may be unsubstituted or may all or in part be substituted by methyl groups.

In step (i) of scheme 2, a 4,5-dihalonaphthalene-1,8-dicarboxylic anhydride of formula (1) is subjected to an imidation reaction using 2-ethylhexylamine of formula (3) to give a 4,5-dihalonaphthalene monoimide of formula (2). Preference is given to carry out the reaction in the presence of a solvent. Suitable solvents are ethanol, toluene and mixtures thereof. It may be advantageous to carry out the reaction in the presence of a condensation accelerator, such as zinc chloride, zinc acetate, zinc propionate or hydrochloride acid. 4,5-Dichloronaphthalene-1,8-dicarboxylic anhydride and 4,5-dibromonaphthalene-1,8-dicarboxylic anhydride are either commerically available or can be prepared as described in U.S. Pat. No. 3,163,659. Likewise, compounds of formula (2) may be prepared in an analogous manner starting from 4,5-dihalonaphthalene-1,8-dicarboxylic acid.

In step (ii) of scheme 2, the compound of formula (2) is treated with a boronic acid derivative of formula (4) in the presence of a base and a transition metal catalyst in the sense of a tandem Suzuki phenoxylation reaction to give a benzoxanthene compound of formula (5). Preferably, the reaction is carried out in the presence of a palladium catalyst, such as for example described in the following literature: Synth. Commun. Vol. 11, p. 513 (1981); Acc. Chem. Res. Vol. 15, pp. 178-184 (1982); Chem. Rev. Vol. 95, pp. 2457-2483 (1995); Organic Letters Vol. 6 (16), p. 2808 (2004); "Metal catalyzed cross coupling reactions", 2$^{nd}$ Edition, Wiley, V C H 2005 (Eds. De Meijere, Diederich); "Handbook of organopalladium chemistry for organic synthesis" (Eds Negishi), Wiley, Interscience, New York, 2002; "Handbook of functionalized organometallics", (Ed. P. Knochel), Wiley, V C H, 2005. As regards suitable Pd-catalysts and bases reference is made to the Suzuki coupling described in Scheme 1 of this application or as outlined on page 38, line 12 to page 39, line 35 of WO 2016/151068.

In step (iii) of scheme 2, the compound of formula (5) is subjected to a bromination or chlorination to give the dihalogenated benzoxanthene compound of formula (II.a). Bromination is typically carried out with elemental bromine in a solvent as described e.g. in WO 2014/131628. Further suitable brominating agents are N-bromosuccinimide and dibromoisocyanuric acid. Suitable solvents are water or aliphatic monocarboxylic acids, and chlorinated hydrocarbons such as chlorobenzene and trichloromethane. Suitable aliphatic monocarboxylic acids are those having 2 to 6 carbon atoms, such as acetic acid, propionic acid, butyric acid, pentanecarboxylic acid and hexanecarboxylic acid, and mixtures thereof. When an aliphatic monocarboxylic acid is used as a solvent, it may be advantageous to use iodine as a catalyst.

Chlorination is typically carried out with elemental chlorine, N-chlorosuccinimide, chlorosulfonic acid, sulfuryl chloride in an inert solvent as described e.g. in US 2011/0068328. A further suitable chlorinating agent is N-chlorosuccinimide.

The compounds of formula (I) can be incorporated without any problem into organic and inorganic materials. In particular, they can be dissolved and homogenously distributed in organic polymers. Accordingly, the compound of the formula (I) and mixtures thereof are especially suitable as fluorescent colorant, especially as fluorescent dyes, in color converters.

Thus, a further object of the present invention relates to the use of a compound of the formula (I) as defined herein or a mixture thereof in color converters for converting light emitted from a blue LED with a center wavelength of emission between 400 nm and 480 nm into light of a second, longer wavelength;

for converting light emitted from a white LED, said white LED having a correlated color temperature between 3 000 K and 20 000 K to provide white light having a lower correlated color temperature; or for transmitting data and for emitting electromagnetic radiation in the visible spectral range.

Owing to their short fluorescence decay time, usually in the range from 0.1 to 9 ns, compounds of formula (I) are also of particular interest for use in converters for data transmission in light fidelity applications comprising a transmitter for transmitting data and for emitting electromagnetic radiation in the visible range.

Color Converter

Accordingly, the present invention further provides a color converter comprising a compound of formula (I) as defined herein above as a fluorescent dye and a polymer matrix, wherein the polymer matrix is selected from the group consisting of a polystyrene, polycarbonate, polyacrylate, polymethyl methacrylate, polymethacrylate, polyvinylpyrrolidone, polyvinyl acetate, polyvinyl chloride, polybutene, silicone, epoxy resin, vinyl ester resin, polyvinyl alcohol, poly(ethylene vinylalcohol)-copolymer, polyacrylonitrile, polyvinylidene chloride, polystyrene acrylonitrile, polybutylene terephthalate, polyethylene terephthalate, 2,5-furandicarboxylate polyester, polyvinyl butyrate, polyvinyl chloride, polyamides, polyoxymethylenes, polyimides, polyetherimides and mixtures thereof, preferably the polymer matrix comprises or consists of polystyrene, polycarbonate, polyethylene terephthalate or polyethylene furanoate; or the polymer matrix comprises a reaction product of a polymerizable (curable) composition.

The term "silicone" is also known as term "(poly)siloxane".

Especially, the polymer matrix material consists essentially or completely of polystyrene, polycarbonate, polyethylene terephthalate or polyethylene furanoate.

Polystyrene is understood here to mean, inter alia, all homo- or copolymers which result from polymerization of styrene and/or derivatives of styrene. Derivatives of styrene are, for example, alkylstyrenes such as alpha-methylstyrene, ortho-, meta-, para-methylstyrene, para-butylstyrene, especially para-tert-butylstyrene, alkoxystyrene such as para-methoxystyrene, para-butoxystyrene, para-tert-butoxystyrene. In general, suitable polystyrenes have a mean molar mass $M_n$ of 10 000 to 1 000 000 g/mol (determined by GPC), preferably 20 000 to 750 000 g/mol, more preferably 30 000 to 500 000 g/mol.

In a preferred embodiment, the matrix of the color converter consists essentially or completely of a homopolymer of styrene or styrene derivatives. More particularly, the polymer matrix material completely consists of polystyrene.

In a further preferred embodiments of the invention, the polymer matrix material consists essentially or completely of a styrene copolymer, which are likewise regarded as polystyrene in the context of this application. Styrene copolymers may comprise, as further constituents, for example, butadiene, acrylonitrile, maleic anhydride, vinylcarbazole or esters of acrylic, methacrylic or itaconic acid as monomers. Suitable styrene copolymers generally comprise at least 20% by weight of styrene, preferably at least 40% and more preferably at least 60% by weight of styrene. In another embodiment, they comprise at least 90% by weight of styrene.

Preferred styrene copolymers are styrene-acrylonitrile copolymers (SAN) and acrylonitrile-butadiene-styrene copolymers (ABS), styrene-1,1'-diphenylethene copolymers, acrylic ester-styrene-acrylonitrile copolymers (ASA), methyl methacrylate-acrylonitrile-butadiene-styrene copolymers (MABS). A further preferred polymer is alpha-methylstyrene-acrylonitrile copolymer (AMSAN). The styrene homo- or copolymers can be prepared, for example, by free-radical polymerization, cationic polymerization, anionic polymerization or under the influence of organometallic catalysts (for example Ziegler-Natta catalysis). This can lead to isotactic, syndiotactic or atactic polystyrene or copolymers. They are preferably prepared by free-radical polymerization. The polymerization can be performed as a suspension polymerization, emulsion polymerization, solution polymerization or bulk polymerization. The preparation of suitable polystyrenes is described, for example, in Oscar Nuyken, Polystyrenes and Other Aromatic Polyvinyl Compounds, in Kricheldorf, Nuyken, Swift, N.Y. 2005, p. 73-150 and references cited therein; and in Elias, Macromolecules, Weinheim 2007, p. 269-275.

In another preferred embodiment, the polymer matrix material consists essentially or completely of polyethylene terephthalate. Polyethylene terephthalate is understood here to mean a homopolymer of polyethylene terephthalate or a copolymer thereof. The polyethylene terephthalate or a copolymer thereof can be a recycled or virgin polyethylene terephthalate or a copolymer thereof. The homopolymer of polyethylene terephthalate is usually obtainable by condensation of ethylene glycol with terephthalic acid or dimethyl terephthalate at elevated temperatures with the removal of water (or methanol). Copolymers are obtainable by partially substituting ethylene glycol by another diol, triol or higher functional-based polyols and/or by partially substituting terephthalic acid by another dicarboxylic acid. Representative examples of diols different from ethylene glycol are 1,2-propanediol, 1,3-propanediol, 1,4-butandiol, neopentylenediol, 1,4-cyclohexanediol, 1,4-cyclohexanedimethanol and polyether diols such as diethylene glycol, and combinations thereof. A representative example of a higher functional based polyol is pentaerythritol. Representative examples of suitable dicarboxylic acids different from terephthalic acid are isopthalic acid, 1-naphthoic acid, 2-naphthoic acid, glutaric acid and combinations thereof. The same effect is achieved by substituting the dimethylester formed from terephthalic acid by another diester formed from dicarboxylic acid different from terephthalic acid. For example, a copolymer of polyethylene terephthalate known as PETG (glycol modified polyethylene terephthalate) comprises structural units derived from terephthalic acid and a mixture of predominately ethylene glycol and a lesser amount of 1,4-cyclohexane dimethanol. The copolymers suppress the crystallization of polyethylene terephthalate.

The term "polyethylene terephthalate" also includes high molecular weight polyethylene terephthalate having chain extender units incorporated in the polymer backbone or polymer chain. Especially, chain extenders are used to connect terminal carboxy groups of two separate ester molecules. Representative examples of chain extenders include tetracarboxylic dianhydrides such as pyromellitic dianhydride, polyacyllactams, di- and polyamines and compounds with high epoxy functionality such as the Jonacryl® brand chain extender commercially available from BASF SE, Germany.

According to this embodiment, the polymer matrix preferably comprises at least 90 wt. % of the homopolymer polyethylene terephthalate based on the total polymer content of matrix material. In other words, at most 10% by weight of the polyethylene terephthalate based on the total polymer content is a copolymer of polyethylene terephthalate. More preferably, the polymer matrix comprises at least 95 wt. % of the homopolymer of polyethylene terephthalate based on the total polymer content of the matrix material. Even more preferably, the polymer matrix consists completely of the homopolymer of polyethylene terephthalate. According to this embodiment, the polyethylene terephthalate polymer matrix material does not comprise any chain extenders in the polymer backbone.

Likewise more particularly, the polymer matrix material consists essentially or completely of polycarbonate. More preferably, the polymer matrix material completely consists of polycarbonate. Polycarbonates are polyesters of carbonic acid with aromatic or aliphatic dihydroxyl compounds. Preferred dihydroxyl compounds are, for example, methylenediphenylenedihydroxyl compounds, for example bisphenol A. One means of preparing polycarbonates is the reaction of suitable dihydroxyl compounds with phosgene in an interfacial polymerization. Another means is the reaction with diesters of carbonic acid such as diphenyl carbonate in a condensation polymerization. The preparation of suitable polycarbonates is described, for example, in Elias, Macromolecules, Weinheim 2007, p. 343-347.

Likewise more particularly, the polymer matrix material consists essentially or completely of 2,5-furandicarboxylate polyester. 2,5-Furandicarboxylate polyesters are obtainable by reacting (i) at least one diol selected from the group consisting of an aliphatic $C_2$-$C_{20}$-diol and a cycloaliphatic $C_3$-$C_{20}$-diol, with (ii) 2,5-furandicarboxylic acid and/or an ester forming derivative thereof and (iii) optionally at least one further dicarboxylic acid selected from the group consisting of 1,2-cyclohexanedicarboxylic acid, 1,4-cyclohexanedicarboxylic acid, 3,4-furandicarboxylic acid, terephthalic acid and 2,6-naphthalic acid and/or an ester forming derivative thereof.

Suitable aliphatic $C_2$-$C_2$-diols are preferably linear or branched $C_2$-$C_{15}$-alkanediols, especially linear or branched $C_2$-$C_{10}$-alkanediols such as ethane-1,2-diol (ethylene glycol), propane-1,2-diol, propane-1,3-diol (propylene glycol), butane-1,3-diol, butane-1,4-diol (butylene glycol), 2-methyl-1,3-propanediol, pentane-1,5-diol, 2,2-dimethyl-1,3-propanediol (neopentyl glycol), hexane-1,6-diol, heptane-1,7-diol, octane-1,8-diol, nonane-1,9-diol, decane-1,10-diol, etc. Suitable cycloaliphatic $C_3$-$C_{20}$-diols are preferably $C_3$-$C_{10}$-cycloalkylenediols, such as 1,2-cyclopentanediol, 1,3-cyclopentanediol, 1,2-cyclohexanediol, 1,4-cyclohexanediol, 1,2-cycloheptanediol or 1,4-cycloheptanediol. Other suitable cycloaliphatic $C_3$-$C_{20}$-diols include 1,3-cyclohexane dimethanol and 1,4-cyclohexane dimethanol, or 2,2,4,4-tetramethyl-1,3-cyclobutanediol, or combinations thereof. Particularly preferred diols are $C_2$-$C_6$-alkanediols, in particular ethane-1,2-diol, propane-1,2-diol, propane-1,3-diol, butane-1,3-diol, butane-1,4-diol, pentane-1,5-diol, 2,2-dimethyl-1,3-propanediol and mixtures thereof. More particularly preferred are ethane-1,2-diol and propane-1,3-diol, especially ethane-1,2-diol.

More particularly preferred are also biologically derived ("bio-derived") $C_2$-$C_{10}$-alkanediols, especially $C_2$-$C_6$-alkanediols such as ethane-1,2-diol and propane-1,3-diol. Bio-based ethane-1,2-diol may be obtained from a lignocellulosic biomass source by the conversion of the carbohydrates therein contained. Methods for preparing $C_2$-$C_{10}$-alkanediols from biomass are known in the art, for example from US 2011/0306804.

Preferably, the diol component (i) is made up exclusively of one diol mentioned as preferred, especially ethane-1,2-diol. The diol component (i) may also comprise two, three or more than three different diols. If two, three or more than three different diols are used, preference is given to those mentioned above as being preferred. In this case, based on the total weight of component (i), ethane-1,2-diol is preferably the major component.

Ester forming derivatives of 2,5-furandicarboxylic acids are especially $C_1$-$C_{10}$-dialkyl esters of 2,5-furandicarboxylic acid. Particularly preferred diesters are $C_1$-$C_6$-dialkyl esters of 2,5-furandicarboxylic acid, especially the dimethyl ester and diethyl ester. Component (ii) may also comprise two, three or more than three different diesters of 2,5-furandicarboxylic acid. 2,5-Furandicarboxylic acid can be produced from bio-based sugars. Routes for the preparation of 2,5-furandicarboxylic acid using air oxidation of 2,5-disubstituted furans such as 5-hydroxymethylfurfural with catalysts comprising Co, Mn and/or Ce were reported recently in WO 2010/132740, WO 2011/043660, WO 2011/043661, US 2011/0282020, US 2014/0336349 and WO 2015/137804. Routes for the preparation of dialkyl ester of 2,5-furandicarboxylic acid are also described for example in WO 2011/043661.

Preferably, the polymer is made up exclusively of (i) one diol selected from the group consisting of an aliphatic $C_2$-$C_{20}$-diol and a cycloaliphatic $C_3$-$C_{20}$-diol and (ii) a 2,5-furandicarboxylic acid or of diester(s) of 2,5-furandicarboxylic acid.

Preferably, the 2,5-furandicarboxylate polyester is selected from the group consisting of poly(ethylene-2,5-furandicarboxylate), poly(propylene-2,5-furandicarboxylate), poly(ethylene-co-propylene-2,5-furandicarboxylate), poly(butylene-2,5-furandicarboxylate), poly(pentylene-2,5-furandicarboxylate), poly(neopentylene-2,5-furandicarboxylate) and mixtures thereof. In particular, the polymeric matrix material for use in the color converter according to the invention can consist of or can consist essentially of from poly(ethylene-2,5-furandicarboxylate), poly(trimethylene-2,5-furandicarboxylate) and poly(butylene-2,5-furandicarboxylate). Especially, the polymeric matrix material for use in the color converter according to the invention consists of poly(ethylene-2,5-furandicarboxylate). In a further specific embodiment, the polymeric matrix material of the color converter comprises a mixture (blend) of different 2,5-furandicarboxylate polyesters as defined above, for example, a blend of poly(ethylene-2,5-furandicarboxylate) and poly(propylene-2,5-furandicarboxylate). Poly(propylene-2,5-furandicarboxylate) is also referred to as poly(trimethylene 2,5-furandicarboxylate); poly(butylene-2,5-furandicarboxylate) is also referred to as poly(tetramethylene 2,5-furan-dicarboxylate), poly(pentylene-2,5-furandicarboxylate) is also referred to as poly(pentamethylene 2,5-furan-dicarboxylate).

Likewise suitable are 2,5-furandicarboxylate polyesters obtainable by reacting at least one diol component (i) as defined above, component (ii) as defined above and at least one further diacid or diester component (iii) selected from the group consisting of 1,2-cyclohexanedicarboxylic acid, 1,4-cyclohexanedicarboxylic acid, 3,4-furandicarboxylic acid, terephthalic acid and 2,6-naphthalic acid and/or an ester forming derivative thereof. Ester forming derivative of 1,2-cyclohexanedicarboxylic acid, 1,4-cyclohexanedicarboxylic acid, 3,4-furandicarboxylic acid, terephthalic acid and 2,6-naphthalic acid are especially the $C_1$-$C_{10}$-dialkyl ester. Particularly preferred esters are $C_1$-$C_6$-dialkyl ester, especially the dimethyl ester and diethyl ester. When using a combination of component (ii) and component (iii), component (ii) is the major component based on the total weight of component (ii) and (iii). Examples are poly(ethylene-2,5-furandicarboxylate-co-1,2-cyclohexanedicarboxylate), poly(ethylene-2,5-furandicarboxylate-co-1,4-cyclohexanedicarboxylate), poly(ethylene-2,5-furandicarboxylate-co-terephthalate), poly(ethylene-2,5-furandicarboxylate-co-2,6-naphthalate) or poly(ethylene-2,5-furandicarboxylate-co-3,4-furandicarboxylate), preferably poly(ethylene-2,5-furandicarboxylate-co-terephthalate), poly(ethylene-2,5-furandicarboxylate-co-2,6-naphthalate) or poly(ethylene-2,5-furandicarboxylate-co-3,4-furandicarboxylate.

The 2,5-furandicarboxylate polyester (A) can be prepared as described in U.S. Pat. No. 2,551,731.

In particular, for use in lighting applications, the polymer matrix material consists of polystyrene.

Likewise in particular, for use in lighting applications, the polymer matrix consists of polycarbonate.

Likewise in particular, for use in lighting applications, the polymer consists of polyethylene terephthalate.

Likewise in particular, for use in lighting applications, the polymer matrix consists of polyethylene furanoate.

In particular, for use in display applications, the polymer matrix is polystyrene or a polystyrene based resin such as the reaction product of a copolymer of styrene, alpha-methylstyrene and acrylic acid, or a copolymer of methyl methacrylate and acrylic acid with 3,4-epoxycyclohexylmethyl (meth)acrylate, or a mixture thereof.

Likewise in particular, for use in display applications, the polymer matrix consists of an homo- or copolymeric acrylate and methacrylate, respectively, especially polyacrylate, polymethyl methacrylate or polymethacrylate.

Likewise in particular, for use in display applications, the polymer matrix consists of polycarbonate.

Likewise in particular, for use in display applications, the polymer matrix consists of polyethylene terephthalate.

Especially for use in display applications, the polymer matrix consists of a vinyl ester resin. Vinyl ester resins also known as epoxy acrylate resins, are understood here to mean unsaturated resins made from the reaction of unsaturated carboxylic acids (ordinarily (meth)acrylic acid) with an epoxy resin. Ordinarily, vinyl ester resins have an epoxy resin backbone with high molecular weight and the vinyl esters have terminal unsaturation. Example of commercial product is the acrylate resin Ripoxy® SPC-2000, available from Showa Denko K.K, Japan.

The term "(meth)acrylic acid used is meant to refer to the acrylic acid as well as to the corresponding methacrylic acid.

Likewise especially for use in display devices, the polymer matrix comprises a reaction product of a polymerizable (curable) composition. Preferably, the polymer matrix consists of the reaction product of a curable composition and wherein the curable resin composition is a photosensitive resist composition comprising at least one binder, at least one monomer, at least one photoinitiator and/or photoacid-generator, optional a thermal radical initiator, optional an organic solvent, optional at least one dispersant, optional at least one surfactant and optional scattering particles.

Examples of suitable binders include unsaturated polyester; vinyl ester resins (epoxy acrylate resins); novolac resins; polyvinyl phenol resins; carboxyl-group containing urethane resins, or a mixture thereof. Examples are, for example, disclosed in WO 2008/101841, page 18, line 28 to page 25, line 21 or US 2015/0183955, paragraph [0100] to paragraph [0101]. Suitable binders are also: polyimides, polyetherimides, epoxy resins, silicones and the like.

A preferred binder is an acrylic resin having carboxylic acid function as a pendant group. Examples are, for example, disclosed in WO 2010/108835, page 4, line 11 to page 11, line 5. A representative example of a commercial product includes Ripoxy®SPC-1000, provided by Showa Denko, K.K., Japan.

The amount of the binder present in the curable composition ranges from 5 to 95% by weight, preferably 10 to 90% by weight, based on the total amount of the solid contents in the photosensitive resist composition.

Examples of suitable monomers include aromatic vinyl compounds such as styrene, alpha-methylstyrene, unsaturated carboxylates such as methyl (meth)acrylate, unsaturated aminoalkyl carboxylate, unsaturated glycidyl carboxylates, unsaturated amides and unsaturated imides, macromonomers having a mono(meth)acryloyl group at the terminal of a polymer molecular chain and polysiloxanes and mixtures thereof. Examples are, for example, described in US 2015/0183955, paragraph [0102].

Examples of suitable monomers include also any acrylate-type monomer. Examples are, for example, those described in WO 2010/108835, page 11, line 13 to page 14, line 13. Preferred monomers include multifunctional (meth)acrylate monomers or oligomers such as dipropyleneglycol diacrylate, 1,6-hexanediol diacrylate, trimethylolpropane triacrylate, pentaerythritol tetraacrylate, dipentaerythritol pentaacrylate, dipentaerythritol hexaacrylate, di-trimethylolpropane tetraacrylate, pentaerythritol triacrylate, tris(2-hydroxy ethyl) isocyanurate triacrylate and mixtures thereof.

The amount of the monomer present in the curable composition ranges from 5 to 70%, preferably 5 to 50%, more preferably 7 to 30% by weight, based on the total amount of the solid contents in the radically photosensitive resist composition.

The use of a photoinitiator is not critical. The photoinitiator ordinarily is selected from the group consisting of benzophenones, aromatic alpha-hydroxyketones, benzilketals, aromatic alpha-aminoketones, phenylglyoxalic acid esters, mono-acylphosphinoxides, bis-acylphosphinoxides, tris-acylphosphinoxides, oximesters derived from aromatic ketones and/or oximesters of the carbazol type. Examples are, for example, described in WO 2010/108835, page 15, line 6 to page 17, line 13 or WO 2010/081749, page 7, line 11 to page 10, line 3.

In one embodiment, the photoinitiator is 1-[4-(phenylthio)phenyl]-,2-(O-benzyloxime) (IRGACURE OXE01®, CAS Number: 253585-83-0; available from BASF SE).

The total amount of the photoinitiator preferably is from 0.01-10% by weight, more preferably 0.05-8% by weight and most preferably 0.5 to 5% by weight, based on the total amount of the solid contents in the photosensitive resist composition.

In some embodiments, the photosensitive resist compositions disclosed herein may further comprise at least photoacid generator. Suitable example of photoacid generators are salts of onium ions, such as sulfonium, iodonium, selenium, ammonium, and phosphonium ions, and anions.

In some embodiments, the photosensitive resist composition disclosed herein may further include a thermal radical initiator like a peroxide or a hydroxylamine ester, as described for example in WO 2010/108835, page 17, line 15 to page 35, line 20.

In some embodiments, the photosensitive resist composition disclosed herein may further include at least one solvent. Examples of suitable solvents are ethylene glycol monomethyl ether acetate, propylene glycol monomethyl ether acetate, propylene glycol monoethyl ether acetate, diethylene glycol dimethyl ether, cyclohexanone, 2-heptanone, 3-heptanone, ethyl 2-hydroxypropionate, 3-methyl-3-methoxybutyl propionate, ethyl 3-methoxypropionate, methyl 3-ethoxypropionate, ethyl 3-ethoxypropionate, n-butyl acetate, isobutyl acetate, n-amyl acetate, isoamyl acetate, n-butyl propionate, ethyl butyrate, isopropyl butyrate, n-butyl butyrate, and ethylpyruvic acid and combinations thereof.

The amount of solvent, if present is from 1 to 80% by weight, based on the total weight of the photosensitive resist composition.

In some embodiments, the photosensitive resist composition disclosed herein may further include at least one dispersant and may further include at least one surfactant. A suitable surfactant is, for example, a cationic, anionic, non-ionic or amphoteric surfactant, or a silicone-based or fluorine-based surfactant. Examples of suitable surfactants include polyoxyethylene alkyl ethers such as polyoxyethylene lauryl ether, polyoxyethylene stearyl ether and polyoxyethylene oleyl ether; polyoxyethylene alkylphenyl ethers such as polyoxyethylene octylphenyl ether and polyoxyethylene nonylphenyl ether; polyethylene glycol diesters such as polyethylene glycol dilaurate and polyethylene glycol distearate; sorbitan fatty acid esters; fatty acid modified polyesters; tertiary amine modified polyurethanes; polyethylene imines; and the like.

Examples of suitable dispersants are polymeric dispersants. Examples include polycarboxylates such as polyurethanes and polyacrylates; unsaturated polyamides; (partial) amine salts, ammonium salts and alkyl amine salts of polycarboxylic acids; polysiloxanes; long-chain polyaminoamide phosphates; hydroxyl group-containing polycarboxylates; and modified products thereof; amides formed by reacting polyesters having a free carboxylic acid group with poly(lower alkylene imines) and salts thereof; and the like. In one embodiment, the dispersant is EFKA 4300, an acrylic block copolymer, available from BASF SE, Germany.

In a preferred embodiment, the preparation of the polymers has been carried out in the absence of oxygen. Preferably, the monomers during the polymerization comprised a total of not more than 1000 ppm of oxygen, more preferably not more than 100 ppm and especially preferably not more than 10 ppm.

Typically, the concentration of the compound of formula (I) is in the range from 0.0001 to 10.0% by weight based on the amount of polymer. For example, for use in general lighting applications, the concentration of the compound of formula (I) is in the range from 0.0001 to 0.8% by weight, preferably 0.002 to 0.8% by weight, more preferably 0.003 to 0.6% by weight, based on the amount of polymer. For example, for use in display applications, the concentration of the compound of formula (I) is in the range from 0.001 to 8.0% by weight, preferably 0.1 to 7.0% by weight, more preferably 0.5 to 5% by weight, based on the amount of polymer used.

Suitable polymers may comprise, as further constituents, additives such as flame retardants, antioxidants, light stabilizers, UV absorbers, free-radical scavengers, antistats. Stabilizers of this kind are known to those skilled in the art.

Suitable antioxidants or free-radical scavengers are, for example, phenols, especially sterically hindered phenols such as butylhydroxyanisole (BHA) or butylhydroxytoluene (BHT), or sterically hindered amines (HALS). Stabilizers of this kind are sold, for example, by BASF under the Irganox® trade name. In some cases, antioxidants and free-radical scavengers can be supplemented by secondary stabilizers such as phosphites or phosphonites, as sold, for example, by BASF under the Irgafos® trade name.

Suitable UV absorbers are, for example, benzotriazoles such as 2-(2-hydroxyphenyl)-2H-benzotriazole (BTZ), triazines such as (2-hydroxyphenyl)-s-triazine (HPT), hydroxybenzophenones (BP) or oxalanilides. UV absorbers of this kind are sold, for example, by BASF under the Uvinul® trade name.

In a preferred embodiment of the invention, suitable polymers do not comprise any antioxidants or free-radical scavengers.

In a further embodiment of the invention, suitable polymers are transparent polymers.

In another embodiment, suitable polymers are opaque polymers.

According to a preferred embodiment, the color converter additionally comprises at least one inorganic white pigment as a scattering body.

Suitable scattering bodies are inorganic white pigments, for example titanium dioxide, barium sulphate, lithopone, zinc oxide, zinc sulphide, zirconia, alumina powder, calcium carbonate with a mean particle size to DIN 13320 of 0.001 to 10 µm, preferably 0.01 to 1 µm, more preferably 0.15 to 0.4 µm, especially scattering bodies based on $TiO_2$.

Scattering bodies are included typically in an amount of 0.01 to 2.0% by weight, preferably 0.05 to 1% by weight, more preferably 0.1 to 0.5% by weight, based in each case on the weight of the polymer of the layer comprising scattering bodies.

The polymers mentioned above serve as a matrix material for the compounds of formula (I) and if present, other organic fluorescent dyes described hereinafter. The fluorescent compound(s) of formula (I) and optionally also other organic fluorescent dyes described hereinafter may either be dissolved in the polymer or may be in the form of a homogeneously distributed mixture. In a preferred embodiment, the color converters comprise, at least one inventive fluorescent dye of formula (I) and at least one further organic fluorescent dye.

Organic Fluorescent Dye B

According to a further preferred embodiment, the color converter comprises at least one further organic fluorescent dye B selected from the group consisting of (B1) an aryloxy-substituted perylene-3,4,9,10-tetracarboxylic acid diimide compound of formula (III)

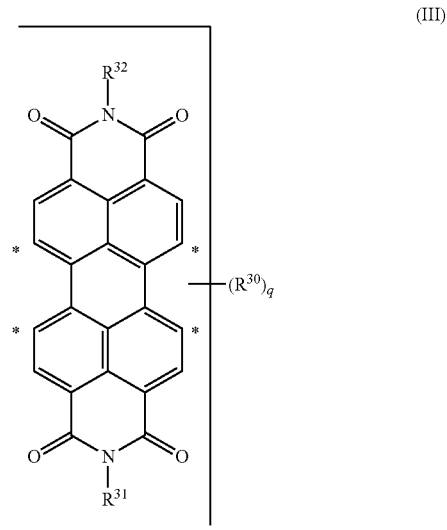

where q is 1 to 4, $R^{30}$ is aryloxy which is unsubstituted or mono- or polysubstituted by halogen, $C_1$-$C_{10}$-alkyl or $C_6$-$C_{10}$-aryl, where the $R^{30}$ radicals are at one or more of the positions indicated by *;

$R^{31}$, $R^{32}$ are each independently $C_1$-$C_0$-alkyl, $C_3$-$C_8$-cycloalkyl, aryl, hetaryl, or aryl-$C_1$-$C_{10}$-alkylene, where the (het)aromatic ring in the three latter radicals is unsubstituted or mono- or polysubstituted by $C_1$-$C_{10}$-alkyl;

and mixtures thereof;

(B2) a perylene-3,4,9,10-tetracarboxylic acid diimide compound of formula (IV)

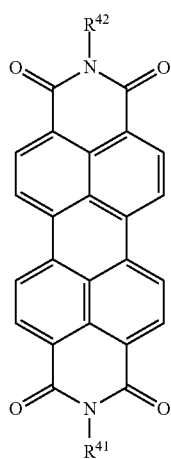

(IV)

in which

R$^{41}$, R$^{42}$ are each independently C$_1$-C$_{30}$-alkyl, C$_3$-C$_8$-cycloalkyl, aryl, hetaryl, or aryl-C$_1$-C$_{10}$-alkylene, where the (het)aromatic ring in the three latter radicals is unsubstituted or mono- or polysubstituted by C$_1$-C$_{10}$-alkyl;

(B3) a perylene-3,4,9,10-tetracarboxylic acid diimide compound with rigid 2,2'-biphenoxy bridges of formula (V)

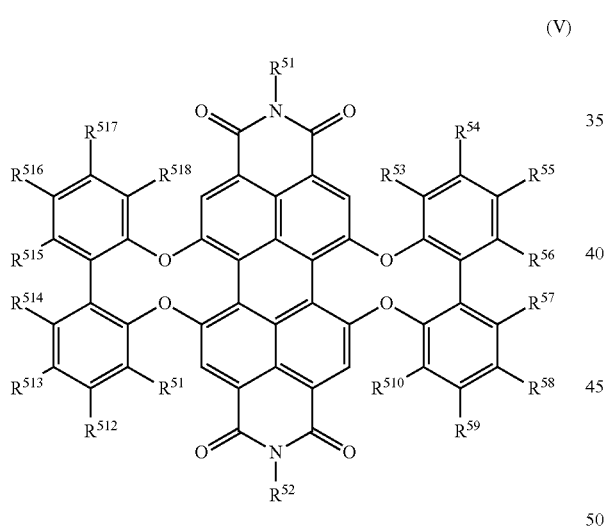

(V)

wherein

R$^{51}$ and R$^{52}$, independently of each other, are selected from the group consisting of hydrogen, in each case unsubstituted or substituted C$_1$-C$_3$-alkyl, polyalkyleneoxy, C$_1$-C$_{30}$-alkoxy, C$_1$-C$_{30}$-alkylthio, C$_3$-C$_{20}$-cycloalkyl, C$_3$-C$_{20}$-cycloalkyloxy, C$_6$-C$_{24}$-aryl and C$_6$-C$_{24}$-aryloxy;

R$^{53}$, R$^{54}$, R$^{55}$, R$^{56}$, R$^{57}$, R$^{58}$, R$^{59}$, R$^{510}$, R$^{511}$, R$^{512}$, R$^{513}$, R$^{514}$, R$^{515}$, R$^{516}$, R$^{517}$ and R$^{518}$ independently of each other, are selected from the group consisting of hydrogen, halogen, cyano, hydroxyl, mercapto, nitro, —NE$^{51}$E$^{52}$, —NR$^{Ar51}$COR$^{Ar52}$, —CONR$^{Ar51}$R$^{Ar52}$, —SO$_2$NR$^{Ar51}$R$^{Ar52}$, —COOR$^{Ar51}$, —SO$_3$R$^{Ar52}$, in each case unsubstituted or substituted C$_1$-C$_3$-alkyl, polyalkyleneoxy, C$_1$-C$_{30}$-alkoxy, C$_1$-C$_{30}$-alkylthio, C$_3$-C$_{20}$-cycloalkyl, C$_3$-C$_{20}$-cycloalkoxy, C$_6$-C$_{24}$-aryl, C$_6$-C$_{24}$-aryloxy and C$_6$-C$_{24}$-arylthio, where R$^{53}$ and R$^{54}$, R$^{54}$ and R$^{55}$, R$^{55}$ and R$^{56}$, R$^{56}$ and R$^{57}$, R$^{57}$ and R$^{58}$, R$^{58}$ and R$^{59}$, R$^{59}$ and R$^{510}$, R$^{511}$ and R$^{512}$, R$^{512}$ and R$^{513}$, R$^{513}$ and R$^{514}$, R$^{55}$ and R$^{515}$, R$^{515}$ and R$^{516}$, R$^{516}$ and R$^{517}$ and/or R$^{517}$ and R$^{518}$ together with the carbon atoms of the biphenylyl moiety to which they are bonded, may also form a further fused aromatic or non-aromatic ring system wherein the fused ring system is unsubstituted or substituted;

where

E$^{51}$ and E$^{52}$, independently of each other, are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl;

R$^{Ar51}$ and R$^{Ar52}$, each independently of each other, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl;

and (B4) a core-cyanated naphthoylbenzimidazole compound of formula (VI)

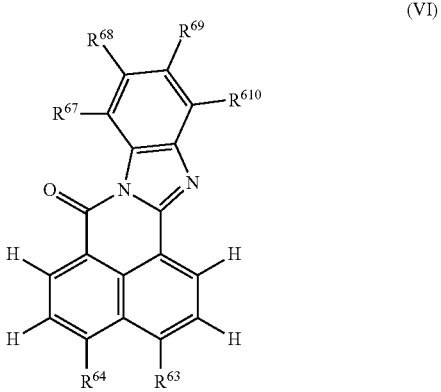

(VI)

wherein one of R$^{63}$ or R$^{64}$ independently o each other is cyano and the other radical R$^{63}$ or R$^{64}$ is selected from the group consisting of cyano, phenyl, 4-cyanophenyl and phenyl which carries 1, 2 or 3 substituents selected from the group consisting of C$_1$-C$_{10}$-alkyl;

R$^{67}$, R$^{68}$, R$^{69}$ and R$^{610}$ independently of each other are hydrogen, cyano, phenyl, 4-cyanophenyl or phenyl which carries 1, 2 or 3 substituents selected from the group consisting of C$_1$-C$_{10}$-alkyl.

Organic Fluorescent Dye (B1)

Suitable examples of compounds of formula (III) are for example the perylene derivatives specified in WO 2007/006717, especially at page 1, line 5 to page 22, line 6; in U.S. Pat. No. 4,845,223, especially col. 2, line 54 to col. 6, line 54; in WO 2014/122549, especially at page 3, line 20 to page 9, line 11; in EP 3072887 and in EP 16192617.5, especially at page 35, line 34 to page 37, line 29; in EP 17187765.7, especially at page 22, line 12 to page 24, line 3. The compounds of formula (III) are usually orange or red fluorescent dyes. Preferred are compounds of formula (III), wherein $R^{31}$ and $R^{32}$ are each independently selected from the group consisting of $C_1$-$C_{10}$-alkyl, 2,6-di($C_1$-$C_{10}$-alkyl) aryl and 2,4-di($C_1$-$C_{10}$-alkyl)aryl. More preferably, $R^{31}$ and $R^{32}$ are identical. Very particularly, $R^{31}$ and $R^{32}$ are each 2,6-diisopropylphenyl or 2,4-di-tert-butylphenyl. $R^{30}$ is preferably phenoxy, which is unsubstituted or substituted by 1 or 2 identical or different substituents selected from the group consisting of fluorine, chlorine, $C_1$-$C_{10}$-alkyl and phenyl. Preferably, a is 2, 3 or 4, in particular 2 or 4.

The compounds of formula (III) can be prepared in analogy to the methods described for example in WO 2007/006717, U.S. Pat. No. 4,845,223, EP 3072887 and WO 2014/122549.

Suitable organic fluorescent dyes B1 are, for example, N,N'-bis(2,6-diisopropylphenyl)-1,6-di(2,6-diisopropylphenoxy)perylene-3,4:9,10-tetracarboximide, N,N'-bis(2,6-diisopropylphenyl)-1,7-di(2,6-diisopropylphenoxy)perylene-3,4:9,10-tetracarboximide, N,N'-bis(2,6-diisopropylphenyl)-1,6-di(p-tert-octylphenoxy)perylene-3,4; 9,10-tetracarboximide, N,N'-bis(2,6-diisopropylphenyl)-1,7-di(p-tert-octylphenoxy)perylene-3,4; 9,10-tetracarboximide, N,N'bis(2,6-diisopropyl,phenyl)-1,6-diphenoxyperylene-3,4; 9,10-tetracarboximide, N,N'bis(2,6-diisopropyl,phenyl)-1,7-diphenoxyperylene-3,4; 9,10-tetracarboximide, N,N'-bis(2,6-diisopropyl,phenyl)-1,6-di(2,6-diphenylphenoxy)perylene-3,4; 9,10-tetracarboximide, N,N'bis(2,6-diiso-propyl,phenyl)-1,7-di(2,6-diphenylphenoxy)perylene-3,4; 9,10-tetracarboximide, N,N'-bis(2,6-diisopropylphenyl)-1,7-di(2,3-difluorophenoxy)perylene-3,4:9,10-tetra-carboximide, N,N'-bis(2,6-diisopropylphenyl)-1,6,7,12-tetraphenoxyperylene-3,4:9,10-tetracarboximide, N,N'-bis(2,6-diisopropylphenyl)-1,6,7,12-tetra(2-phenylphenoxy-)perylene-3,4:9,10-tetracarboximide, N,N'-bis(2,6-diisopropylphenyl)-1,6,7,12-tetra(2-isopropylphenoxy)perylene-3,4:9,10-tetracarboximide, N,N'-bis(2,6-diisopropylphenyl)-1,6,7,12-tetra(2-phenylphenoxy)perylene-3,4:9,10-tetracarboximide, N,N'-bis(2,6-diisopropylphenyl)-1,6,7,12-tetra(2,4-diphenylphenoxy)perylene-3,4:9,10-tetracarbox-imide, N,N'-bis(2,6-diisopropylphenyl)-1,6,7,12-tetra(3-fluorophenoxy)perylene-3,4:9,10-tetracarboximide, N,N'-bis(2,6-diisopropylphenyl)-1,6,7,12-tetra(3-chloro-phenoxy)perylene-3,4:9,10-tetracarboximide, N,N'-bis(2,6-diisopropylphenyl)-1,6,7,12-tetra(2,3-difluorophenoxy)perylene-3,4:9,10-tetracarboximide, N,N'-bis(2,6-diisopropyl-phenyl)-1,6,7,12-tetra(2,5-difluorophenoxy)perylene-3,4:9,10-tetracarboximide, N,N'-bis(2,6-diisopropylphenyl)-1,6,7,12-tetra(2,6-difluorophenoxy)perylene-3,4:9,10-tetracarboximide, N,N'-bis(2,6-diisopropylphenyl)-1,6,7,12-tetra(2,3-dichlorophenoxy)perylene-3,4:9,10-tetracarboximide, N,N'-bis(2,6-diisopropylphenyl)-1,6,7,12-tetra(2,6-dichlorophenoxy)perylene-3,4:9,10-tetracarboximide, N,N'-bis(2,6-diisopropylphenyl)-1,6,7,12-tetra(2,5-dichlorophenoxy)perylene-3,4:9,10-tetracarboximide.

In particular, the organic fluorescent dye (B1) is selected from the group consisting of compounds III-1, III-2, III-3 and III-4.

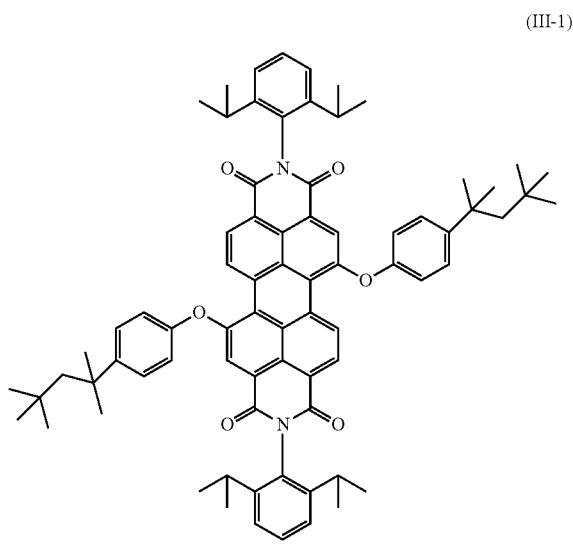

(III-1)

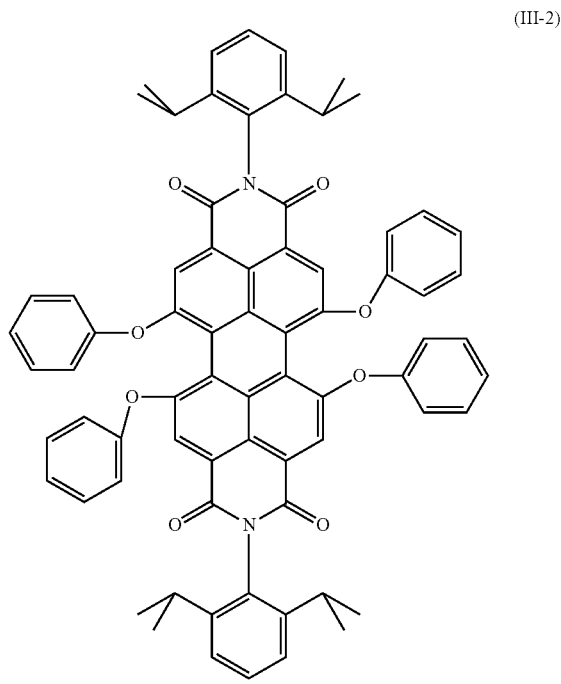

(III-2)

(III-3)

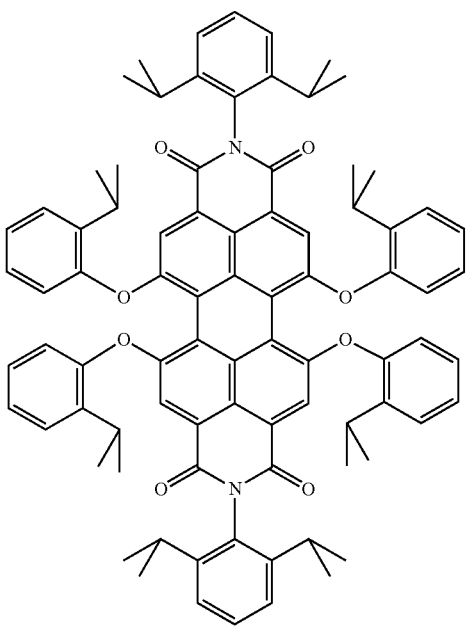

(III-4)

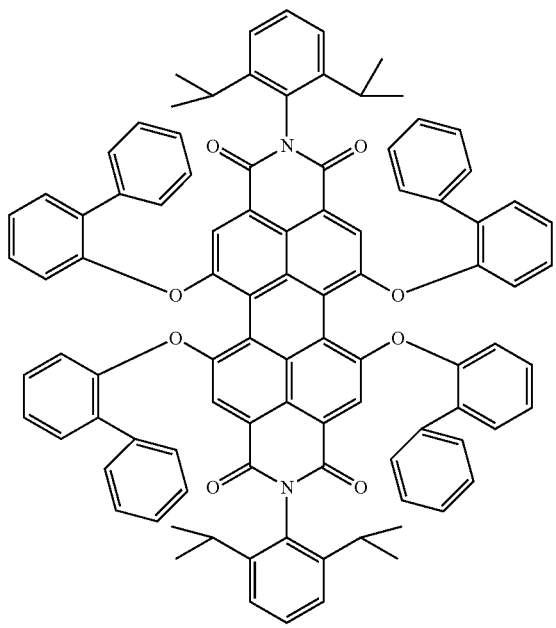

Organic Fluorescent Dye (B2)

Compounds of formula (IV) are well known in the art, e.g. from U.S. Pat. Nos. 4,379,934, 4,446,324 or EP 0657436. They can be prepared by conventional processes, for example by condensing perylene-3,4,9,10-tetracarboxylic acid or its dianhydride with amines. They are usually orange fluorescent dyes. Preferably, in compounds of formula (IV), $R^{41}$ and $R^{42}$ are a linear or branched $C_1$-$C_{18}$ alkyl radical, a $C_4$-$C_8$ cycloalkyl radical which may be mono- or polysubstituted by halogen or by linear or branched $C_1$-$C_{18}$ alkyl, or phenyl or naphthyl which may be mono- or polysubstituted by halogen or by linear or branched $C_1$-$C_{18}$ alkyl. Preferably, $R^{41}$ and $R^{42}$ have the same meaning. In one embodiment, $R^{41}$ and $R^{42}$ in formula (IV) represents compounds with what is called swallowtail substitution, as specified in WO 2009/037283 A1 at page 16 line 19 to page 25 line 8. In a preferred embodiment, $R^{41}$ and $R^{42}$, independently of each other, are a 1-alkylalkyl, for example 1-ethylpropyl, 1-propylbutyl, 1-butylpentyl, 1-pentylhexyl or 1-hexylheptyl. In another preferred embodiment, $R^{41}$ and $R^{42}$ are each 2,4-di (tert-butyl)phenyl 2,6-diisopropylphenyl or 2,6-di(tert-butyl)phenyl. A preferred compound of formula (IV) is N,N'-bis(2,6-diisopropylphenyl)-3,4,9,10-perylenetetracarboxylic diimide (CAS-number: 82953-57-9).

Organic Fluorescent Dye (B3)

Compounds of formula (V) are subject matter of WO 2017/121833. Compounds of formula (V) are usually orange or red fluorescent dyes. Preference is given to compounds of formula (V), where $R^{51}$ and $R^{52}$ are, independently of each other, selected from the group consisting of phenyl which is unsubstituted or substituted by 1, 2 or 3 $C_1$-$C_6$-alkyl; and $R^{53}$, $R^{54}$, $R^{55}$, $R^{56}$, $R^{57}$, $R^{58}$, $R^{59}$, $R^{510}$, $R^{511}$, $R^{512}$, $R^{513}$, $R^{514}$, $R^{515}$, $R^{516}$, $R^{517}$ and $R^{518}$ are each hydrogen. The compound of formula (V) as defined above is preferably the compound of formula (V.1)

(V.1)

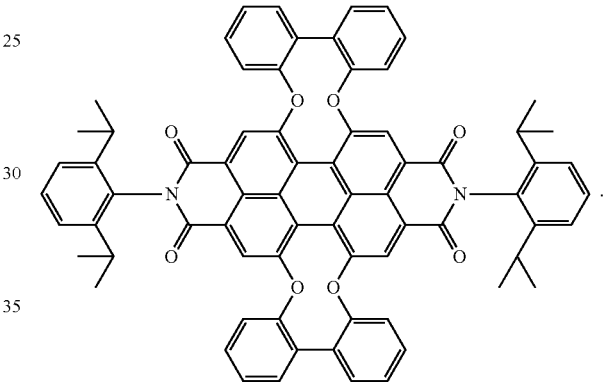

Organic Fluorescent Dye (B4)

Cyanated naphthoylbenzimidazole compounds of formula (VI) are known from WO 2015/019270.

Examples of compounds of formula (VI) are the compounds (VI-1)

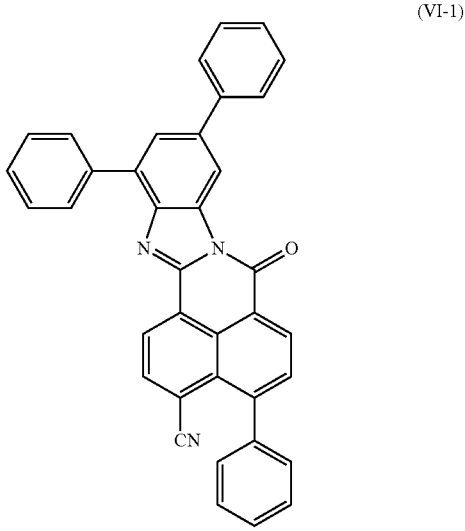

(VI-2)
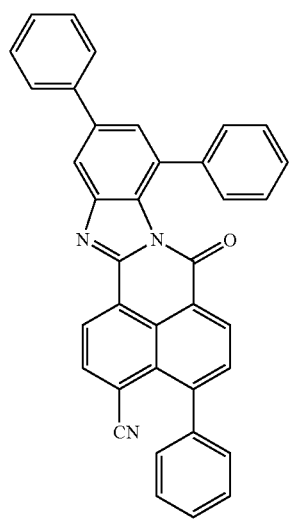
(VI-3)
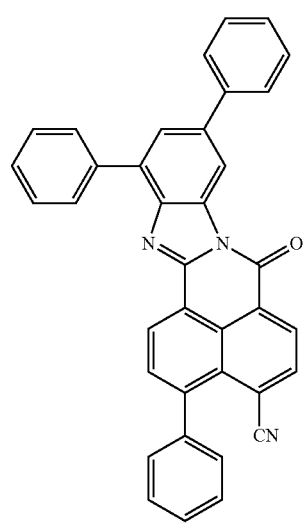
(VI-4)
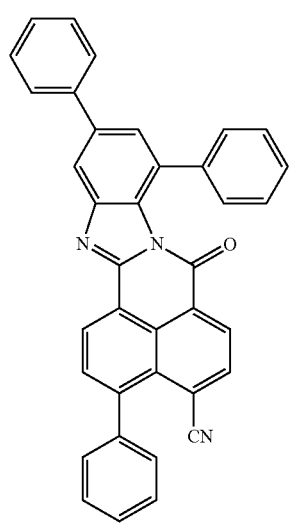
(VI-5)
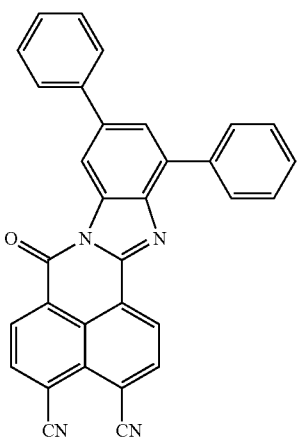
(VI-6)
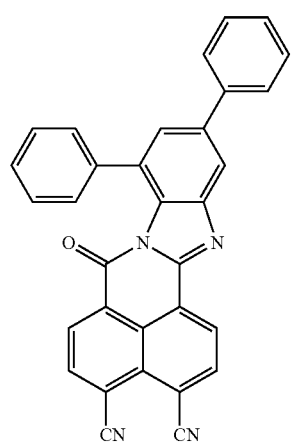
(VI-7)
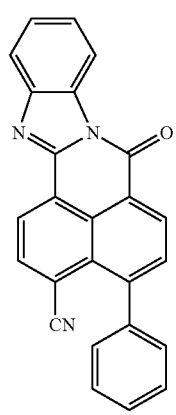

(VI-8)
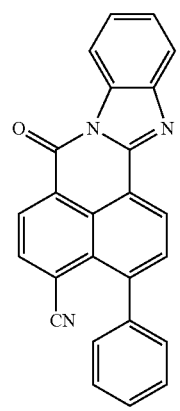
(VI-9)
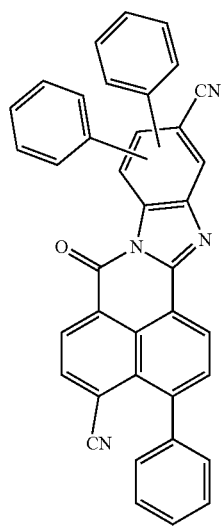
(VI-10)
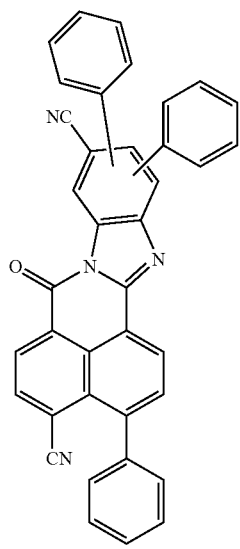
(VI-11)
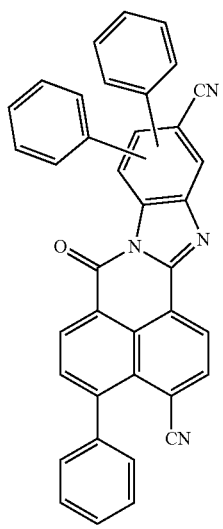
(VI-12)
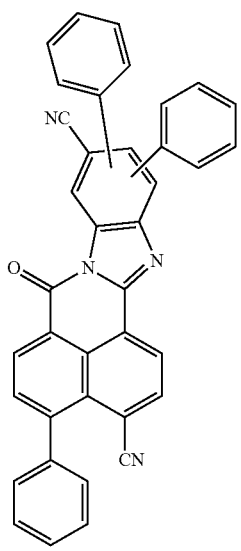
(VI-13)
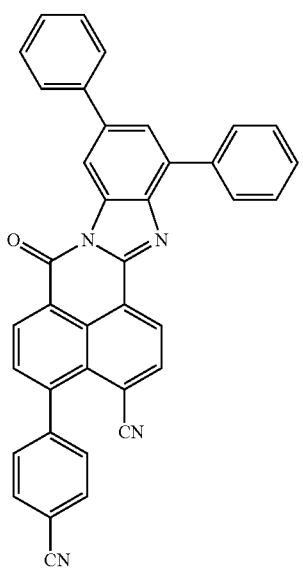

(VI-14)
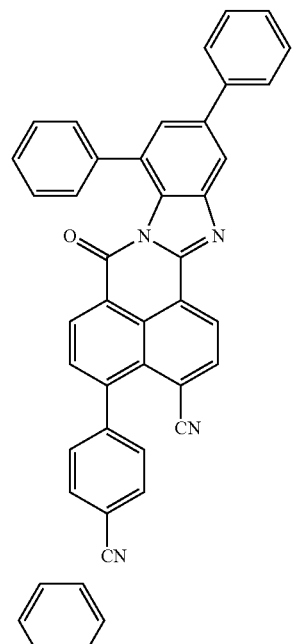
(VI-15)
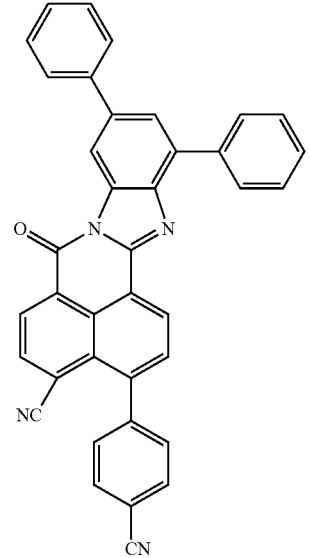
(VI-16)
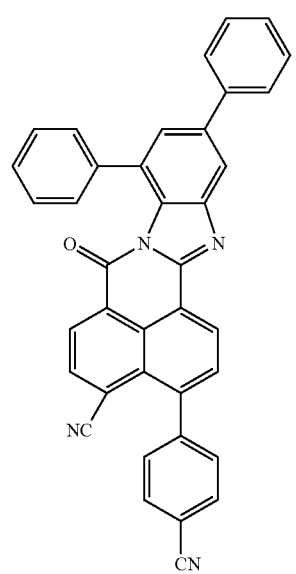
(VI-17)
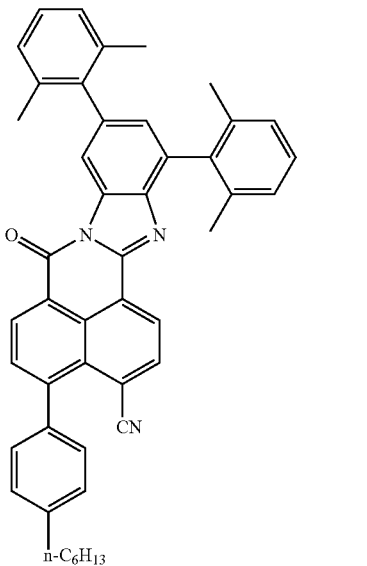
(VI-18)
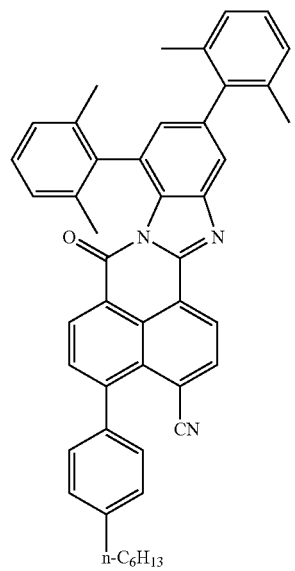

-continued (VI-19)

(VI-20)

(VI-21)

(VI-22)

(VI-23)

(VI-24)

(VI-25) 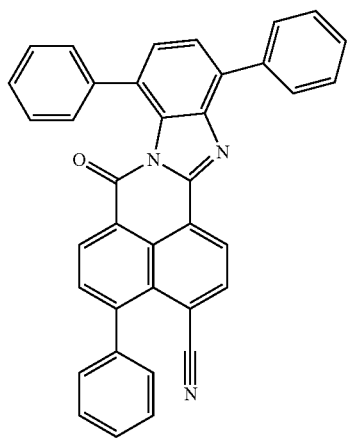
(VI-26) 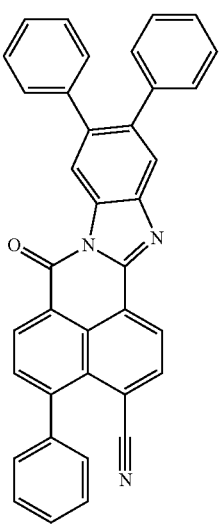
(VI-27) 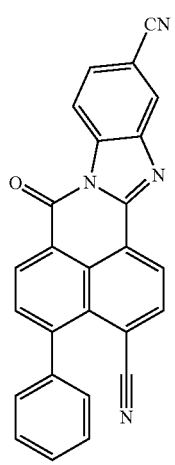
(VI-28) 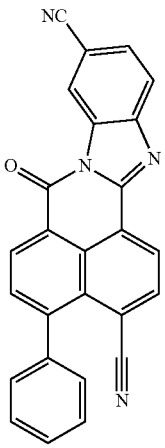
(VI-29) 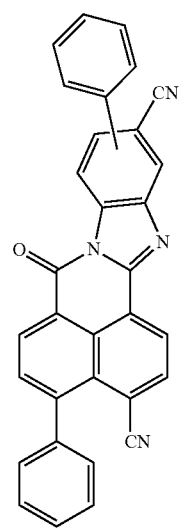
(VI-30) 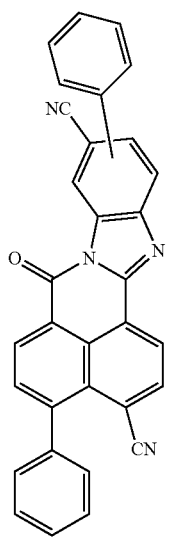
Especially suitable compounds of formula (VI) are those, wherein one of $R^{63}$ or $R^{64}$ is cyano and the other radical $R^{63}$ or $R^{64}$ is phenyl, 4-cyanophenyl and phenyl which carries 1, 2 or 3 substituents selected from the group consisting of $C_1$-$C_{10}$-alkyl. Likewise, especially suitable compounds of formula (VI) are those, where two of the radicals $R^{67}$, $R^{68}$, $R^{69}$, and $R^{610}$ are phenyl and the other two radicals $R^{67}$, $R^{68}$, $R^{69}$ and $R^{610}$ are hydrogen. Among these, more preferred are the compounds VI-1, VI-2, VI-3, VI-4 and mixtures thereof, especially the compound VI-1. Likewise more preferred are the compounds VI-13, VI-14, VI-15, VI-16 and mixtures thereof, especially the compound VI-13.

According to a preferred embodiment, the color converter comprises 1 or 2 organic fluorescent dyes B as defined above, each dye generating a different color such that the mixed light generates white light having a specific color temperature, average color rendering index, and/or R9 value. Especially, the color converter additionally comprises 2 organic fluorescent dyes B. In a specific embodiment, the color converter comprises a compound of formula (I), a compound of formula (III) and a compound of formula (IV). In a further specific embodiment, the color converter comprises a compound of formula (I), a compound of formula (III) and a compound of formula (VI).

The concentration of the compound of formula (I) and the organic fluorescent dye(s) B as defined above in the polymer matrix is set as a function of the thickness of the color converter and the type of polymer. If a thin polymer layer is used, the concentration of the organic fluorescent dye(s) is generally higher than in the case of a thick polymer layer. Typically, the total amount of organic fluorescent dye(s) B in the polymer also depends on the intended use. A skilled person will appreciate that by increasing the concentration of yellow fluorescent dye(s) and red fluorescent dye(s), the light emitted from the LED is tuned to longer wavelength to obtain white light with a low CCT.

Typically, for use in general lighting applications, if at least one dye B is present, the total amount of dye B is in the range from 0.0001 to 0.5% by weight, preferably 0.001 to 0.1% by weight, based on the amount of polymer used. The ratio of compound of formula (I) to the total amount of dye (B) present in the color converter is typically in the range from 1:1 to 20:1, preferably 2:1 to 15:1, more preferably 2:1 to 10:1, such as 2:1 to 6:1. A skilled person will readily appreciate that the ratio of the dyes depends on the chosen light source and the desired correlated color temperature. For a desired CCT, the ratio of compound of formula (I)/dye B is much greater, if the light is generated by a blue LED with a center wavelength of emission between 400 nm and 480 nm in comparison to the ratio of the compound of formula (I)/dye B if the light is generated by a white LED having a CCT between 3 000 to 20 000 K.

Typically, for use in display devices, especially for enhancing color gamut by the compound of formula (I), the color converter comprises at least one dye B. The compound of formula (I) needs to be present in relatively higher content than the at least one dye B. According to another embodiment of the present invention, the total amount of the at least one fluorescent dye B may be 0.002 to 0.8%, preferably 0.003 to 0.6% by weight, based on the amount of polymer used.

According to a further embodiment, the color converter according to the present invention may optionally or alternatively comprise as further fluorescent material at least one inorganic fluorescent material. The at least one inorganic fluorescent material is preferably selected from the group consisting of garnets, silicates, sulfides, nitrides and oxynitrides.

Suitable examples of garnets, silicates, sulfides, nitrides and oxynitrides are compiled in table I below:

TABLE I

| Class | Compounds | Excitation Peak [nm] | Emission Peak [nm] | Reference |
|---|---|---|---|---|
| Garnets | YAG:Ce ($Y_3Al_5O_{12}$:Ce) (Y, Gd, Tb, Lu)$_3Al_5O_{12}$:Ce | 460-470 | 550 | U.S. Pat. No. 5,998,925 |
|  | TAG:Ce ($Tb_3Al_5O_{12}$:Ce) | 460-470 | 575 | U.S. Pat. No. 6,669,866, U.S. Pat. No. 6,812,500, U.S. Pat. No. 6,576,930, U.S. Pat. No. 6,0060,861, U.S. Pat. No. 6,245,259, U.S. Pat. No. 6,765,237 |
| Silicates | Eu-doped Silicates $A_2Si(OD)_4$:Eu with A = Sr, Ba, Ca, Mg, Zn and D = F, Cl, S, N, Br $(SrBaCa)_2SiO_4$:Eu | <460 | 510 to 610 | U.S. Pat. No. 7,311,858, U.S. Pat. No. 7,267,787 U.S. Pat. No. 6,809,347, |
|  | $Sr_3SiO_5$ $Ba_2MgSi_2O_7$:$Eu^{2+}$; $Ba_2SiO_4$:$Eu^{2+}$ $(Ca, Ce)_3(Sc, Mg)_2Si_3O_{12}$ |  |  | U.S. Pat. No. 6,943,380 U.S. Pat. No. 6,429,583 WO 02/11214 |
| Sulfides | (Ca, Sr)S:Eu | <460 | 615-660 |  |
| Nitrides | (CaAlSiN$_3$:Eu$^2$) (Sr, Ca)AlSiN$_3$:$Eu^{2+}$ | 455 | red orange | WO2005052087 |
| Oxy-nitrides | SiAlON:Ce ß-SiAlON:Eu Ca-alpha-SiAlON:Eu $(Ba_3Si_6O_{12}N_2$:Eu) General formula $Ca_xEu_y(Si, Al)_{12}(O, N)_{16}$ | 300-580 | 490 540 585-595 |  |

According to a further embodiment, the inventive color converter comprises at least one quantum dot. Quantum dots are nanocrystals of a semiconductor material having a diameter of about 20 nm or less. The quantum dot may include one of a Si-based nanocrystal, a group II-VI compound semiconductor nanocrystal, a group III-V compound semiconductor nanocrystal, a group IV-VI compound nanocrystal and a mixture thereof. The group II-VI compound semiconductor nanocrystal may include one selected from a group consisting of CdS, CdSe, CdTe, ZnS, ZnSe, ZnTe, HgS, HgSe, HgTe, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HggZnTe, CdZnSeS, CdZnSeTe, CdZnSTe, CdHgSeS, CdHgSeTe, CdHgSTe, HgZnSeS, HgZnSeTe and HgZnSTe. The group III-V compound semiconductor nanocrystal may include one selected from a group consisting of GaN, GaP, GaAs, AlN, AlP, AlAs, InN, InP, InAs, GaNP, GaNAs, GaPAs, AlNP, AlNAs, AlPAs, InNP, InNAs, InPAs, GaAlNP, GaAlNAs, GaAlPAs, GaInNP, GaInNAs, GaInPAs, InAlNP, InAlNAs, and InAlPAs. The IV-VI compound semiconductor nano crystal may be SnTe.

To synthesize a nanocrystal in form of a quantum dot, quantum dots may be prepared by vapor deposition such as metal organic chemical vapor deposition or molecular beam epitaxy, or by a wet chemical process in which a crystal is grown by adding one or more precursors into an organic solvent.

In a more preferred embodiment of the invention, the inventive color converter does not comprise quantum dots. Likewise, in a more preferred embodiment of the invention, the inventive color converter does not comprise inorganic fluorescent materials.

In one embodiment of the invention, inventive color converters have a laminate structure. They may either have a monolayer structure or a multilayer structure, generally composed of a plurality of polymer layers comprising one or more fluorescent colorants and/or scattering bodies. If the color converter has a multilayer structure, one layer comprises the fluorescent colorant according to the invention and another layer comprises at least one fluorescent colorant encompassed by the present invention.

In one embodiment, the at least one compound of formula (I) is present in the layer of the color converter facing the LED. In another embodiment, the at least one further fluorescent colorant/dye is present in the layer of the color converter facing the LED.

If the inventive color converters comprise at least one further organic fluorescent colorant/dye, it is possible in one embodiment of the invention for a plurality of fluorescent colorant/dyes to be present alongside one another in one layer. In another embodiment, the various fluorescent colorant/dyes are present in various layers.

In a specific embodiment, at least one of the layers or matrices comprising organic fluorescent colorant/dyes comprises scattering bodies for light.

In a special embodiment, the color converter has a multilayer structure, preferably a two-layer structure, wherein each layer comprises at least one organic fluorescent colorant/dye. In this embodiment, one of the layers or more than one but not all of the layers or all of the layers comprise a scattering body, preferably $TiO_2$.

In one embodiment, the color converters consist of a plurality of polymer layers which have been laminated together to form a composite and wherein the various fluorescent colorant/dyes and/or scattering bodies may be present in different polymer layers.

In a further embodiment, at least one polymer layer of the color converter has been mechanically reinforced with glass fibers.

Suitable color converters may be in any desired geometric arrangement. The color converters may, for example, be in the form of films, sheets or plaques. Equally, the matrix containing organic fluorescent dyes may be in droplet form or hemispherical form or in the form of lenses with convex and/or concave, flat or spherical surfaces.

"Casting" refers to the embodiment where LEDs or components comprising LEDs are fully cast or enveloped with a polymer comprising organic fluorescent dye. In one embodiment of the invention, the polymer layers (matrices) comprising at least one organic fluorescent dye are 25 to 1000 micrometers (μm) thick, preferably 35 to 400 μm and particularly 50 to 300 μm.

In another embodiment, the polymer layers comprising organic fluorescent dyes are 0.2 to 5 millimeters thick, preferably 0.3 to 3 mm and more preferably 0.4 to 1 mm.

If the color converters consist of one layer or they have a laminate structure, the individual layers, in a preferred embodiment, are continuous and do not have any holes or interruptions.

Inventive color converters may optionally comprise further constituents, such as a backing layer.

Backing layers serve to impart mechanical stability to the color converter. The type of material for the backing layers is not crucial, provided that it is transparent and has the desired mechanical strength. Suitable materials for backing layers are, for example, glass or transparent rigid organic polymers, such as polycarbonate, polystyrene or polymethacrylates or polymethyl methacrylates or polyethylene terephthalate.

Backing layers generally have a thickness of 0.1 mm to 10 mm, preferably 0.2 mm to 5 mm, more preferably 0.3 mm to 2 mm.

In one embodiment of the invention, inventive color converters have at least one barrier layer against oxygen and/or water, as disclosed in WO 2012/152812. Examples of suitable barrier materials for barrier layers are, for example, glass, quartz, metal oxides, $SiO_2$, a multilayer system composed of alternating layers of $Al_2O_3$ and $SiO_2$ layers, titanium nitride, $SiO_2$/metal oxide multilayer materials, polyvinyl alcohol, polyacrylonitrile, polyvinylidene chloride (PVDC), liquid crystal polymers (LCP), polystyrene-acrylonitrile (SAN), polybutylene terephthalate (PBT), polybutylene naphthalate (PBN), polyethylene terephthalate (PET), polyethylene naphthalate (PEN), polyvinyl butyrate (PBT), polyvinyl chloride (PVC), polyamides, polyoxymethylenes, polyimides, polyetherimides, epoxy resins, polymers which derive from ethylene-vinyl acetate (EVA) and polymers which derive from ethylene-vinyl alcohol (EVOH).

A preferred material for barrier layers is glass or a multilayer system composed of alternating layers of $Al_2O_3$ and $SiO_2$ layers. Preferably, suitable barrier layers have low permeability for oxygen. More preferably, suitable barrier layers have low permeability for oxygen and water.

Inventive color converters can be produced by different processes. In one embodiment, the process for producing inventive color converters comprises the dissolution of the at least one polymer and of the at least one organic fluorescent dye in a solvent and subsequent removal of the solvent. In another embodiment, the process for production of inventive color converters comprises the extrusion of the at least one organic fluorescent dye with the at least one polymer. Representative examples of extrudable polymers include polystyrene, polycarbonate, polyethylene terephthalate and polyethylene furanoate. In particular, the extrudable polymer is polyethylene terephthalate.

The color converter can be produced, for example, by extrusion in an extrusion line. The extrusion line usually comprises an extruder as plastification unit, a sheet die as shaping tool, optionally a polishing stack/calender as calibration die, optionally a cooling bed and/or a roller conveyor for aftercooling, optionally a take-off roll and a separating saw.

The method for producing a color converter comprises feeding at least one compound of formula (I) as defined above and at least one extrudable polymer into an extruder, plastifying the feed and extruding the plastified feed through a die, optionally followed by calibrating, smoothing and cooling the sheet or layer in the polishing stack and optionally cutting the sheet to size. Advantageously, the method is carried out in the absence of any added solvents.

It may be advantageous to reduce the water content of polyethylene terephthalate before processing. For example, polyethylene terephthalate is preferably dried at from 130 to 180° C. for 4 to 10 hours before extrusion.

In accordance with the invention, it is possible for the at least one scattering material and optionally further additives as mentioned above, that they are already contained in the extrudable polymer matrix material employed for the extrusion or they are metered into the extruder during production of the layer. For example, light stabilizer may be added via masterbatch technology, where the light stabilizer is fully dispersed in a solid carrier material. Suitable carrier materials are thermoplastics, for example polyethylene terephthalate or other polymers which are sufficiently compatible with the extrudable polymer.

The extrudable polymer such as polyethylene terephthalate is melted in the extruder, i.e. the feed is plastified. It can be advantageous that the extruder possesses multiple separate temperature controllable heating zones. The temperature of the polyethylene terephthalate melt is preferably in the range from 250 to 280° C., it being possible for the temperature of the melt to be adjusted essentially through the temperature of the extruder, heating zone length, the residence time of the melt in the extruder, extruder torque and/or screw rotation speed.

The plastified feed then leaves the extruder through a die. This die is preferably a sheet die.

The color conversion composition plastified in the extruder may be shaped by a sheet die and optionally calibrated, i.e. intensively cooled and smoothed, by smoothing calender rolls.

The extruders employed can be either single-screw, twin-screw, multi-screw extruders or planetary roller extruder. Alternatively, the extruding force may be exerted by a piston or ram (ram extrusion).

The color converter produced by extrusion typically does not contain any added solvent.

Inventive color converters are especially suitable for use in display devices.

Inventive color converters are also especially suitable for the conversion of blue light to white light. More particularly, they are suitable for conversion of light generated by a blue LED with a center wavelength of emission between 400 nm and 480 nm to provide white light. Suitable blue LEDs are, for example, those based on gallium nitride (GaN) or indium gallium nitride (InGaN). They are commercially available.

Inventive color converters are also especially suitable for conversion of light generated by a cool white LED having a correlated color temperature between 3 000 K and 20 000 K to provide white light having a lower correlated color temperature. With regard to suitable white LEDs, reference is made to what is said herein above. White LEDs with a CCT between 3 000 K to 20 000 K are also commercially available.

The color converter according to the invention allows to provide white light at a CCT below 5 000 K, especially equal to or less than 4 500 K or equal to or less than 4 000 K or equal to or less than 3 500 K, with high luminous efficacy, e.g. a luminous efficacy of greater than 230 lumen per watt. Moreover, the color converter according to the invention allows to provide white light below 5 000 K, especially equal to or less than 4 500 K, more especially equal to or less than 4 000 K or equal to or less than 3 500 K with a high average color rendering index CRI Ra of greater than 90. In particular, the white light at a CCT below 5 000 K, especially equal to or less than 4 500 K, more especially equal to or less than 4 000 K or equal to or less than 3 500 K is distinguished by high average color rendering index CRI Ra together with a high R9 value of greater than 60. Preferably, the CRI Ra is at least 92, more preferably at least 95. Preferably, the R9 value is at least 70 and more preferably at least 75.

Likewise possible is their use for conversion of light produced by mercury lamps or by organic light-emitting diodes (OLEDs).

Inventive color converters for use in lighting devices are used in a remote phosphor setup. In this case, the color converter is spatially separated from the LED. In general, the distance between LED and color converter is usually larger than 0.1 mm, such as 0.2 mm or more, and in some embodiments equal to or larger than 0.1 to 10 cm such as 0.3 to 5 cm or 0.5 to 3 cm. Between color converter and LED may be different media such as air, noble gases, nitrogen or other gases or mixtures thereof.

As regards inventive color converters for use in display devices, the distance between LED light source and color converter may range from 0.01 to 20 mm, e.g. 0.01 to 10 mm or 0.01 to 5 mm or as 0.05 to 3.5 mm.

The inventive color converters are additionally suitable for applications as a light-collecting system (fluorescence collector) in photovoltaics and in fluorescence conversion solar cells.

Owing to their short fluorescence decay time, usually in the range from 0.1 to 9 ns, cyanoaryl substituted benz(othi) oxanthene compounds of formula (I) are also of particular interest for use in color converters for data transmission in light fidelity applications comprising a transmitter for transmitting data and for emitting electromagnetic radiation in the visible range.

Accordingly, the present invention also relates to a transmitter for transmitting data and for emitting electromagnetic radiation in the visible spectral range, said transmitter comprising:
  a radiation source for generating and emitting first electromagnetic radiation and
  a modulator being adapted to modulate the first electromagnetic radiation depending on the data to be transmitted generating modulated first electromagnetic radiation, characterized in that the transmitter further comprises
  a color converter for converting at least a part of the modulated first electromagnetic radiation into modulated second electromagnetic radiation, said modulated second electromagnetic radiation being different from the modulated first electromagnetic radiation,
wherein the color converter comprises the compound of formula (I) as defined in above and a polymer matrix.

Many different radiation sources may be used by the transmitter of the present invention. However, according to an embodiment of the present invention, the radiation source is a LED. Furthermore, a laser diode may be used as radiation source. Preferably, the radiation source of the transmitter of the present invention is selected from the group consisting of an UV-LED, a blue LED, a RGB LED system, an organic LED and a cool white LED.

As regards the color converter used in the transmitter, reference is made to what is said herein above. In particular, the distance between the radiation source and the color converter in the range from 0.01 to 10 cm.

Owing to their narrow-band emission in the green spectral range (wavelength range from 490 to 560 nm, especially 490 to 540 nm), compounds of formula (I) are of particular interest for use in display devices such as non-emissive displays and self-emissive displays. Due to their narrow FWHM, compounds of formula (I) significantly increase the color gamut of displays with RGB filters since a part of the blue light is down-converted to longer green wavelengths.

Thus, the present invention further provides a backlight unit for liquid crystal displays (LCD), comprising
(i) at least one of light source;
(ii) at least one color converter as defined above;
wherein the at least one color converter is in a remote phosphor arrangement from the at least one light source.

The light source in a standard LCD backlight unit (BLU) usually is a plurality of light-emitting diodes (LEDs). Preferably, the LED is a blue LED having a center wavelength of emission from 400 nm to 480 nm. Suitable blue LEDs are, for example, those based on gallium nitride (GaN) or indium gallium nitride (InGaN). Likewise preferably, the LED is a white LEDs having a correlated color temperature between 6000 and 12000 K, preferably between 6500 and 11000 K. In particular, the light emitted from the white LED comprises wavelengths in the range from 400 to 700 nm.

The backlight unit can be an edge-lit backlight or a full-array backlight. The edge-lit backlight differs from the full-array backlight in the placement of the light sources. In an edge-lit configuration, the LEDs are assembled at the edge(s) of a rectangular light guide plate, and the light from LEDs undergoes total internal reflections at the inner surface of the light guide plate and finally get extracted through top surface of the light guide plate. The color converter faces the top side of the light guide plate. In full-array backlights, the color converter is arranged above an array of light sources in a remote phosphor arrangement.

According to the invention, the backlight unit comprises at least one color converter comprising a compound of formula (I). The color converter may include further organic fluorescent dyes, especially at least one fluorescent dye B. The further dye(s) may also be excited by the at least one light source. The use of at least one further dye, especially a dye of formula B, is in particular advantageous.

The backlight unit may further include a reflector disposed under the light guide, a lower diffuser disposed on the light guide, a brightness enhancement film and/or a diffuser film.

According to an embodiment of the invention, the color converter does not comprise scattering particles as defined above.

According to a preferred embodiment of the invention, the color converter comprises scattering particles. Suitable scattering particles are those mentioned above silica, alumina, titanium dioxide, zirconia ($ZrO_2$), barium sulfate and zinc oxide. Scattering particles usually have a diameter in the range from 5 to 500 nm.

The color converter usually has a thickness of 2 micrometer to 200 micrometer.

According to the invention, the color converter is physically separated from the light source, i.e. the color converter is in a remote phosphor arrangement from the at least one light source.

The present invention further provides a liquid crystal display device comprising
(i) a liquid crystal panel comprising a thin film transistor (TFT) array, a liquid crystal layer, and a color filter array comprising red, green and blue color filters;
(ii) at least one of light source; and
(III) at least one color converter as defined herein above;
where the at least one color converter is arranged between the at least one light source and the liquid crystal panel or is integrated in the color filter array. For example, the at least one light source and the at least one color converter may be arranged below the liquid crystal panel (direct backlighting). Alternatively, the at least one light source is at the edge and the color converter is a sheet parallel to the LCD (between LCD and waveguide). The edge illumination may occur along the side edges of the LCD, the top edge or the bottom edge. Backlighting may utilize a waveguide to spread the light into an entire LCD panel.

The light source usually is a plurality of light-emitting diodes. Suitable light sources are white light-emitting diodes or blue light emitting diodes as defined above.

When the color converter is arranged below the liquid crystal panel, the at least one color converter and the at least one light source are part of the backlight unit as defined above. The polymer matrix of the color converter is preferably polystyrene or a polystyrene based resin such as the reaction product of a copolymer of styrene, alpha-methylstyrene and acrylic acid; or the polymer matrix of the color converter is preferably a an homo- or copolymeric acrylate and methacrylate, respectively, especially polyacrylate, polymethyl methacrylate or polymethacrylate. In particular, the polymer matrix consists of polycarbonate or consists of polyethylene terephthalate. Specially, the color converter also includes at least one further organic fluorescent dye, especially an organic fluorescent dye B as defined herein above. The color converter may also comprise scattering particles.

The liquid crystal display panel comprises a color filter array, a thin-film transistor (TFT) array opposite to the color filter substrate and a liquid crystal layer.

No matter, whether the liquid crystal display is configured with full array or edge-lit LED light source, the light passes through the liquid crystal layer and the color filter array sequentially.

In a further embodiment, the color converter is integrated in the color filter array. The polymer matrix of the color converter is preferably an epoxy resin or a vinyl ester resin or a photosensitve photoresist composition as described herein above. In this embodiment, the color converter may include further organic fluorescent dyes, especially at least one fluorescent dye B. The further dye(s) may also be excited by the at least one light source. The use of at least one further dye, especially a dye of formula B, is in particular advantageous. The color converter may also comprise scattering particles. According to the embodiment, the light emitted by the at least one light source passes through the liquid crystal layer, and then the color filter array. The color converter according to the invention which is part of the color filter array is positioned between the liquid crystal layer and the red, green, and blue color filters or is contained in the color filter.

The color filter array comprises a plurality of red, green and blue color filters, a red filter for red pixel; a green filter for green pixel and a blue filter for blue pixel. Each of the three color filters is independently operated, and the color of a single pixel is represented by one of the three colors or by a combination of at least two of the three colors. The color filter array usually comprises a light blocking member for defining a matrix of pixel areas. The light blocking member is also referred to as black matrix. The black matrix blocks light that is extraneous to the display that would otherwise emerge on the viewing side of substrate, and thereby reduce the overall contrast.

Color filter arrays can be fabricated by patterning a photosensitive photoresist composition described herein above or by printing. In the patterning method, the patterning is effected by exposing the photosensitive resist composition comprising colorants for the color filters, the at least one compound of formula (I), further organic fluorescent dyes different from compound of formula (I), if present, to light and developing, and the patterning is repeated in sequence in the required times. The compound of formula (I) and organic fluorescent dye(s) different from compound of formula (I), if present, may be present in different resist compositions or in the same resist composition.

The organic fluorescent dye(s) different from compound of formula (I), if present, is preferably selected from the further organic fluorescent dyes B mentioned above. Especially preferred is the further organic fluorescent dye B selected from the group (B1). The further dye(s) may also be excited by the at least one light source. The use of at least one further dye, especially a dye of formula B, is in particular advantageous. The color converter may also comprise scattering particles.

The liquid crystal layer comprises a plurality of liquid crystal molecules. The liquid crystal display device further comprises a pair of polarizers.

The liquid crystal display panel can be a transmissive display panel, a reflective display panel or a transflective display panel.

The liquid crystal display device described above is either a passive matrix one or an active matrix one. The active matrix liquid crystal display comprises an active drive element such as thin film transistor (TFT) or diode in each pixel element.

The active matrix LCD device can be operated according to the twisted-nematic (TN), in plane switching (IPS), vertical alignment (VA) or multi-domain vertical alignment (MVA) technology.

Due to the inventive color converter, less light needs to be filtered out compared to LED backlights of prior art. The LCD according to the invention produces concentrated peaks in the primary wavelengths which can be mixed to create a larger color gamut with more natural, vivid colors.

The liquid crystal display device can be in use as computer monitors, televisions, tablet computers, notebook computers, projectors, smartphones, electronic picture frames, a GPS display, electronic signs, industrial equipment displays, medical device displays, and many other visual display.

A further aspect of the present invention relates to a self-emissive display device comprising
(i) at least one light source;
(ii) at least one color converter as defined above; and
(iii) optional a color filter array comprising red, green and blue color filters.

According to the invention, the at least one color converter is disposed between the at least one light source and the color filter array. In this embodiment, the color converter is arranged above the light source and below the color filter array. Likewise according to the invention, the at least one color converter is integrated in the color filter array.

The polymer matrix of the color converter is preferably an epoxy resin or a vinyl ester resin or a photosensitve photoresist composition as described herein above. The compound of formula (I) and organic fluorescent dye(s) different from the compound of formula (I) may be present in different resist compositions.

According to another embodiment, the compound of formula (I) and the organic fluorescent dye(s) different from the compound of formula (I) are present in the same resist composition. In this embodiment, the compound of formula (I) and the fluorescent dye different from the compound of formula (I) are arranged at a distance from each other such that non-radiative transfer of excitation energy, e.g. in the sense of a Förster resonance energy transfer (FRET), from the compound of formula (I) to said organic fluorescent dye different from the compound of formula (I) can occur and the fluorescent dye different from the compound of formula (I) emits a photon at a second wavelength after said transfer of energy. The compound different from the compound of formula (I) usually is an organic fluorescent dye emitting red light in the wavelength range from 580 to 640 nm. According to a special embodiment, the fluorescent dye different from the compound of formula (I) is excited by blue and green light and emits red light.

The color converter may also comprise scattering particles.

Color filter arrays can be fabricated by patterning a photosensitve photoresist composition described herein above or by printing. In the patterning method, the patterning is effected by exposing the photosensitive resist composition comprising colorants for the color filters, the at least one compound of formula (I), further organic fluorescent dyes different from compound of formula (I), if present, to light and developing, and the patterning is repeated in sequence in the required times. The skilled person will appreciate that the compound of formula (I) and organic fluorescent dye(s) different from compound of formula (I), if present, are present in different resist compositions.

The organic fluorescent dye(s) different from compound of formula (I), if present, is preferably selected from the further organic fluorescent dyes B mentioned above. The further dye(s) may also be excited by the at least one light source. The use of at least one further dye, especially a dye of formula B, is in particular advantageous. The color converter according to the invention which is part of the color filter array is positioned between the light source and the red, green, and blue color filters or is contained in the color filter array.

According to an embodiment of the invention, the light source is a plurality of organic light emitting diodes (OLEDs). An OLED generally includes at least three layers: a cathode layer, a light-emitting layer disposed on the cathode layer, and an anode layer disposed on the light-emitting layer. OLEDs may further comprise functional layers such as an electron transport layer (ETL), a hole transport layer (HTL), an electron barrier layer (EBL) and a hole barrier layer (HBL). According to a specific embodiment, the light source comprises a plurality of red organic light emitting diodes, green organic light emitting diodes, and blue organic light emitting diodes. According to a further specific embodiment, the light source is a white organic light emitting diode. The use of white OLEDs in combination with a color converter according to the invention provides a simpler manufacturing process than an OLED having separately patterned red, green, and blue emitters. Especially suitable are white OLEDs with a pin architecture, i.e., an OLED with a p-doped hole transport layer, an intrinsically conductive emission zone and an n-doped electron transport layer. Examples are phosphorescent white pin OLEDS and fluorescent white pin OLEDs.

White OLEDs (WOLEDs) can have a thin-film multilayer structure, where the simultaneous emission from light from two or more separate emitting layers with different emission colors results in white light. The emitting layers may have a complementary color relationship, i.e. a blue and a yellow emitter layer, or emit the three primary colors of light, namely blue, red and green. Often, the red and green emitters are phosphorescent organic compounds, whereas the blue emitter is an organic fluorescent compound or a yellow phosphorescent organic compound in combination with a blue fluorescent compound. The emissive layers can be horizontally or vertically stacked. For example, a yellow phosphorescent pin-OLED can be stacked on top of a blue fluorescent pin-OLED. Also suitable are WOLEDs with a single emissive layer structure, the layer consisting of a blue emitter doped with different dyes or blending two or more polymers. The WOLED can have a planar bottom-emitting, planar top-emitting, non-planar bottom-emitting, or non-planar top-emitting device structure.

The WOLEDs usually have a correlated color temperature between 6000 to 12000 K, preferably 6500 to 11000 K. In particular, the white light emitted by the WOLED comprises wavelengths in the range from 400 to 700 nm to generate a desired emission spectrum. When the light source is a plurality of OLEDs, especially WOLEDs, the self-emissive display device comprises a color filter array comprising red, green and blue coor filters. Optionally, the color filter array also comprises white pixels. The organic light emitting diode display device may further comprises a black matrix disposed at a boundary between the color filter layers.

According to another preferred embodiment, the light source is a plurality of blue organic light emitting diode, especially a blue OLED with a center of emission between 400 to 480 nm.

According to the driving method of the OLED, OLED panels can be classified into passive matrix organic light emitting diode (PMOLED) panels and active matrix organic light emitting diode (AMOLED) panels. Especially, in some embodiment of the invention, the display is an AMOLED display.

OLED displays can be made by using thermal evaporation and fine-metal masks, by photolithography or by inkjet printing technology.

According to another preferred embodiment, the light source is a plurality of micro LED. A micro-LED has a typical size of hundreds times smaller than the standard LED. For example, each micro LED device may have a maximum width of 1 to 100 µm. In an embodiment the micro LED device comprise a quantum well layer within a p-n diode. The micro LED device can be designed to emit at specific wavelengths in the ultraviolet (UV) or visible spectrum. More preferably, the micro LED emits a blue light and is formed of a semiconductor material such as gallium nitride (GaN), indium gallium nitride (InGaN), or zinc selenide (ZnSe). Usually, the micro LED emits light with a center wavelength of 400 to 480 nm. When the light source is a plurality of micro LEDs, the self-emissive display does not include a color filter array.

The color filter array may additionally comprise white pixels in the array.

The color filter array may additionally comprise a black matrix.

Color filter arrays can be fabricated by patterning a photosensitve photoresist composition described herein above or by printing.

Additionally, in some embodiments, the display may be provided in conjunction with a touch-sensitive element.

The display comprising as light source at least one white OLED or blue LED can be formed on a glass, plastic or silicon substrate.

The OLED display has a faster response, lighter weight, lesser viewing angle restrictions and greater contrast compared with a liquid crystal display. It is especially suitable as display of an electronic paper, an OLED panel, a smart phone, a notebook computer, a tablet, a television set, a digital picture frame or a GPS device.

Micro LED displays are especially suitable for wearable devices such as smart watches and augmented reality glasses and smart phones.

The self-emissive device can be patterned using any patterning techniques, such as shadow masking and photolithography/resist processes. The self-emissive device can also be patterned using inkjet printing technology.

A further aspect of the present invention relates to a lighting device (illumination device) comprising
(i) at least one LED selected from the group consisting of a blue LED with a center wavelength of emission from 400 nm to 480 nm and a white LED having a correlated color temperature between 3 000 K and 20 000 K; and
(ii) at least one color converter as defined herein above,
wherein the at least one color converter is in a remote arrangement from the at least one LED, i.e. the color converter is spatially separated from the LED.

In one embodiment, inventive lighting devices comprise exactly one LED. In another embodiment, inventive lighting devices comprise several LEDs. In one embodiment, inventive lighting devices comprise several LEDs, all of which are blue. In another embodiment, inventive lighting devices comprise several LEDs, at least one LED being blue and at least one LED not being blue, but rather emitting light in another color.

In general, the type of LED used is not crucial for the inventive lighting devices. In a preferred embodiment, the power density of the blue LED light impinging the surface of the converter plate is usually less than 200 mW/cm$^2$, preferably less than 120 mW/cm$^2$, more preferably less than 80 mW/cm$^2$. The use of LEDs of higher power densities, such as 150 or 200 mW/cm$^2$, is likewise possible.

The color converter may, for example, be arranged concentrically around the LED or have a planar geometry. It may take the form, for example, of a plaque, sheet or film, be in droplet form or take the form of a casting.

Inventive lighting devices are suitable for lighting in interiors, outdoors, of offices, of vehicles, in torches, games consoles, streetlights, traffic signs.

Inventive lighting devices exhibit excellent optical performances with a high luminous efficacy. They exhibit warm-tone white light at a CCT below 4000 K, especially below 3500 K, with high average color rendering index of greater 90, preferably at least 92 and especially at least 95; a high R9 value of greater than 60, preferably at least 70 and especially at least 75; together with a high luminous efficacy greater 230 lumen/watt.

The present invention further provides a device producing electric power upon illumination comprising a photovoltaic cell (solar cell) and the color converter as defined herein above, where at least a part of the light not absorbed by the photovoltaic cell (solar cell) is absorbed by the color converter. The color converter is usually on top of the photovoltaic cell. The color converter is used to modify the spectrum such that UV and visible light are converted to a more bathochromic spectrum that is converted at higher efficiency by the solar cell.

The present invention is now illustrated in further detail by the following examples, without imposing any limitation thereto.

EXAMPLES

Abbreviations used: Ex means example; QY means quantum yield; PC means polycarbonate; PET means polyethylene terephthalate; TLC means thin layer chromatography.

I. Preparation of Compound of Formula (I)

Preparation Example 1

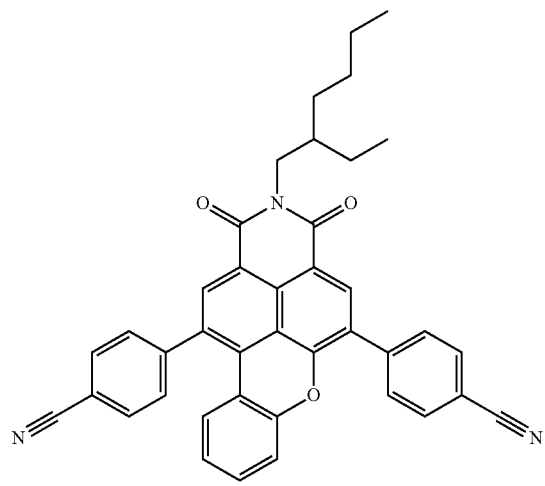 [SMILES: CCCCC(CC)Cn1c(=O)c2cc(-c3ccc(C#N)cc3)c3oc4ccccc4c4c(-c5ccc(C#N)cc5)cc(c1=O)c2c34]

1.1 Preparation of

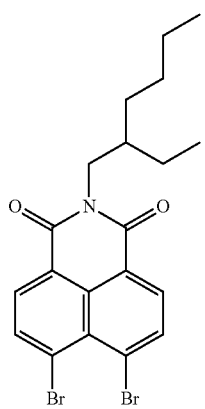 [SMILES: CCCCC(CC)CN1C(=O)c2ccc(Br)c3c(Br)ccc(c23)C1=O]

To a mixture of 5.0 g (14 mmol) of 4,5-dibromonaphthalene-1,8-dianhydride and 100 mL of toluene and 100 mL of ethanol was added 3.7 g (28 mmol) of 2-ethylhexylamine. This mixture was heated to reflux for 2 hours. After reaction was completed solvent was evaporated. The precipitate was collected and recrystallized from a mixture of dichloromethane and ethanol to yield 3.6 g of a slightly yellowish title compound. TLC (Cylohexane/CH$_2$Cl$_2$ 1:2): R$_f$=0.5

1.2

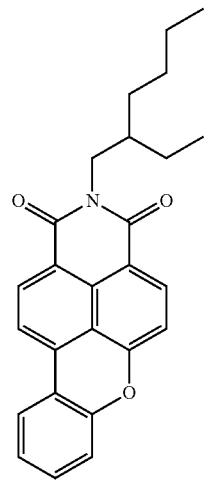 [SMILES: CCCCC(CC)Cn1c(=O)c2ccc3oc4ccccc4c4ccc(c1=O)c2c34]

To a mixture of 7.4 g (16 mmol) of the compound of preparation example 1.1, 290 mL of toluene, 4.4 g (32 mmol) of 2-hydroxyphenylboronoic acid, 4.4 g (32 mmol) of potassium carbonate and 14.5 mL of water were added 7.3 g (0.77 mmol) of Pd(PPh$_3$)$_4$ bound on polystyrene (capacity 0.11 mmol/g). The mixture was heated to 80° C. and stirred for 16 hours. The reaction mixture was cooled to room temperature filtered and the precipitate washed with toluene. The filtrate was evaporated and the residue was recrystallized from a mixture of dichloromethane and methanol. The crude title compound was washed with methanol to yield 5.2 g (82%) of a yellow material.

TLC (cyclohexane/CH$_2$Cl$_2$ 1:2): Rf=0.2

1.3 Preparation of

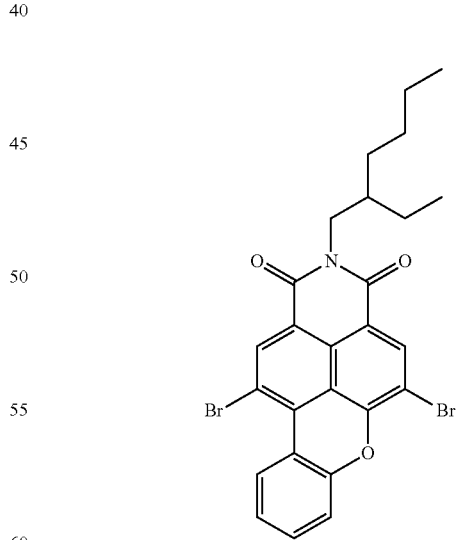

To a solution of 0.62 g (1.6 mmol) of the compound of preparation example 1.2 in 45 mL of chloroform, 2.5 g (15.9 mmol) of bromine were added and the reaction mixture was heated to reflux for 16 hours. Two times bromine (1.9 g 11.7 mmol) was added and the reaction was for continued 24 hours until reaction was completed (control by thin layer chromatography). The reaction mixture was cooled to room temperature, bromine was distilled off and the residual solution was worked up using an aqueous solution of $Na_2S_2O_3$ and dichloromethane. 455 mg (52%) of a yellow compound were obtained.

TLC (toluene/ethyl acetate 10:1): $R_f$ (Product)=0.7.

1.4 Preparation of

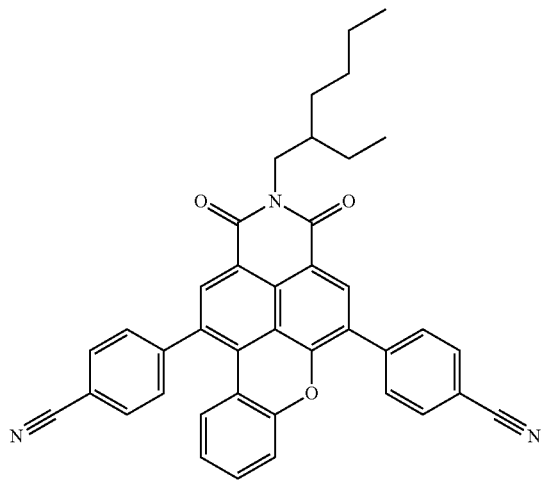 [SMILES: CCCCC(CC)Cn1c(=O)c2cc(-c3ccc(C#N)cc3)c3oc4ccccc4c4c(-c5ccc(C#N)cc5)cc(c1=O)c2c34]

Under an inert argon atmosphere 455 mg of the compound of preparation example 1.3 were dissolved in 10 mL of toluene. 287 mg (2 mmol) of 4-cyanophenylboronic acid and 430 mg (3 mmol) of potassium carbonate were added. 75 mg (0.08 mmol) of tris(dibenzylidenaceton)dipalladium and 66 mg (0.3 mmol) tri-tert.-butylphosphine were added and the mixture heated to 90° C. for 16 hours. The reaction mixture was cooled to room temperature, ca. 2 g of silica was added and the residue was subjected to column chromatography using cyclohexan and dichloromethane. 120 mg (24%) of a yellow compound were obtained.

TLC (cyclohexane/$CH_2Cl_2$ 1:2): $R_f$(Product)=0.2.
Lambda max emission: 508 nm (in polycarbonate)
Lambda max emission: 495 nm (in dichloromethane)

Preparation Example 2: Preparation of

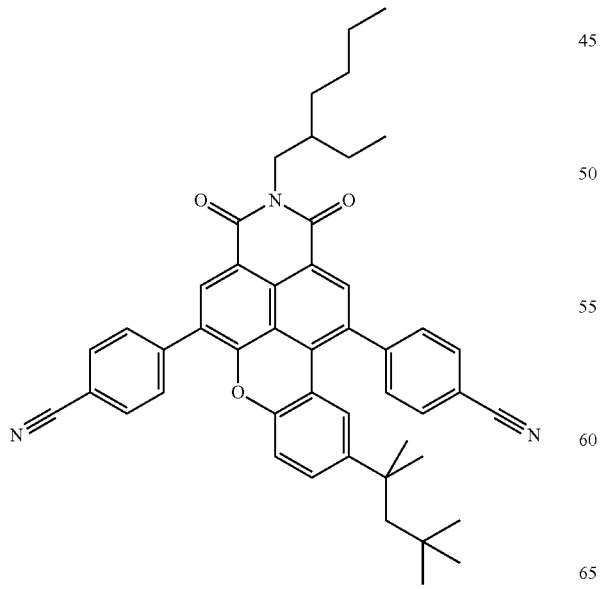

2.1 Preparation of 2-bromo-4-(1,1,3,3-tetramethylbutyl)phenol

A mixture of 10.3 g (50 mmol) of p-tert.-octylphenole and 40 mL of water was heated to 70° C. while being stirred. To this mixture were added 6.8 g (2.2 ml, 43 mmol)) of bromine together with 5 ml of water via a dropping funnel. After the addition was completed the mixture was stirred for another 60 minutes, further 3.1 g (20 mmol) of bromine were added. After one hour the mixture was cooled to room temperature and made alkaline by the addition of NaOH. The crude title compound was extracted with ethyl acetate, washed with water, dried and evaporated under reduced pressure. Finally purification by column chromatography was carried out using cyclohexane and toluene as eluent to yield 17.5 g (quant.) of oily product.

Rf (toluene:petroleum ether=1:1)=0.37

2.2 4-(1,1,3,3-Tetramethylbutyl)-2-(4,4,5,5-tetramethyl-1,3,2-dioxaborolan-2-yl)phenol A mixture of 1.0 g (3.5 mmol) of the compound of preparation example 2.1, 50 mL of toluene, 2.67 g (10.5 mmol) of bis-pinacolatodiboron, 2.7 g of potassium acetate and 0.256 g (0.35 mmol) of 1,1'-bis(diphenylphosphino)ferrocene-palladium(II)dichloride was heated to 70° C. for 22 hours. The reaction mixture was cooled to room temperature, diluted with 50 mL of toluene and 1 g of charcoal was added. The mixture was stirred for 10 minutes and then filtered and the solvent evaporated under vacuum. The product was purified by column chromatography resulting in 1.3 g (83%) of title compound containing 25% of tert.-octylphenole.

Rf (toluene)=0.15.

2.3 Preparation of

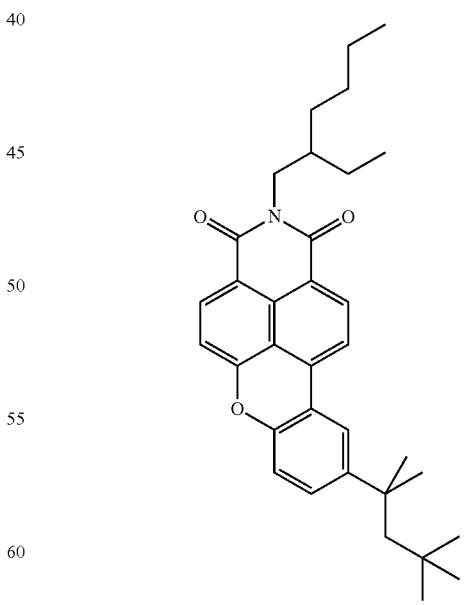

A mixture of 0.62 g (1.33 mmol) of the compound of preparation example 1.1, 10 mL of toluene, 0.37 g of $K_2CO_3$ dissolved in 1 mL of water, 0.885 g of 4-(1,1,3,3-tetramethyl-butyl)-2-(4,4,5,5-tetramethyl-1,3,2-dioxaborolan-2- yl)phenol and 0.6 g of tetrakistri-phenylphosphinepalladium on polystyrene (0.11 mmol/g, Biotage) was heated to 80° C. over night. The mixture was cooled to room temperature and purified by column chromatography using toluene:petroleum ether 10:1. 0.4 g (59%) of a yellow material were obtained which contained traces of p-tert-octylphenol.

Rf (toluene:petroleum ether 10:1)=0.77

2.4 Preparation of

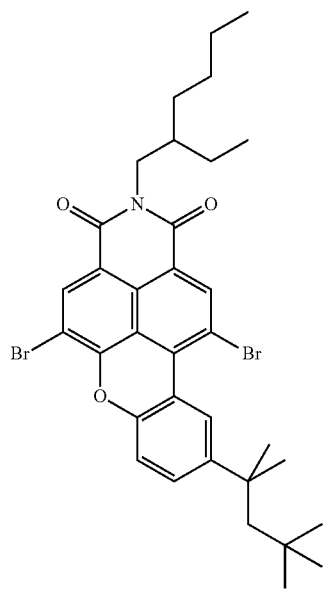 [SMILES: CCCCC(CC)Cn1c(=O)c2cc(Br)c3oc4ccc(C(C)(C)CC(C)(C)C)cc4c4c(Br)cc(c1=O)c2c34]

To a mixture of 10 mL of $CHCl_3$ and 0.3 g (0.6 mmol) of the compound of preparation example 2.3 and 1.0 g (0.34 ml, 6 mmol) of bromine were added. The mixture was heated to 50° C. for 1.5 hours. Bromine and $CHCl_3$ were evaporated and 0.39 g (quant) of a yellow oil were obtained. The product was used without further purification in the next step.

Rf (toluene:ethyl acetate=10:1)=0.91.

2.5 Preparation of

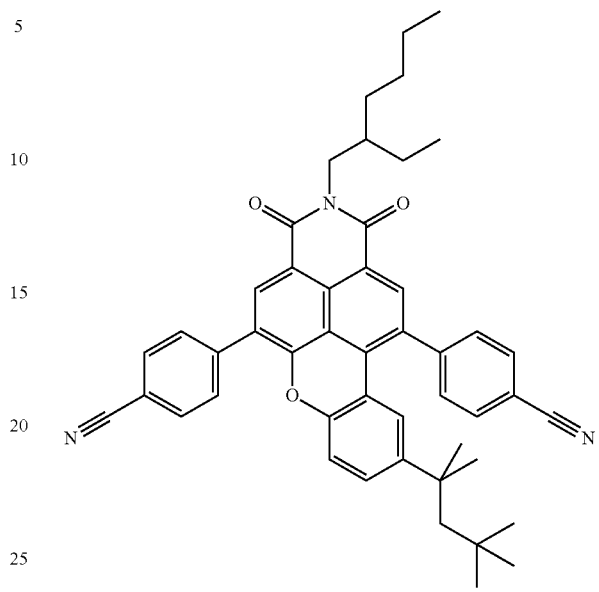

0.39 g (5.8 mmol) of compound of preparation example 2.4 in 10 mL of toluene, 0.188 g of 4-cyanophenylboronic acid (12.8 mmol), 0.18 g (12.8 mmol) $K_2CO_3$ dissolved in 50 mL of water, 0.053 g (0.058 mmol) of tris(dibenzylideneacetone)-dipalladium, 0.23 ml (0.23 mmol) of tri tert-butylphosphine dissolved in toluene (1.0 mol/L) were heated to 90° C. After 2 hours further 0.188 g (1.28 mmol) of 4-cyanophenylboronic acid were added. This procedure was repeated after one additional hour, together with the same amount of catalyst and ligand. After 5 hours the reaction was stopped, the reaction mixture cooled to room temperature and the product isolated by column chromatography using toluene and ethyl acetate as eluent. 62 mg (15%) of product were isolated.

Rf (toluene:ethyl acetate=10:1)=0.47
Lambda max emission: 513 nm (in polycarbonate)
Lambda max emission: 500 nm (in dichloromethane)

Example 3

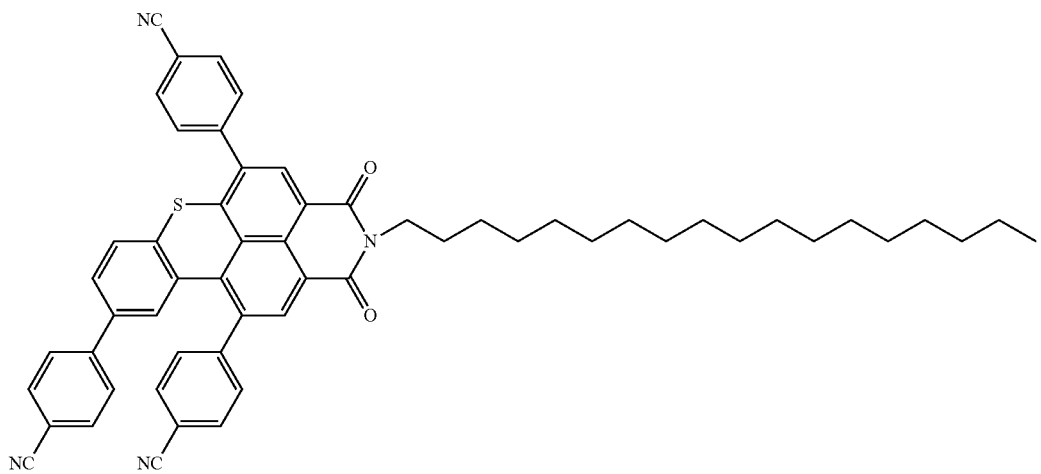 [SMILES: CCCCCCCCCCCCCCCCCCn1c(=O)c2cc(-c3ccc(C#N)cc3)c3sc4ccc(-c5ccc(C#N)cc5)cc4c4c(-c5ccc(C#N)cc5)cc(c1=O)c2c34]

A mixture of 20 mL of toluene, 3.0 g (3.79 mmol) of compound from example 2.3 of WO 2016/151068 depicted below

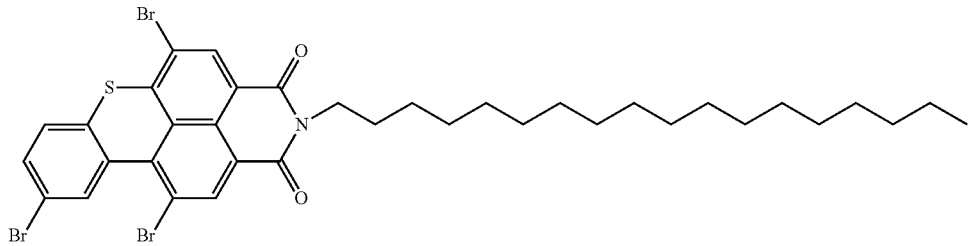

compound from example 2.3 of WO 2016/151068

1.83 g of 4-cyanophenylboronic acid, 1.0 g of $K_2CO_3$ dissolved in 10 mL of water and 0.18 g (0.197 mmol) of tris(dibenzylidenacetone)dipalladium and 0.75 mL (0.75 mmol) 1 mol/l tri-tert-butylphosphine solution in toluene was heated for 3 hours to 90° C. The reaction mixture was cooled to room temperature and 0.5 g of charcoal and 20 mL of toluene were added. The mixture was stirred filtered and the toluene evaporated to almost completion before crystallization started. 30 mL of methanol were added and the resulting residue was filtered, washed with methanol and water and dried under vacuum. The product was purified by column chromatography using toluene ethyl acetate 40:1 2.59 g (80%) of a yellow product were isolated.

Rf (toluene ethyl acetate=10:1)=0.83
Lambda max emission: 548 nm (in polycarbonate)
Lambda max emission: 542 nm (in dichloromethane)

Preparation Example 4

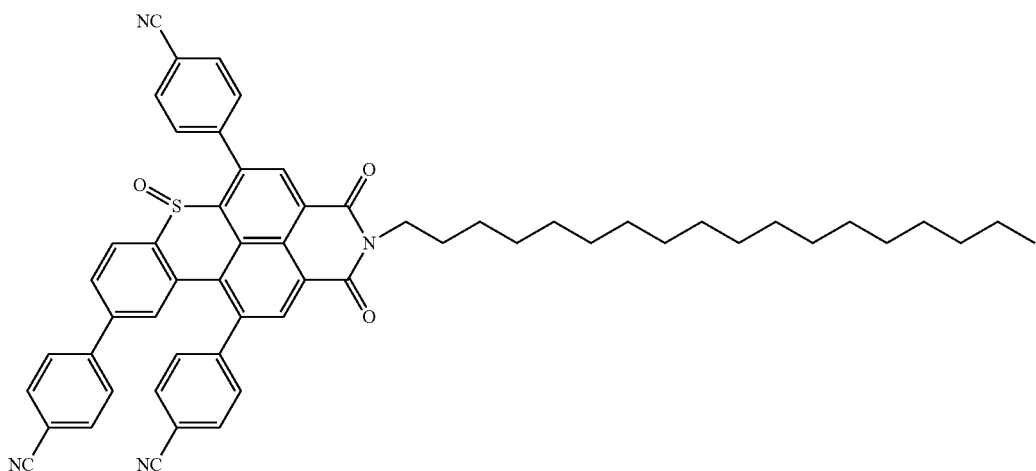 [SMILES: CCCCCCCCCCCCCCCCCCN1C(=O)c2cc(-c3ccc(C#N)cc3)c3c4c(c(-c5ccc(C#N)cc5)cc(c24)C1=O)S(=O)c1ccc(-c2ccc(C#N)cc2)cc1-3]

A mixture of 326.5 mg (0.38 mmol) of the compound prepared in preparation example 3, 78.7 g (0.46 mmol) of 3-chloroperoxybenzoic acid in 60 mL of dichloromethane was stirred at 25° C. for 24 hours. Another 8.5 mg (0.05 mmol) of 3-chloroperoxybenzoic acid were added and 4 hours kept at room temperature. The resulting solution was extracted twice with 5% NaOH solution and the organic phase was dried with MgSO4 and the solvent evaporated. The residue was purified by column chromatography using toluene ethyl acetate. 257 mg (77%) of a yellow solid could be obtained.

Rf (toluene: ethyl acetate 10:1)=0.1
Lambda max emission: 527 nm (in polycarbonate)
Lambda max emission: 551 nm (in dichloromethane)

Example 5

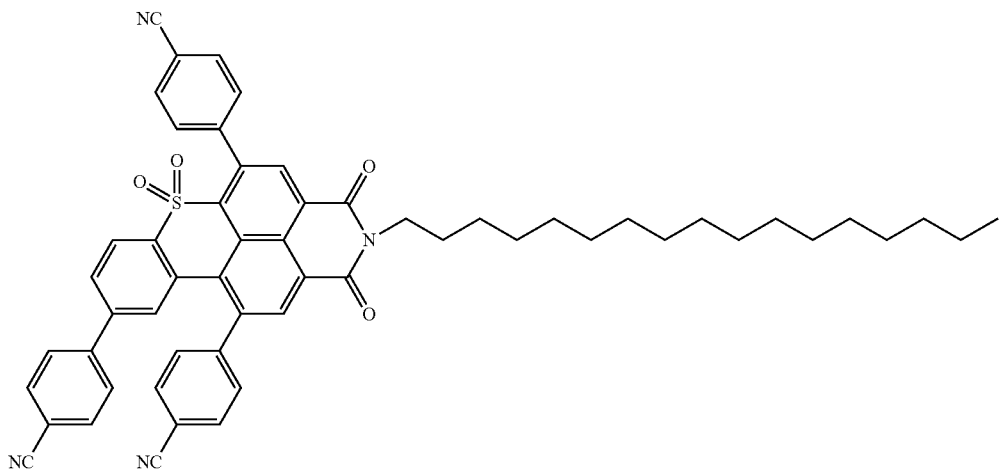 [SMILES: CCCCCCCCCCCCCCCCCN1C(=O)c2cc(-c3ccc(C#N)cc3)c3c4c(c(-c5ccc(C#N)cc5)cc(c24)C1=O)S(=O)(=O)c1ccc(-c2ccc(C#N)cc2)cc1-3]

A mixture of 300 mg (0.349 mmol) of the compound from preparation example 3, 181 mg (1.05 mmol) of 3-chloroperoxybenzoic acid in 60 mL of dichloromethane was stirred for 6 h at room temperature. Another 78 mg (0.45 mmol) of 3-chloroperoxybenzoic acid was added and the mixture kept for 6 hours at this temperature. The resulting solution was extracted twice with 5% of NaOH solution and the organic phase was dried with MgSO$_4$ and the solvent evaporated. The residue was purified by column chromatography using toluene ethyl acetate. 221 mg (71%) of a yellow solid could be obtained.

Rf (toluene: ethyl acetate 10:1)=0.3
Lambda max emission: 493 nm (in polycarbonate)
Lambda max emission: 493 nm (in dichloromethane)

Preparation Example 6

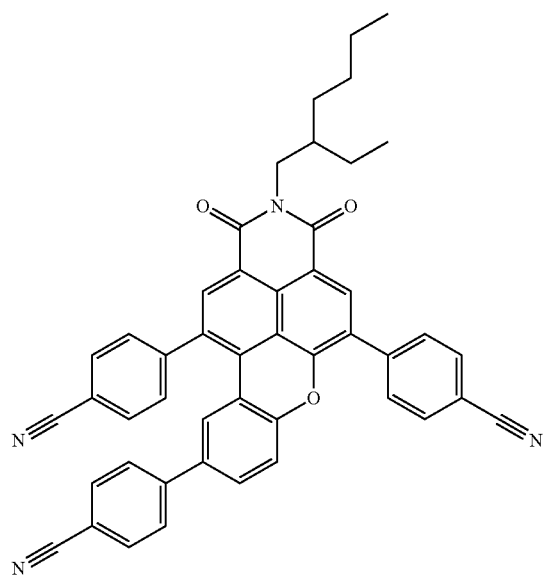 [SMILES: CCCCC(CC)Cn1c(=O)c2cc(-c3ccc(C#N)cc3)c3oc4ccc(-c5ccc(C#N)cc5)cc4c4c(-c5ccc(C#N)cc5)cc(c1=O)c2c34]

6.1 Preparation of

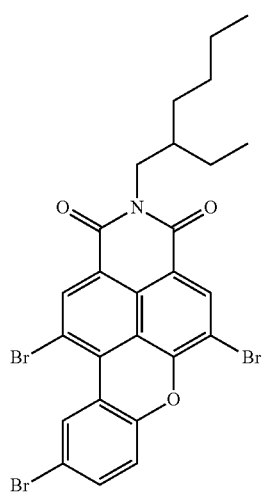 [SMILES: CCCCC(CC)Cn1c(=O)c2cc(Br)c3oc4ccc(Br)cc4c4c(Br)cc(c1=O)c2c34]

To a solution of 11.5 g (28.8 mmol) of the compound of example 1.2 in 150 mL of dichlorobenzene, 25 g (1.59 mmol) of bromine were added and the reaction mixture was heated to 70° C. and kept at this temperature for three hours. The reaction mixture was cooled to room temperature and stirred at this temperature for three days. Bromine was distilled off and the residual solution was worked up using an aqueous solution of Na$_2$S$_2$O$_3$ and dichloromethane. 15.36 g mg (96%) of a yellow compound were obtained.

TLC (toluene/ethyl acetate 10:1): R$_f$(Product)=0.9, (very intense), 0.8 (low intense). According to HPLC the product contains to 75% of dibrominated compound and 25% of tribrominated compound.

6.2 Preparation of

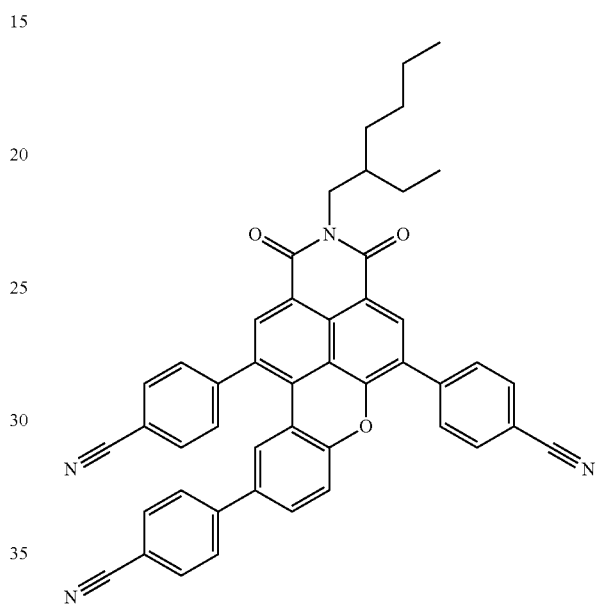

Under an inert argon atmosphere, 14.7 (25.9 mmol) g of the compound of example 6.1 were dissolved in 140 mL of toluene. 8.47 g mg (56.7 mmol) of 4-cyanophenylboronic acid and 7.0 g (52.5 mmol) of potassium carbonate were added. 1.18 g (1.3 mmol) of tris(dibenzylidenaceton)dipalladium and 4.9 mL of 1M (4.9 mmol) tri-tert.-butylphosphine in toluene were added and the mixture heated to 90° C. for 3 hours. The reaction mixture was cooled to room temperature, ca. 2 g of silica were added and the residue was subjected to column chromatography using toluene and ethyl acetate. 600 mg (23) of a yellow trisubstituted compound were obtained and 9.63 g (61%) of disubstituted compound.

TLC (toluene/EtOAc 10:1): R$_f$ (Product)=0.32.
Lambda max emission: 513 nm (in polycarbonate)
Lambda max emission: 498 nm (in dichloromethane)

II. Preparation of Color Converters
Materials Used:
LED 1: cool white LED with CCT of 8595 K
LED 2: blue LED with peak wavelength of 450 nm
Polymer 1: transparent polycarbonate based on a polycondensate of bisphenol A and phosgene (Makrolon® 2805 from Bayer MaterialScience AG).
Polymer 2: polyethylene terephthalate, PET Terez 3200, from TER HELL PLASTIC GmbH.
In the examples, polymers 1 and 2 were used, although comparable data could be achieved with other polymers.
Titanium dioxide: TiO$_2$ rutile pigment: Kronos® 2233— from Kronos Titan Dye 1: Yellow Fluorescent Compound, in the Following Dye 1 (not According to the Invention)

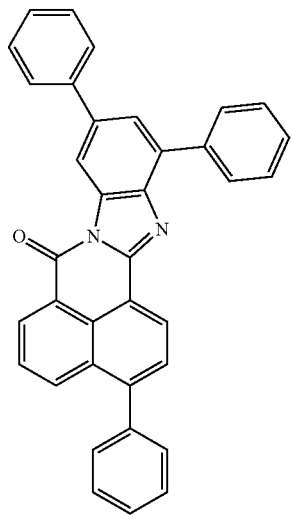
(Dye 1)

obtained as described in example 10 of WO 2012/168395, followed by purification with chromatography. The mixture comprising the compound Dye 1 was subjected to a further column chromatography to give the pure title compound.

Lambda max emission: 536 nm (in polycarbonate).

Dye 2: Compound from Preparation Example 1 According to this Invention, in the Following Dye 2

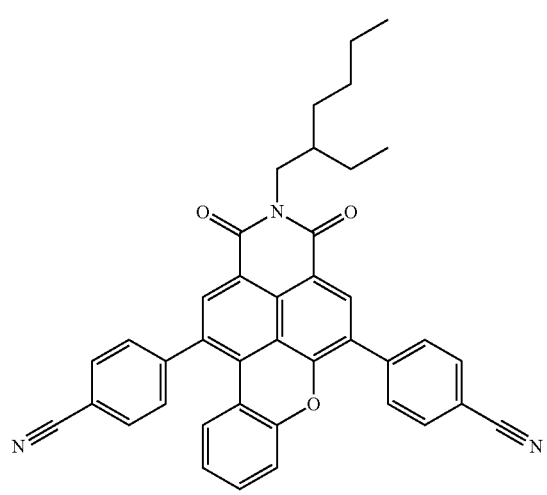
(Dye 2)

Lambda max emission: 508 nm (in polycarbonate).

Dye 3: Fluorescent Compound of Formula (VI-1), in the Following Dye 3

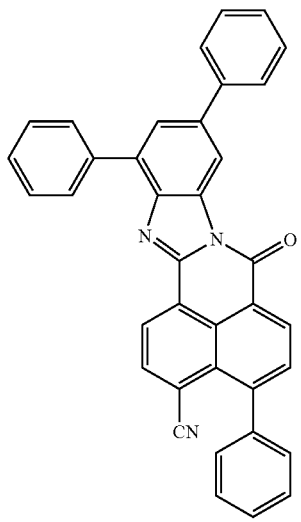
(Dye 3)

corresponding to compound (11) from WO 2015/019270.

Lambda max emission: 552 nm (in polycarbonate).

Dye 4: N,N'-bis(2,6-diisopropylphenyl)-3,4,9,10-perylenetetracarboxylic diimide (CAS-Number: 82953-57-9), in the Following Dye 4

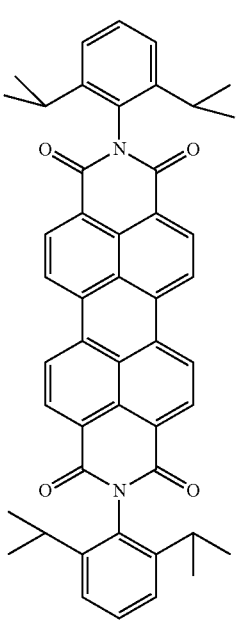
(Dye 4)

Lambda max emission: 548 and 578 nm (in polycarbonate).

The compound is commercially available.

Dye 5: Fluorescent Compound of Formula (V.1), in the Following Dye 5

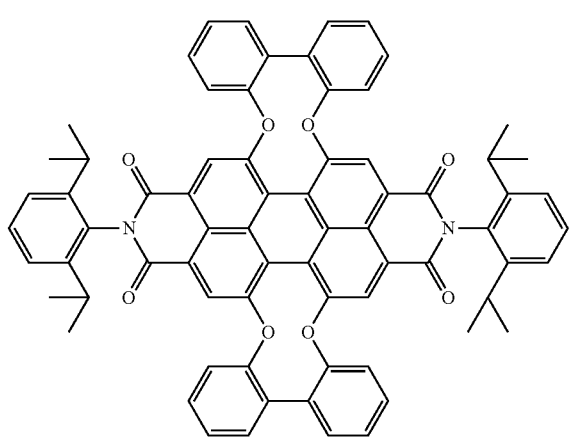
(Dye 5)

The compound of formula (V.1) was prepared as described in example 1 of WO 2017/121833. Lambda max emission: 580 nm (in polycarbonate)

Dye 6: Compound of Formula (III-4), in the Following Dye 6

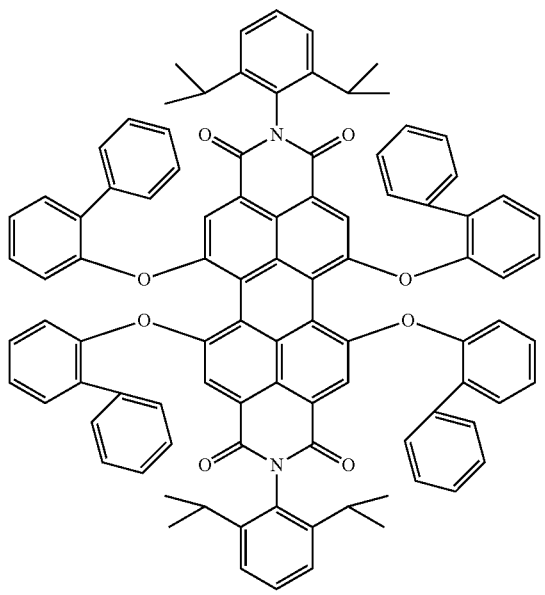
(Dye 6)

prepared as described in example 1 of WO 2018/065502.

A mixture of 5 g (5.9 mmol) of N,N'-(2,6-diisopropylphenyl)-1,6,7,12,-tetrachloro-perylenetetracarboxylic diimide, 4.23 g of (24.9 mmol) biphenyl-2-ol, 138.21 g (16.9 mmol) of potassium carbonate and 30 mL of N-methyl-2-pyrrolidone (NMP) were stirred at room temperature for 24 h and then for 48 h at 115° C. After cooling to 80° C. the reaction mixture was added dropwise to a mixture of 10 mL of acetic acid and 20 mL of water within 15 min, cooled to room temperature over a period of 2 h and then filtered. The residue was washed with 300 mL of a mixture of ethanol/water (1:1) and then with 600 mL of a mixture of ethanol/water/NMP (4:4:1). The residue was dissolved in a mixture of 35 mL of ethanol and 5 mL of NMP under reflux, then cooled to room temperature and separated to obtain 5.6 g (62%) of a red dye which was purified by chromatography using cyclohexane/ethyl acetate. The yield was 2.06 g (23%).

Rf (cylohexane/ethyl acetate 10:1)=0.29. Lambda max emission: 622 nm (in polycarbonate).

Dye 7: Compound of Formula (III-3), in the Following Dye 7

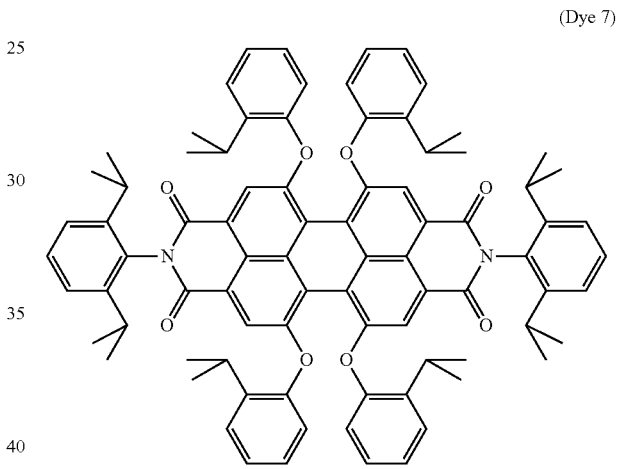
(Dye 7)

The compound of formula (III-3) was prepared as described in WO 2018/134263.

A mixture of 2.2 g (2.6 mmol) of 1,6,7,12-tetrachloro-N,N'-2,6-diisopropylphenyl-perylene-3,4,9,10-tetracarboxylic acid diimide, 4.25 g (31.2 mmol) of 2-isopropylphenol, 2.52 g (18.2 mmol) of $K_2CO_3$ and 170 mL of N-methylpyrrolidone were heated to 90° C. for 17 hours. Afterwards the mixture was heated to 110° C. for 10 hours. Further 2.12 g (15.6 mmol) of 2-isopropylphenol and 1.26 g of $K_2CO_3$ were added and heating continued for 23 hours. Further 2.12 g (15.6 mmol) of 2-isopropylphenol and 1.26 g of $K_2CO_3$ were added and heating continued for 6 hours. The product was precipitated with 1 L of diluted HCl. After extraction with dichloromethane 7.5 g of a liquid crude material was obtained which was further purified by column chromatography using toluene dicholoromethane. 0.28 g of pure title compound were isolated.

Rf (petroleum ether/ethylacetate 8:1)=0.3.

Lambda max emission: 616 nm (in polycarbonate)

Dye 8: Compound of formula (III-2), namely N,N'-bis(2,6-diisopropylphenyl)-1,6,7,12-tetraphenoxyperylene-3,4;9,10-tetracarboxylic acid diimide, in the Following Dye 8

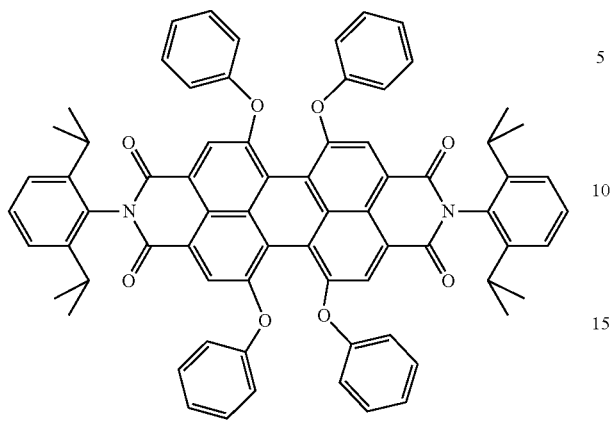

(Dye 8)

commercially available from BASF, Germany.

Lambda max emission: 615 nm (in polycarbonate)

Method for Producing Color Converters:

By Solution Processing

For preparation of the converters the materials, i.e. polycarbonate, dyes and $TiO_2$ (Kronos 2233) were mixed together according to the desired concentrations (see Table II and III). The concentrations are given relative to the amount of polymer polycarbonate used. Then methylene chloride was added and the mixtures were stirred overnight. The solutions/dispersions were coated onto a glass surface using an applicator frame (wet film thickness 800 μm from Ericsen). After the solvent had dried off for 2 hours, the film was detached from the glass and dried in vacuum at 50° C. Samples with defined geometries were cut from the foils, depending on the use of LED 1 or LED 2.

TABLE II

Non-inventive converter mixtures with Dye 1 for white LEDs

| Ex | Yellow dye | Yellow conc.# | Orange dye | Orange conc.# | Red dye | Red conc.# | $TiO_2$ [% by weight] | Film thickness [μm] |
| --- | --- | --- | --- | --- | --- | --- | --- | --- |
| C1 | Dye 1 | 0.03405 | Dye 4 | 0.00176 | Dye 6 | 0.00881 | 0.50 | 152.6 |
| C2 | Dye 1 | 0.0289 | Dye 4 | 0.00133 | Dye 7 | 0.00667 | 0.50 | 150.6 | concentration in % by weight based on the amount of polymer polycarbonate used

TABLE III

Inventive converter mixtures with yellow Dye 2 according to the invention for white LEDs

| Ex | Yellow dye | Yellow conc.# | Orange dye | Orange conc.# | Red dye | Red conc.# | $TiO_2$ conc.# | Film thickness [μm] |
| --- | --- | --- | --- | --- | --- | --- | --- | --- |
| A1 | Dye 2 | 0.0480 | Dye 4 | 0.0022 | Dye 7 | 0.0085 | 0.50 | 147.5 |
| A2 | Dye 2 | 0.0520 | Dye 4 | 0.0024 | Dye 7 | 0.0092 | 0.50 | 150.0 |
| A3 | Dye 2 | 0.0499 | Dye 4 | 0.0023 | Dye 6 | 0.0112 | 0.50 | 147.0 |
| A4 | Dye 2 | 0.0491 | Dye 4 | 0.00236 | Dye 6 | 0.0113 | 0.50 | 148.4 |
| A5 | Dye 2 | 0.0450 | Dye 5 | 0.0022 | Dye 7 | 0.0084 | 0.50 | 147.9 | concentration in % by weight based on the amount of polymer polycarbonate used

Characterization of the Lighting Devices:

LED 1 and LED 2, respectively, were used as light source for pumping the converter film.

The cool-white LEDs 1 were inserted into a transparent plastic tube of T8 format.

Rectangular pieces of the converter films are shaped to semitubes and inserted into the tube. The converter film therefore covers the cool white LEDs.

LED 2: A down-light equipped with blue LEDs (450 nm) inside a mixing chamber are totally covered by a planar, circular platelet of the converter film with 61 mm diameter.

The light irradiated from the surface of these devices was subjected to the photometric measurement, where the total light irradiated from the device was measured by a photometric measurement tool equipped with an integrating sphere, ISP 500-100, and the CCD detector CAS 140CT-156 (from Instrument Systems, Munich). The measured radiance spectrum was used to derive all relevant photometric data such as CCT (=correlated color temperature) in Kelvin [K], distance of color point from Planck-curve (BBL), average color rendering index CRI and color rendering index for reference color no. 9 (R9), efficacy data etc. The results are given in tables Ill and IV and VI.

TABLE IV

Photometric data of non-inventive converters for white LED 1 (for comparison)

| | CIE-x | CIE-y | CIE-u' | CCT [K] | distance from BBL (duv) | average CRI ($R_a$) | R9 |
|---|---|---|---|---|---|---|---|
| LED 1 | 0.2987 | 0.2766 | 0.2088 | 8595 | $-1.80 \cdot 10^{-2}$ | 81.53 | 51.56 |
| C1 | 0.4290 | 0.4020 | 0.2463 | 3122 | $3.27 \cdot 10^{-4}$ | 89.27 | 59.12 |
| C2 | 0.4332 | 0.4016 | 0.2492 | 3044 | $-4.62 \cdot 10^{-4}$ | 88.79 | 43.33 |

TABLE V

Photometric data of inventive converters for white LED 1

| | CIE-x | CIE-y | CIE-u' | CCT [K] | distance from BBL duv | average CRI $R_a$ | R9 |
|---|---|---|---|---|---|---|---|
| LED 1 | 0.2987 | 0.2766 | 0.2088 | 8595 | $-1.80 \cdot 10^{-2}$ | 81.53 | 51.56 |
| A1 | 0.4253 | 0.3984 | 0.2455 | 3158 | $-5.60\text{E}-04$ | 95.28 | 62.45 |
| A2 | 0.4322 | 0.4004 | 0.2491 | 3052 | $-8.00\text{E}-04$ | 95.18 | 63.35 |
| A3 | 0.4282 | 0.4025 | 0.2456 | 3141 | $6.72\text{E}-04$ | 96.06 | 82.55 |
| A4 | 0.4290 | 0.4009 | 0.2468 | 3112 | $-1.11\text{E}-04$ | 95.79 | 79.79 |
| A5 | 0.4272 | 0.3933 | 0.2489 | 3080 | $-2.99\text{E}-03$ | 90.93 | 79.84 |

Non-inventive and inventive converters are described in Tables II and Ill. The photometric data are given in Tables IV and V. The converters create warm-white light having almost similar CIE color coordinates. The inventive color converters exhibit significantly higher values of the average CRI Ra and of R9. Since the orange and red dyes are the same in the comparative examples as in the inventive examples, the improvement of average CRI and R9 can be attributed to the inventive yellow dye 2.

TABLE VI

Converters for blue LED

| Ex | Yellow dye | Yellow conc.# | Orange dye | Orange conc.# | Red dye | Red conc.# | TiO$_2$ conc.# | Film thickness [μm] |
|---|---|---|---|---|---|---|---|---|
| A6 | Dye 2 | 0.19 | Dye 3 | 0.074 | Dye 7 | 0.012 | 0.5 | 145 | concentration in % by weight based on the amount of polymer polycarbonate

TABLE VII

Photometric data of converters for blue LED

| | CIE-x | CIE-y | CIE-u' | CCT [K] | distance from BBL (duv) | average CRI ($R_a$) | R9 |
|---|---|---|---|---|---|---|---|
| LED 2 | 0.1539 | 0.0235 | 0.2069 | — | — | — | — |
| A6 | 0.4859 | 0.4417 | 0.2652 | 2594 | 9.01E−03 | 93.06 | 67.58 |

III. Color Filter and Color Conversion Film

Application Example 1: Preparation of a Green Color Filter

The following substances were introduced into a 37 mL screw bottle;

| 1.34 g | C.I. Pigment Green 58 (FASTOGEN Green A350, available from DIC Corporation Tokyo, Japan) |
| 0.66 g | C.I. Pigment Yellow 138 (Paliotol Yellow, available from BASF SE, Germany) |
| 16.15 g | Propylene glycol 1-monomethyl ether 2-acetate |
| 1.00 g | Dispersant (EFKA 4300, an acrylic block copolymer, available from BASF SE, Germany) |
| 5.85 g | Binder polymer (acrylate resin Ripoxy SPC-2000, available from Showa Denko K.K., Japan) |
| 30.0 g | 0.5 mm zirconia beads |

The bottle was sealed with an inner cup then applied to a paint conditioner for 15 hours to give a dispersion. The dispersion thus obtained was cast onto a glass substrate by means of a spin coating, wherein a layer thickness is adjusted to give a film having a desired color points (by standard C light, observation 2 degree) by controlling rotation speed, then dried at 80° C. for 10 minutes and 230° C. for 30 minutes.

Optical properties of the dispersion films thus obtained was measured by use of a spectrophotometer (UV-2500PC, Shimadzu) and color points (C.I.E. 1931 x, y chromaticity diagram) were calculated using standard C light.

Layer thicknesses of the dispersion films were measured by use of a stylus surface profiler (Dektak 6M, ULVAC Inc.).

Pigment ratio and layer thickness of the samples were adjusted to give x=0.23, y=0.66 by C light which color will achieve to DCI specification (accepted as the standard color for TV system) by white OLED.

TABLE VIII

Optical properties of green dispersion film

| Pigments | Color points by C light | | Y | Film thickness [μm] |
|---|---|---|---|---|
| | x | y | | |
| C.I. Pigment Green 58: 1.34 g | 0.230 | 0.656 | 41.3 | 5.54 |
| C.I. Pigment Yellow 138: 0.66 g | | | | |

Y: brightness

Application Example 2: Preparation of a Color Converter Containing the Compound of Preparation Example 1

The following substances were introduced into a 5 mL screw bottle;

```
  20 mg  compound of preparation example 1 (Dye 2)
1011 mg  Binder polymer (acrylate resin Ripoxy SPC-2000, available
         from Showa Denko K.K., Japan)
 969 mg  Propylene glycol 1-monomethyl ether 2-acetate (PGMEA)
   3 g   0.5 mm zirconia beads
```

The bottle was sealed then applied to a paint conditioner for 30 minutes to give a dye solution. Zirconia beads were filtered out. The dye solution was cast onto a glass substrate by means of a spin coating 400 rpm, then dried at 80° C. for 10 minutes. The layer thickness of the dispersion film was measured by use of a stylus surface profiler (Dektak 6M, ULVAC Inc.). Film thickness: 3.2 μm Application Example 3: Preparation of a Clear Film (for Reference)

The following substances were introduced into a 5 mL screw bottle;

```
1064 mg  Binder polymer (Acrylate resin Ripoxy SPC-2000,
         available from Showa Denko K.K, Japan)
 936 mg  Propylene glycol 1-monomethyl ether 2-acetate (PGMEA)
   3 g   0.5 mm zirconia beads
```

The bottle was sealed and then applied to a paint conditioner for 30 minutes to give a dye solution. Zirconia beads were filtered out. The solution was cast onto a glass substrate by means of a spin coating 400 rpm, then dried at 80° C. for 10 minutes. Layer thicknesses of the dispersion films are measured by use of a stylus surface profiler (Dektak 6M, ULVAC Inc.).
Film thickness: 3.75 μm Application Example 4: Resist Comprising the Compound of Preparation Example 1

All operations were carried out under yellow light. The following substances were introduced into a 5 mL screw bottle:

```
 25 mg  Compound of preparation example 1
819 mg  Binder polymer (Acrylate resin Ripoxy SPC-1000,
        available from Showa Denko K.K, Japan)
238 mg  dipentaerythritol hexaacrylate (DPHA)
919 mg  Propylene glycol 1-monomethyl ether 2-acetate (PGMEA)
  5 mg  photopolymerization initiator Irgacure OXEO1,
        available from BASF Japan Ltd.
  3 mg  0.5 mm zirconia beads
```

The bottle was sealed then applied to a paint conditioner for 30 minutes to give a dye solution. Zirconia beads were filtered out.

The dye solution was cast onto a glass substrate by means of a spin coating 400 rpm, then dried at 80° C. for 10 minutes. Exposure was carried out using a 250 W super high pressure mercury lamp (USH-250BY, USHIO) at distance of 15 cm. A total exposure dose on the glass filter was adjusted to be 300 mJ/cm$^2$ by using an optical power meter (Model UV-M02 with UV-35 detector, ORC UV Light Measure) and then baked at 230° C. for 30 minutes. Layer thicknesses of the dispersion films were measured by use of a stylus surface profiler (Dektak 6M, ULVAC Inc.). Film thickness: 3.0 μm Application Example 5: Clear Resist for Reference All operations were carried out under yellow light. The following substances were introduced into a 5 mL screw bottle;

```
862 mg  Binder polymer (Acrylate resin Ripoxy SPC-1000,
        available from Showa Denko K.K, Japan)
250 mg  dipentaerythritol hexaacrylate (DPHA)
888 mg  Propylene glycol 1-monomethyl ether 2-acetate (PGMEA)
  5 mg  photopolymerization initiator Irgacure OXEO1,
        available from BASF Japan Ltd.
  3 g   0.5 mm zirconia beads
```

The bottle was sealed then applied to a paint conditioner for 30 minutes to give a clear resist. Zirconia beads were filtered out.

The clear resist was cast onto a glass substrate by means of a spin coating 400 rpm, then dried at 80° C. for 10 minutes. Exposure was carried out using a 250 W super high pressure mercury lamp (USH-250BY, USHIO) at distance of 15 cm. A total exposure dose on the glass filter was adjusted to be 300 mJ/cm$^2$ by using an optical power meter (Model UV-M02 with UV-35 detector, ORC UV Light Measure) and then baked at 230° C. for 30 minutes. Layer thicknesses of the dispersion films were measured by use of a stylus surface profiler (Dektak 6M, ULVAC Inc.). Film thickness: 3.19 μm.

Measurement of Emission Spectra Excited by White LED

An apparatus which consists of a white LED (CREE Xlamp XM-L2 LEDs Cool white with filter (HOYA Light Balancing Filter (Amber) LA-40) with CCT of 7565 K was used for the measurement. The color filter and the color converter was placed onto this light source. Then the light emitted through the color converter was measured by an integral measurement with hemisphere and spectrum detector, QE-2100HMB (from Otsuka Electronics). The spectra were used to determine the relevant light analysis parameters of the emitted light. The results are compiled in table IX.

TABLE IX

| Color filter | Color converter | | Color points by backlight white LED | | |
| --- | --- | --- | --- | --- | --- |
| | | | x | y | Y |
| Appl. ex. 6 | Appl. ex. 1 | blank | 0.269 | 0.681 | 39.46 |
| Appl. ex. 7 | Appl. ex. 1 | Appl. ex. 3 (reference) | 0.269 | 0.681 | 36.33 |
| Appl. ex. 8 | Appl. ex. 1 | Appl. ex. 2 | 0.267 | 0.683 | 37.64/(+3.6%) |
| Appl. ex. 9 | Appl. ex. 1 | Appl. ex. 5 (reference) | 0.269 | 0.681 | 35.27 |
| Appl. ex. 10 | Appl. ex. 1 | Appl. ex. 4 | 0.268 | 0.683 | 36.14/(+2.5%) |

Appl. Ex.: Application Example

IV Method for Producing Color Converters for LCD Backlights:

For preparation of the converters the materials, i.e. polycarbonate, dyes and $TiO_2$ (Kronos 2233) were mixed together according to the desired concentrations (see Table I). The concentrations are given relative to the amount of polymer polycarbonate used. Then methylene chloride was added and the mixtures were stirred overnight. The solutions/dispersions were coated onto a glass surface using an applicator frame. After the solvent had dried off for 2 hours, the film was detached from the glass and dried in vacuum at 50° C.

TABLE X

Converters for blue LED 2

| Example | Yellow dye | Yellow concentration [wt.-%] | Red dye | Red concentration [wt.-%] | $TiO_2$ [wt.-%] | Film thickness [μm] |
| --- | --- | --- | --- | --- | --- | --- |
| A7 | Dye 2 | 0.3775 | Dye 8 | 0.0152 | 0.5% | 47 |
| A8 | Dye 2 | 0.4296 | Dye 8 | 0.0175 | 0.5% | 50 |
| A9 | Dye 2 | 0.5994 | Dye 8 | 0.0042 | — | 46 |

TABLE XI

Photometric data of converters for blue LED

| | CIE-x | CIE-y | CIE-u' | CCT [K] | distance from BBL (duv) |
| --- | --- | --- | --- | --- | --- |
| LED 2 | 0.1542 | 0.0232 | 0.2076 | — | — |
| A7 | 0.2853 | 0.2906 | 0.1929 | 9381 | −1.72E−03 |
| A8 | 0.3176 | 0.3182 | 0.2055 | 6308 | −4.99E−03 |
| A9 | 0.2883 | 0.2852 | 0.1973 | 9328 | −6.55E−03 |

Determination of the DCI Coverage

DCI as well as REC2020 are especially important for TV. DCI is the current digital cinema standard, REC2020 is the proposed standard for UHD content. Both color gamuts especially consider new tones of green. DCI is the common RGB space for digital movie projection. Concentration series of Dye 2 in PC (polycarbonate) with 0.5% $TiO_2$, 67 μm film thickness, excitation at 450 nm were performed as shown in table XII. The color converter was prepared in analogy to the method described above.

TABLE XII concentration series of Dye 2 in PC

| concentration of col. 2 in polycarbonate[#] | QY | lambda max [nm] | FWHM [nm] |
| --- | --- | --- | --- |
| 0.005 | 95% | 489 | 76 |
| 0.02 | 95% | 508 | 72 |
| 0.05 | 96% | 509 | 68 |
| 0.1 | 95% | 511 | 65 |
| 0.2 | 95% | 513 | 61 |
| 0.5 | 94% | 516 | 59 |
| 1 | 93% | 519 | 59 |

[#]% by weight based on the amount of polycarbonate

As can be seen from table XII, when the amount of the dye increases, FWHM gets smaller.

Modeling

Modeling was carried out to determine the DCI coverage and the REC2020 coverage, respectively, to evaluate how much of the color gamut can be covered when using a color converter according to the invention. Two sheets were used, namely a sheet with 1% by weight of Dye 2 and 0.5% by weight of $TiO_2$ in polycarbonate and another sheet with 0.05 wt.-% of Dye 8 and 0.5% by weight $TiO_2$ in polycarbonate. BASF Color filters were used for the modeling.

TABLE XIII

DCI coverage

| DCI Gamut Overlap x, y | 95.11% |
| --- | --- |
| DCI Gamut Area Percent x, y | 102.00% |
| DCI Gamut Overlap u'v' | 97.57% |
| DCI Gamut Area Percent u'v' | 115.22% |
| REC2020 Gamut Overlap x, y | 72.55% |
| REC2020 Gamut Area Percent x, y | 73.18% |
| REC2020 Gamut Overlap u'v' | 80.92% |
| REC2020 Gamut Area Percent u'v' | 83.95% |

As can be seen, the compound according to the invention allows excellent coverage of the color space due to a narrow green peak with a FWHM of less than 60 nm. Color space standards such as DCI and REC2020 are well covered using a color converter according to the invention.

V. Color Converters for Use in Visible Light Communication:

The fluorescent dyes according to the invention were used to produce frequency converters by incorporation into a polymer matrix by the method described in the following. The polymer used was polycarbonate (PC, Macrolon® 2808 from Bayer). About 2.5 g of polymer and 0.032% by weight of the dye was dissolved in about 5 mL of methylene chloride, and 0.5% by weight of $TiO_2$ (Kronos 2220) were dispersed therein, based in each case on the amount of polymer used. The solutions/dispersion obtained were coated onto a glass surface using an applicator frame (from Ericsen, wet film thickness 400 μm). After the solvent had dried off, the film was detached from the glass and dried in a vacuum drying cabinet at 50° C. overnight. Two circular film pieces of 80 to 85 μm thickness having a diameter of 15 mm were punched out of each film, and used as analysis samples.

Measurement of Quantum Yields:

Fluorescence quantum yields (QY) of the analysis samples were measured with the C9920-02 quantum yield measuring system from Hamamatsu. This was done by illuminating each of the samples with light of 445 to 455 nm in an integrating sphere (Ulbricht sphere). By comparison with the reference measurement in the Ulbricht sphere without sample, the unabsorbed fraction of the excitation light and the fluorescent light emitted by the sample are determined by means of a CCD spectrometer. Integration of the intensities of the spectrum of the unabsorbed excitation light and of that of the emitted fluorescent light gives the degree of absorption and fluorescence intensity, respectively, and thus the fluorescence quantum yield of each sample can be calculated.

Determination of the Excited-State Lifetime $\tau_v$ and the Emissive Lifetime $\tau_0$:

The excited-state lifetime ($\tau_v$) of the prepared thin films is measured by exciting the thin films with a pulsed diode laser with an excitation wavelength of 450 nm (Picoquant) operated at 10 kHz (85 µW, 105 µW/cm²) and detecting the emission with time correlated single photon counting (TCSPC). This wavelength was chosen in order to be close to the lighting application, where a blue LED with 450 nm emission maximum is used. A mono-exponential fit to the decay curve was used to determine the excited-state lifetime ($\tau_v$).

The emissive lifetime to is calculated by $\tau_0=\tau_v/QY$. This value is important to compare between different materials as only radiative decay processes are considered here. The following table XIV summarizes the results. Excitation was at 450 nm, the decay rate was determined at the emission maximum which is given in the second column.

TABLE XIV

| | Emission maximum/nm | $\tau_v$ [ns] | $\tau_0$ [ns] | QY [%] |
|---|---|---|---|---|
| 0.032% Dye 2 in PC | 509 | 7.8 | 8.3 | 94.9 |

VI. Color Converters Produced by Extrusion
Equipments
Mixing Roller rack
Extruder Twin Screw 16 mm/36 D, Dr. Collin GmbH
Granulator Granulator, Scheer, Stuttgart
Foils Teach-Line Extruder+Chill-Roll, Dr. Collin GmbH
Test Procedure
Polymer 2 polyethylene terephthalate, PET Terez 3200
Pre-drying 150° C. for 8 hours
Mixing polymer+Dye+TiO₂ (if present) 20 min Turbula Fuchs
Extrusion at 260° C. max. (cold, 150°, 250°, 260°, 260°, 260° and 260° C.)
Drying 150° C. for 8 hours
Foils Teach-Line Extruder 20 mm/25 D
  at 280° C. max. (cold, 260°, 275°, 280°, 280°, 280° and 280° C.)
  Slot nozzle 150 mm width
  Temperature 280° C.
  Chill-Roll
  Roll temperatures 75° C.

Dye 2 was used to produce a color converter by extrusion. For this purpose, the compound of preparation example 1 was incorporated into a matrix composed of polyethylene terephthalate (PET Terez 3200 from TER HELL PLASTIC GMBH) as described above.

Fluorescence quantum yields (FQY) of the analysis samples were measured with the C9920-02 quantum yield measuring system (from Hamamatsu). This was done by illuminating each of the samples with light of 470 nm in an integration sphere (Ulbricht sphere). By comparison with the reference measurement in the Ulbricht sphere without sample, the unabsorbed fraction of the excitation light and the fluorescent light emitted by the sample are determined by means of a CCD spectrometer. Integration of the intensities over the spectrum of the unabsorbed excitation light or over that of the emitted fluorescent light gives the degree of absorption or fluorescence intensity or fluorescence quantum yield of each sample. The results are compiled in table XV below.

The T80 value of the compound of preparation example 1 in the polyethylene terephthalate matrix was determined. T80 is the decay of fluorescence (product abs*QY) to 80% of its initial value, while illuminating with 100 mW/cm² of blue light (450 nm). To this end, polyethylene terephthalate (PET) polymer films and the compound of preparation example 1 were prepared as described above. The results are compiled in table XV.

TABLE XV

| | 0.02% by weight in PET, thickness: 150 µm | 1% by weight in PET, thickness: 140 µm |
|---|---|---|
| FQY | 91% | 87% |
| FWHM | 71 nm | 59 nm |
| Emission λmax | 513 nm | 522 nm |
| T80 | 153 days | >350 days |

Surprisingly, the compound of preparation example 1 does not degrade or decompose during extrusion.

Display Film by Extrusion

The fluorescent dye of preparation example 1 (Dye 2) was used to produce a color converter by extrusion. For this purpose, dye 2, dye 8 and TiO₂ were incorporated into a matrix composed of polyethylene terephthalate as described above and in the concentration listed in table XVI below.

TABLE XVI

Inventive color converter with yellow Dye 2 and red Dye 8

| Ex | Yellow dye | Yellow conc.# | Red dye | Red conc.# | TiO₂ conc.# | Film thickness [µm] |
|---|---|---|---|---|---|---|
| A10 | Dye 2 | 0.075 | Dye 8 | 0.007 | 0.36 | 60 |

LED 2 was used as light source for pumping the color converter A10. The photometric measurement was done as described above. The result is given in table XVIII below.

TABLE XVIII

Photometric data of inventive converters for blue LED 2

| | CIE-x | CIE-y | CIE-u' | CCT [K] | distance from BBL duv |
|---|---|---|---|---|---|
| LED 2 | 0.1539 | 0.0235 | 0.2069 | — | — |
| A10 | 0.2834 | 0.3287 | 0.1777 | 8278 | 1.86E−02 |

The invention claimed is:
1. A cyanoaryl substituted compound of formula (I)

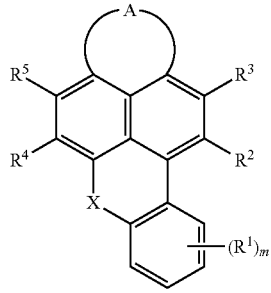
(I)

wherein
m is 0, 1, 2, 3 or 4;
each $R^1$ is independently from each other selected from the group consisting of bromine, chlorine, cyano, $-NR^aR^b$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{10}$-aryl, $C_6$-$C_{10}$-aryloxy and $C_6$-$C_{10}$-aryl-$C_1$-$C_{10}$-alkylene, where the rings of cycloalkyl, heterocycloalkyl, heteroaryl, aryl, aryloxy and aryl-alkylene in the six last-mentioned radicals are unsubstituted or substituted with 1, 2, 3, 4 or 5 identical or different radicals $R^{1a}$, and where $C_1$-$C_{24}$-alkyl, $C_1$-$C_{24}$-haloalkyl, $C_1$-$C_{24}$-alkoxy and the alkylene moiety of $C_6$-$C_{10}$-aryl-$C_1$-$C_{10}$-alkylene may be interrupted by one or more groups selected from the group consisting of O, S and $NR^c$;
$R^2$, $R^3$, $R^4$ and $R^5$ are selected from the group consisting of hydrogen, chlorine, bromine and $C_6$-$C_{10}$-aryl, which comprises one, two or three cyano groups;
with the proviso that at least one of the radicals $R^1$, $R^2$, $R^3$, $R^4$ and $R^5$ is $C_6$-$C_{10}$-aryl, which comprises one, two or three cyano groups;
X is O, S, SO or $SO_2$; and
A is a diradical selected from the group consisting of diradicals of formulae (A.1) and (A.2),

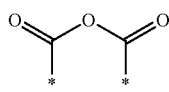
(A.1)

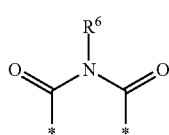
(A.2)

wherein
* in each case denotes a point of attachment to the remainder of the molecule;
$R^6$ is hydrogen, $C_1$-$C_{24}$-alkyl, $C_1$-$C_{24}$-haloalkyl, $C_3$-$C_{24}$-cycloalkyl, $C_6$-$C_{10}$-aryl or $C_6$-$C_{10}$-aryl-$C_1$-$C_{10}$-alkylene, where the rings of cycloalkyl, aryl and aryl-alkylene in the three last-mentioned radicals are unsubstituted or substituted with 1, 2, 3, 4 or 5 identical or different radicals $R^{6a}$, and where $C_1$-$C_{24}$-alkyl, $C_1$-$C_{24}$-haloalkyl and the alkylene moiety of $C_6$-$C_{10}$-aryl-$C_1$-$C_{10}$-alkylene may be interrupted by one or more heteroatoms or heteroatomic groups selected from the group consisting of O, S and $NR^c$;
$R^{1a}$ and $R^{6a}$ are independently from each other selected from the group consisting of $C_1$-$C_{24}$-alkyl, $C_1$-$C_{24}$-fluoroalkyl, $C_1$-$C_{24}$-alkoxy, fluorine, chlorine, bromine and cyano; and
$R^a$, $R^b$ and $R^c$ are independently from each other selected from the group consisting of hydrogen, $C_1$-$C_{20}$-alkyl, $C_3$-$C_{24}$-cycloalkyl, heterocycloalkyl, hetaryl and $C_6$-$C_{10}$-aryl.

2. The cyanoaryl substituted compound of formula (I) according to claim 1, in which X is O.

3. The cyanoaryl substituted compound of formula (I) according to claim 1, where $R^2$ and $R^4$ are each phenyl, which comprises 1, 2 or 3 cyano groups, and $R^3$ and $R^5$ are each hydrogen.

4. The cyanoaryl substituted compound of formula (I) according to claim 1, wherein A is a radical of formula (A.2).

5. The cyanoaryl substituted compound of formula (I) according to claim 4, wherein $R^6$ is selected from the group consisting of linear $C_1$-$C_{24}$-alkyl, a radical of formula (B.1), a radical of formula (B.2) and a radical of formula (B.3)

(B.1)

(B.2)

(B.3)

wherein
# represents the bonding site to the nitrogen atom;
$R^d$ and $R^e$, in the formula (B.1), are independently from each other selected from the group consisting of $C_1$-$C_{22}$-alkyl, where a sum of the carbon atoms of the $R^d$ and $R^e$ radicals is an integer from 2 to 23;
$R^f$, $R^g$ and $R^h$, in the formula (B.2), are independently from each other selected from the group consisting of $C_1$- to $C_{21}$-alkyl, where a sum of the carbon atoms of the $R^f$, $R^g$ and $R^h$ radicals is an integer from 3 to 23; and
$R^i$ and $R^k$, in the formula (B.3), are independently from each other selected from the group consisting of $C_1$- to $C_{21}$-alkyl, where a sum of the carbon atoms of the $R^i$ and $R^k$ radicals is an integer from 2 to 22.

6. The cyanoaryl substituted compound of formula (I) according to claim 4, in which $R^6$ is selected from the group consisting of a radical of formula (C.1), a radical of formula (C.2) and a radical of formula (C.3)

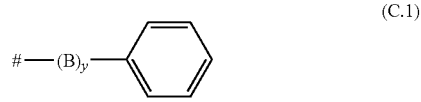
(C.1)

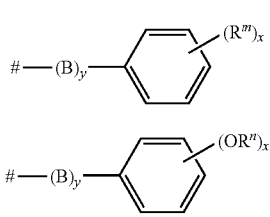

wherein
# represents the bonding side to the nitrogen atom;
B where present, is a $C_1$-$C_{10}$-alkylene group which may be interrupted by one or more nonadjacent groups selected from —O— and —S—;
y is 0 or 1;
each $R^m$ is independently from each other selected from the group consisting of $C_1$-$C_{24}$-alkyl, $C_1$-$C_{24}$-fluoroalkyl, fluorine, chlorine and bromine;
each $R^n$ is independently from each other selected from the group consisting of $C_1$-$C_{24}$-alkyl; and
x in formulae (C.2) and (C.3) is 1, 2, 3, 4 or 5.

7. The cyanoaryl substituted compound of formula (I) according to claim 1, wherein m in formula (I) is 0, 1 or 2 and when m is 1 or 2, each $R^1$ is selected from the group consisting of linear $C_1$-$C_{24}$-alkyl, a radical of formula (D.1), a radical of formula (D.2), a radical of formula (D.3), a radical of formula (D.4) and a radical of formula (D.5)

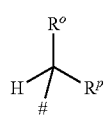

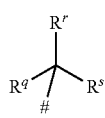

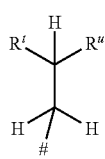

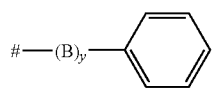

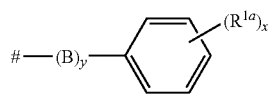

wherein
# represents the bonding site to the remainder of the cyanoaryl substituted compound of formula (I)
$R^o$ and $R^p$, in formula (D.1), are independently from each other selected from the group consisting of $C_1$-$C_{22}$-alkyl, where a sum of the carbon atoms of the $R^o$ and $R^p$ radicals is an integer from 2 to 23;

$R^q$, $R^r$ and $R^s$, in formula (D.2), are independently from each other selected from the group consisting of $C_1$- to $C_{21}$-alkyl, where a sum of the carbon atoms of the $R^q$, $R^r$ and $R^s$ radicals is an integer from 3 to 23;

$R^t$ and $R^u$, in formula (D.3), are independently from each other selected from the group consisting of $C_1$- to $C_{21}$-alkyl, where a sum of the carbon atoms of the $R^t$ and $R^u$ radicals is an integer from 2 to 22;

B where present, is a $C_1$-$C_{10}$-alkylene group which may be interrupted by one or more nonadjacent groups selected from the group consisting of —O— and —S—;

y in formulae (D.4) and (D.5) is 0 or 1;

x in formula (D.5) is 1, 2 or 3; and $R^{1a}$ is selected from the group consisting of cyano, $C_1$-$C_{24}$-alkyl and $C_1$-$C_{24}$-alkoxy.

8. The cyanoaryl substituted compound of formula (I) according to claim 7, wherein m in formula (I) is 0 or 1 and when m is 1, $R^1$ is a radical of formula (D.1), in which $R^o$ and $R^p$ are each independently $C_1$-$C_{12}$-alkyl or $R^1$ is a radical of formula (D.2), in which $R^q$ and $R^s$ are each independently $C_1$-$C_6$-alkyl and $R^r$ is branched $C_4$-$C_{21}$-alkyl or $R^1$ is a radical of formula (D.5), where $R^{1a}$ is cyano or $C_1$-$C_{12}$-alkyl, y is 0 and x is 1 or 2.

9. A color converter comprising at least one cyanoaryl substituted compound of formula (I) according to claim 1 as a fluorescent dye and a polymer matrix,
wherein the polymer matrix is selected from the group consisting of a polystyrene, a polycarbonate, a polyacrylate, a polymethyl methacrylate, a polymethacrylate, a polyvinylpyrrolidone, a polyvinyl acetate, a polyvinyl chloride, a polybutene, a silicone, an epoxy resin, a vinyl ester resin, a polyvinyl alcohol, a poly (ethylene vinylalcohol)-copolymer, a polyacrylonitrile, a polyvinylidene chloride, a polystyrene acrylonitrile, a polybutylene terephthalate, a polyethylene terephthalate, a 2,5-furandicarboxylate polyester, a polyvinyl butyrate, a polyvinyl chloride, a polyamide, a polyoxymethylene, a polyimide, a polyetherimide and mixtures thereof, or the polymer matrix comprises a reaction product of a polymerizable (curable) composition.

10. The color converter according to claim 9, wherein the polymer matrix comprises a polyethylene terephthalate.

11. The color converter according to claim 9, wherein the polymer matrix consists of the reaction product of the polymerizable (curable) composition and
wherein the polymerizable (curable) resin composition is a photosensitive resist composition comprising at least one binder, at least one monomer, at least one photoinitiator and/or photoacid-generator, optionally a thermal radical initiator, optionally an organic solvent, optionally at least one dispersant, optionally at least one surfactant and optionally scattering particles.

12. The color converter according to claim 9, wherein the color converter additionally comprises at least one inorganic white pigment as a scattering body.

13. The color converter according to claim 9, comprising at least one further organic fluorescent dye B selected from the group consisting of
(B1) an aryloxy-substituted perylene-3,4,9,10-tetracarboxylic acid diimide compound of formula (III)

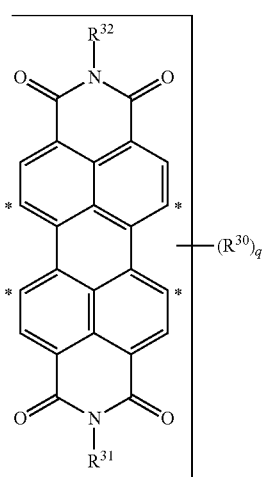

(III)

wherein q is 1, 2, 3 or 4, $R^{30}$ is aryloxy which is unsubstituted or mono- or polysubstituted by halogen, $C_1$-$C_{10}$-alkyl or $C_6$-$C_{10}$-aryl, where the $R^{30}$ radicals are at one or more of the positions indicated by *; and $R^{31}$ and $R^{32}$ are each independently $C_1$-$C_{30}$-alkyl, $C_3$-$C_8$-cycloalkyl, aryl, hetaryl or aryl-$C_1$-$C_{10}$-alkylene, where the (hetero)aromatic ring in the three latter radicals is unsubstituted or mono- or polysubstituted by $C_1$-$C_{10}$-alkyl;

(B2) a perylene-3,4,9,10-tetracarboxylic acid diimide compound of formula (IV)

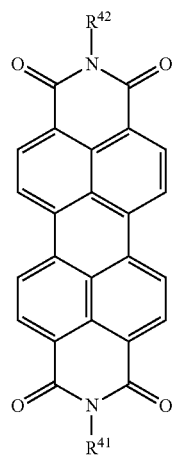

(IV)

wherein $R^{41}$ and $R^{42}$ are independently from each other $C_1$-$C_{30}$-alkyl, $C_3$-$C_8$-cycloalkyl, aryl, hetaryl or aryl-$C_1$-$C_{10}$-alkylene, where the (hetero)aromatic ring in the three latter radicals is unsubstituted or mono- or polysubstituted by $C_1$-$C_{10}$-alkyl;

(B3) a perylene-3,4,9,10-tetracarboxylic acid diimide compound with rigid 2,2'-biphenoxy bridges of formula (V)

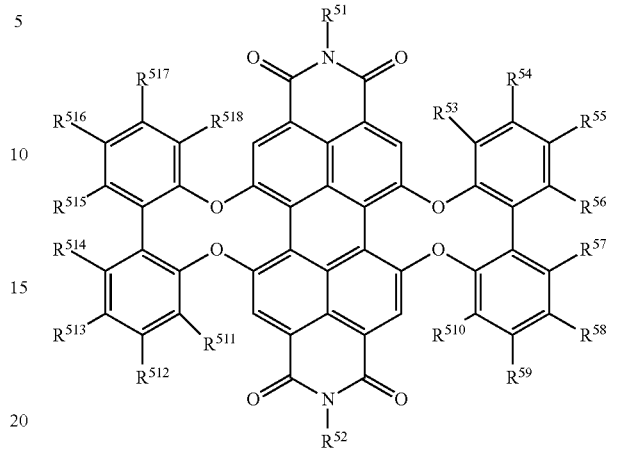

(V)

wherein $R^{51}$ and $R^{52}$ are independently from each other selected from the group consisting of hydrogen, in each case unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkyloxy, $C_6$-$C_{24}$-aryl and $C_6$-$C_{24}$-aryloxy; and $R^{53}$, $R^{54}$, $R^{55}$, $R^{56}$, $R^{57}$, $R^{58}$, $R^{59}$, $R^{510}$, $R^{511}$, $R^{512}$, $R^{513}$, $R^{514}$, $R^{515}$, $R^{516}$, $R^{517}$ and $R^{518}$ are independently from each other selected from the group consisting of hydrogen, halogen, cyano, hydroxyl, mercapto, nitro, —$NE^{51}E^{52}$, —$NR^{Ar51}COR^{Ar52}$, —$CONR^{Ar51}R^{Ar52}$, —$SO_2NR^{Ar51}R^{Ar52}$, —$COOR^{Ar51}$, —$SO_3R^{Ar52}$, in each case unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkoxy, $C_6$-$C_{24}$-aryl, $C_6$-$C_{24}$-aryloxy and $C_6$-$C_{24}$-arylthio, wherein $R^{53}$ and $R^{54}$, $R^{54}$ and $R^{55}$, $R^{55}$ and $R^{56}$, $R^{56}$ and $R^{57}$, $R^{57}$ and $R^{58}$, $R^{58}$ and $R^{59}$, $R^{59}$ and $R^{510}$, $R^{511}$ and $R^{512}$, $R^{512}$ and $R^{513}$, $R^{513}$ and $R^{514}$, $R^{514}$ and $R^{515}$, $R^{515}$ and $R^{516}$, $R^{516}$ and $R^{517}$ and/or $R^{517}$ and $R^{518}$ together with the carbon atoms of the biphenylyl moiety to which they are bonded, may also form a further fused aromatic or non-aromatic ring system wherein the fused ring system is unsubstituted or substituted;

$E^{51}$ and $E^{52}$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl; and $R^{Ar51}$ and $R^{Ar52}$, each independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl;

(B4) a core-cyanated naphthoylbenzimidazole compound of formula (VI)

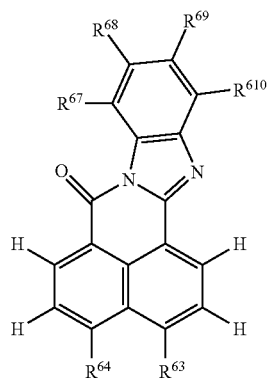

wherein
one of $R^{63}$ or $R^{64}$ independently of each other is cyano and the other radical $R^{63}$ or $R^{64}$ is selected from the group consisting of cyano, phenyl, 4-cyanophenyl and phenyl which comprises 1, 2 or 3 substituents selected from the group consisting of $C_1$-$C_{10}$-alkyl; and
$R^{67}$, $R^{68}$, $R^{69}$, and $R^{610}$ are independently from each other hydrogen, cyano, phenyl, 4-cyanophenyl or phenyl which comprises 1, 2 or 3 substituents selected from the group consisting of $C_1$-$C_{10}$-alkyl; and
mixtures thereof.

14. The color converter according to claim 13, comprising at least one fluorescent dye (B1).

15. A lighting device comprising
(i) at least one LED selected from the group consisting of a blue LED with a center wavelength of emission from 400 nm to 480 nm and a white LED having a correlated color temperature between 3 000 K and 20 000 K; and
(ii) at least one color converter according to claim 9;
wherein the at least one color converter is in a remote phosphor arrangement from the at least one LED.

16. A backlight unit for liquid crystal displays, comprising
(i) at least one light source; and
(ii) at least one color converter according to claim 9;
wherein the at least one color converter is in a remote phosphor arrangement from the at least one light source.

17. A liquid crystal display device comprising
(i) a liquid crystal panel comprising a thin film transistor (TFT) array, a liquid crystal layer, and a color filter array comprising red, green and blue color filters;
(ii) at least one light source; and
(iii) at least one color converter according to claim 9;
where the at least one color converter is arranged between the at least one light source and the liquid crystal panel or is integrated in the color filter array.

18. A self-emissive display device comprising
(i) at least one light source;
(ii) at least one color converter according to claim 9; and
(iii) optionally a color filter array comprising red, green and blue color filters.

19. The self-emissive display device according to claim 18, wherein the at least one light source is selected from the group consisting of a white organic light emitting diode (WOLED), a blue organic light emitting diode with a center wavelength of emission from 400 nm to 480 nm and a micro-LED.

20. A method of converting light, transmitting data, and/or emitting electromagnetic radiation, the method comprising irradiating the cyanoaryl substituted compound of formula (I) according to claim 1 or a color converter comprising the cyanoaryl substituted compound of formula (I),
wherein said light is emitted from a blue LED with a center wavelength of emission between 400 nm and 480 nm such that said light is converted into light of a second, longer wavelength, or from a white LED having a correlated color temperature between 3 000 K and 20 000 K to provide white light having a lower correlated color temperature.

21. A method of converting light, transmitting data, and/or emitting electromagnetic radiation, the method comprising irradiating the color converter according to claim 9,
wherein said light is emitted from a blue LED with a center wavelength of emission between 400 nm and 480 nm to provide white light, or from a white LED having a correlated color temperature between 3 000 K and 20 000 K to provide white light having a lower correlated color temperature.

22. A device capable of producing electric power upon illumination, the device comprising a photovoltaic cell and the color converter according to claim 9,
wherein at least a part of light not absorbed by the photovoltaic cell is absorbed by the color converter.

* * * * *